(12) United States Patent
Lammel et al.

(10) Patent No.: US 9,636,380 B2
(45) Date of Patent: May 2, 2017

(54) OPTOGENETIC CONTROL OF INPUTS TO THE VENTRAL TEGMENTAL AREA

(71) Applicant: The Board of Trustees of the Leland Stanford Junior University, Palo Alto, CA (US)

(72) Inventors: Stephan Lammel, Stanford, CA (US); ByungKook Lim, La Jolla, CA (US); Robert C. Malenka, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/209,004

(22) Filed: Mar. 13, 2014

(65) Prior Publication Data
US 2014/0271479 A1 Sep. 18, 2014

Related U.S. Application Data

(60) Provisional application No. 61/789,486, filed on Mar. 15, 2013, provisional application No. 61/890,000, filed on Oct. 11, 2013.

(51) Int. Cl.
*A61K 49/00* (2006.01)
*A61K 38/17* (2006.01)

(52) U.S. Cl.
CPC ........ *A61K 38/177* (2013.01); *A61K 49/0008* (2013.01)

(58) Field of Classification Search
CPC ...... A61K 38/00; A61K 38/177; A61K 49/00; A61K 49/0008; A61K 48/00; A61K 51/00; A61K 51/08; A61K 51/088; A61K 51/0491; A61K 2123/00; A61K 2121/00; A61K 51/0478; A61K 51/1234; A61K 9/0078; A61K 49/0004; C07F 13/005; A01K 2217/05; G01N 33/5088
USPC .... 424/1.11, 1.65, 1.69, 9.1, 9.2; 514/1, 1.1, 514/17.7, 17.8, 17.9, 18.1, 21.2, 21.3; 530/300, 324, 325, 350
See application file for complete search history.

(56) References Cited

U.S. PATENT DOCUMENTS

| | | | |
|---|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Land et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |

(Continued)

FOREIGN PATENT DOCUMENTS

| | | |
|---|---|---|
| CN | 1079464 A | 12/1993 |
| EP | 1334748 | 8/2003 |
| EP | 1873566 | 1/2008 |
| JP | 6295350 | 10/1994 |
| JP | 2004534508 | 11/2004 |
| JP | 2005034073 A | 2/2005 |
| JP | 2010227537 A | 10/2010 |
| JP | 2012508581 | 4/2012 |
| WO | WO 96/32076 | 10/1996 |

(Continued)

OTHER PUBLICATIONS

Babin et al., "Zebrafish Models of Human Motor Neuron Diseases: Advantages and Limitations", Progress in Neurobiology (2014), 118:36-58.

(Continued)

*Primary Examiner* — D L Jones
(74) *Attorney, Agent, or Firm* — Bozicevic, Field & Francis LLP; Paula A. Borden

(57) ABSTRACT

The present disclosure provides a method of inducing or modulating reward- or aversive-related behaviors in animals using light-responsive opsins. The present disclosure provides methods of identifying or screening compounds that may be used to treating mental disorders, or are relevant to disrupt or improve reward- or aversive related behaviors.

14 Claims, 47 Drawing Sheets

(56) References Cited

U.S. PATENT DOCUMENTS

| | | |
|---|---|---|
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 9,057,734 B2 | 6/2015 | Cohen |
| 9,249,234 B2 | 2/2016 | Deisseroth et al. |
| 9,271,674 B2 * | 3/2016 | Deisseroth ............ A61B 5/055 |
| 9,359,449 B2 | 6/2016 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0267118 A1 | 12/2004 | Dawson |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |

(56) References Cited

U.S. PATENT DOCUMENTS

| | | |
|---|---|---|
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Deisseroth et al. |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0234273 A1 | 9/2010 | Deisseroth et al. |
| 2011/0021970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Deisseroth et al. |
| 2011/0172653 A1 | 7/2011 | Deisseroth et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0089503 A1 | 4/2013 | Deisseroth et al. |
| 2013/0090454 A1 | 4/2013 | Deisseroth et al. |
| 2013/0144359 A1 | 6/2013 | Kishawi et al. |
| 2013/0184817 A1 | 7/2013 | Deisseroth et al. |
| 2013/0224821 A1 | 8/2013 | Deisseroth et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0289676 A1 | 10/2013 | Deisseroth et al. |
| 2013/0295015 A1 | 11/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0331441 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0024701 A1 | 1/2014 | Deisseroth et al. |
| 2014/0082758 A1 | 3/2014 | Deisseroth et al. |
| 2014/0113367 A1 | 4/2014 | Deisseroth et al. |
| 2014/0148880 A1 | 5/2014 | Deisseroth et al. |
| 2014/0235826 A1 | 8/2014 | Deisseroth et al. |
| 2014/0309705 A1 | 10/2014 | Deisseroth et al. |
| 2014/0323849 A1 | 10/2014 | Deisseroth et al. |
| 2014/0324133 A1 | 10/2014 | Deisseroth et al. |
| 2014/0358067 A1 | 12/2014 | Deisseroth et al. |
| 2015/0112411 A1 | 4/2015 | Beckman et al. |
| 2016/0038764 A1* | 2/2016 | Deisseroth ............ A61N 5/0618 607/88 |

FOREIGN PATENT DOCUMENTS

| | | |
|---|---|---|
| WO | WO 00/27293 | 5/2000 |
| WO | WO 01/25466 | 4/2001 |
| WO | WO 03/016486 | 2/2003 |
| WO | WO 2013/016486 | 2/2003 |
| WO | WO 03/040323 | 5/2003 |
| WO | WO 03/046141 | 6/2003 |
| WO | WO 03/084994 | 10/2003 |
| WO | WO 03/102156 | 12/2003 |
| WO | WO 2004/033647 | 4/2004 |
| WO | WO 2006/103678 | 10/2006 |
| WO | WO 2007/024391 | 3/2007 |
| WO | WO 2007/131180 | 11/2007 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009-131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Santana et al., "Can Zebrafish Be Used as Animal Model to Study Alzheimer's Disease?" Am. J. Neurodegener. Dis. (2012), 1(1):32-48.

Sheikh et al., "Neurodegenerative Diseases: Multifactorial Conformational Diseases and Their Therapeutic Interventions", Journal of Neurodegenerative Diseases (2013), Article ID 563481:1-8.

Suzuki et al., "Stable Transgene Expression from HSV Amplicon Vectors in the Brain: Potential Involvement of Immunoregulatory Signals", Molecular Therapy (2008), 16(10):1727-1736.

Thomas et al., "Progress and Problems with the Use of Viral Vectors for Gene", Nat. Rev. Genet. (2003), 4(5):346-358.

(56) References Cited

OTHER PUBLICATIONS

U.S. Appl. No. 14/301,718, filed Jun. 11, 2014, Deisseroth, et al.
U.S. Appl. No. 14/365,477, filed Jun. 13, 2014, Deisseroth, et al.
U.S. Appl. No. 14/385,331, filed Sep. 15, 2014, Deisseroth, et al.
U.S. Appl. No. 14/537,290, filed Nov. 10, 2014, Deisseroth, et al.
U.S. Appl. No. 14/537,305, filed Nov. 10, 2014, Deisseroth, et al.
Balint et al., "The Nitrate Transporting Photochemical Reaction Cycle of the Pharanois Halorhodopsin", Biophysical Journal, 2004, 86:1655-1663.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full=Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine D2 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 64, No. 6, pp. 1463-1473 (2003).
Adamantidis et al., "Optogenetic Interrogation of Dopaminergic Modulation of the Multiple Phases of Reward-Seeking Behavior", J. Neurosci (2011), 31(30):10829-35.
Aebischer et al., "Long-Term Cross-Species Brain Transplantation of a Polymer-Encapsulated Dopamine-Secreting Cell Line", Experimental Neurology (1991), 111:269-275.
Ahmad et al., "The Drosophila rhodopsin cytoplasmic tail domain is required for maintenance of rhabdomere structure", The FASEB Journal (2007), 21:449-455.
Airan et al., "Temporally Precise in vivo Control of Intracellular Signaling", Nature (2009), 458(7241):1025-1029.
Akirav et al., "The role of the medial prefrontal cortex-amygdala circuit in stress effects on the extinction of fear", Neural Plasticity (2007), 2007:Article ID 30873.
Ang et at., "Hippocampal CA1 Circuitry Dynamically Gates Direct Cortical Inputs Preferentially at Theta Frequencies", The Journal of Neurosurgery (2005), 25(42):9567-9580.
Araki et al., "Site-Directed Integration of the cre Gene Mediated by Cre Recombinase Using a Combination of Mutant lox Sites", Nucleic Acids Research (2002), 30(19):1-8.

(56) References Cited

OTHER PUBLICATIONS

Aravanis et al., "An optical neural interface: in vivo control of rodent motor cortex with integrated fiberoptic and optogenetic technology", J. Neural. Eng. (2007), 4(3):S143-S156.
Arenkiel et al., "In vivo light-induced activation of neural circuitry in transgenic mice expressing Channelrhodopsin-2", Neuron (2007), 54:205-218.
Argos et al., "The integrase family of site-specific recombinases: regional similarities and global diversity", The EMBO Journal (1986), 5(2):433-440.
Bamberg et al., "Light-driven proton or chloride pumping by halorhodopsin", Proc. Natl. Academy Science USA (1993), 90(2):639-643.
Banghart et al., "Light-activated ion channels for remote control of neuronal firing", Nature Neuroscience (2004), 7(12):1381-1386.
Basil et al., "Is There Evidence for Effectiveness of Transcranial Magnetic Stimulation in the Treatment of Psychiatric Disorders?" Psychiatry (2005), 2(11):64-69.
Bebbington et al., "The use of vectors based on gene amplification for the expression of cloned genes in mammalian cells" in "DNA cloning vol. 3", Academic Press, New York (2007).
Benabid, "Future strategies to restore brain functions," Conference proceedings from Medicine Meets Millennium: World Congress of Medicine and Health (2000), 6 pages.
Benoist et al., "In vivo sequence requirements of the SV40 early promoter region", Nature (1981), 290(5804):304-310.
Berges et al., "Transduction of Brain by Herpes Simplex Virus Vectors", Molecular Therapy (2007), 15(1):20-29.
Berke et al., "Addiction, Dopamine, and the Molecular Mechanisms of Memory", Molecular Plasticity (2000), 25:515-532.
Berndt et al., "Bi-stable neural state switches", Nature Neuroscience (2009), 12(2):229-234.
Berndt et al., "Structure-guided transformation of channelrhodopsin into a light-activated chloride channel", Science (2014), 344:420-424.
Berridge et al., "The Versatility and Universality of Calcium Signaling", Nature Reviews: Molecular Cell Biology (2000), 1:11-21.
Bocquet et al., "A prokaryotic proton-gated ion channel from the nicotinic acetylcholine receptor family", Nature Letters (2007), 445:116-119.
Boyden et al., "Millisecond-timescale, genetically targeted optical control of neural activity", Nature Neuroscience (2005), 8(9):1263-1268.
Bi et al., "Ectopic Expression of a Microbial-Type Rhodopsin Restores Visual Responses in Mice with Photoreceptor Degeneration", Neuron (2006), 50(1):23-33.
Bi et al., "Synaptic Modifications in Cultured Hippocampal Neurons: Dependence on Spike Timing, Synaptic Strength, and Postsynaptic Cell Type", Journal of Neuroscience (1998), 18(24):10464-10472.
Blomer et al., "Highly Efficient and Sustained Gene Transfer in Adult Neurons with Lentivirus Vector", Journal of Virology (1997), 71(9):6641-6649.
Braun, "Two Light-activated Conductances in the Eye of the Green Alga Volvox carteri", Biophys J. (1999), 76(3):1668-1678.
Brinton et al., "Preclinical analyses of the therapeutic potential of allopregnanolone to promote neurogenesis in vitro and in vivo in transgenic mouse model of Alzheimer's disease", Current Alzheimer Research (2006), 3(1):11-17.
Brosenitsch et al., "Physiological Patterns of Electrical Stimulation Can Induce Neuronal Gene Expression by Activating N-Type Calcium Channels", Journal of Neuroscience (2001), 21(8):2571-2579.
Brown et al., "Long-term potentiation induced by $\theta$ frequency stimulation is regulated by a protein phosphate-operated gate", The Journal of Neuroscience (2000), 20(21):7880-7887.
Callaway et al., "Photostimulation using caged glutamate reveals functional circuitry in living brain slices", Proc. Natl. Acad. Sci. USA. (1993), 90:7661-7665.
Campagnola et al., "Fiber-coupled light-emitting diode for localized photostimulation of neurons expressing channelrhodopsin-2", Journal of Neuroscience Methods (2008), 169: Issue 1. Abstract only.
Cardin et al., "Driving Fast spiking Cells Induces Gamma Rhythm and Controls Sensory Responses", Nature (2009), 459(7247):663-667.
Cazillis et al., "VIP and PACAP induce selective neuronal differentiation of mouse embryonic stem cells", Eur J Neurosci (2004), 19(4):798-808.
Cenatiempo, "Prokaryotic gene expression in vitro: transcription-translation coupled systems", Biochimie (1986), 68(4):505-515.
Chow et al., "Optogenetics and translational medicine", Sci Transl Med. (2013), 5(177):177.
Claudio et al., "Nucleotide and deduced amino acid sequences of Torpedo californica acetylcholine receptor gamma subunit", PNAS USA (1983), 80:1111-1115.
Collingridge et al., "Inhibitory post-synaptic currents in rat hippocampal CA1 neurones", J. Physiol. (1984), 356:551-564.
Covington et al., "Antidepressant Effect of Optogenetic Stimulation of the Medial Prefrontal Cortex", Journal of Neuroscience (2010), 30(48):16082-16090.
Crouse et al., "Expression and amplification of engineered mouse dihydrofolate reductase minigenes", Mol. Cell. Biol. (1983), 3(2):257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus", J. Electron. Microsc. Tech. (1990), 15(4):352-368.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology (1991), 310:316-336.
Cui et al., "Electrochemical deposition and characterization of conducting polymer polypyrrole/PSS on multichannel neural probes," Sensors and Actuators (2001), 93(1):8-18.
Date et al., "Grafting of Encapsulated Dopamine-Secreting Cells in Parkinson's Disease: Long-Term Primate Study", Cell Transplant (2000), 9:705-709.
Dalva et al., "Rearrangements of Synaptic Connections in Visual Cortex Revealed by Laser Photostimulation", Science (1994), 265:255-258.
Dederen et al., "Retrograde neuronal tracing with cholera toxin B subunit: comparison of three different visualization methods", Histochemical Journal (1994), 26:856-862.
De Foubert et al., "Fluoxetine-Induced Change in Rat Brain Expression of Brain-Derived Neurotrophic Factor Varies Depending on Length of Treatment," Neuroscience (2004), 128:597-604.
Deisseroth et al., "Signaling from Synapse to Nucleus: Postsynaptic CREB Phosphorylation During Multiple Forms of Hippocampal Synaptic Plasticity", Neuron (1996), 16:89-101.
Deisseroth et al., "Translocation of Calmodulin to the Nucleus Supports CREB Phosphorylation in Hippocampal Neurons", Nature (1998), 392:198-202.
Deisseroth et al., "Signaling from Synapse to Nucleus: the logic Behind the Mechanisms", Currrent Opinion in Neurobiology (2003), 13:354-365.
Deisseroth et al., "Excitation-neurogenesis Coupling in Adult Neural Stem/Progenitor Cells", Neuron (2004), 42:535-552.
Deisseroth, "Next-generation optical technologies for illuminating genetically targeted brain circuits", The Journal of Neuroscience (2006), 26(41):10380-10386.
Deisseroth, et al., "Controlling the Brain with Light", Scientific American (2010), 303:48-55.
Delaney et al., "Evidence for a long-lived 13-cis-containing intermediate in the photocycle of the leu 93 → ala bacteriorhodopsin mutant", J. Physical Chemistry B (1997), 101(29):5619-5621.
Denk et al., "Anatomical and functional imaging of neurons using 2-photon laser scanning microscopy", Journal of Neuroscience Methods (1994), 54:151-162.
Ditterich et al., "Microstimulation of visual cortex affects the speed of perceptual decisions", Nature Neuroscience (2003), 6(8):891-898.

(56) References Cited

OTHER PUBLICATIONS

Dittgen et al., "Lentivirus-based genetic manipulations of cortical neurons and their optical and electrophysiological monitoring in vivo", PNAS (2004), 101(52):18206-18211.
Douglass et al., "Escape Behavior Elicited by Single, Channelrhodopsin-2-evoked Spikes in Zebrafish Somatosensory Neurons", Curr Biol. (2008), 18(15):1133-1137.
Ehrlich et al., "Amygdala inhibitory circuits and the control of fear memory", Neuron (2009), 62:757-771.
Eijkelkamp et al., "Neurological perspectives on voltage-gated sodium channels", Brain (2012), 135:2585-2612.
Emerich et al., "A Novel Approach to Neural Transplantation in Parkinson's Disease: Use of Polymer-Encapsulated Cell Therapy", Neuroscience and Biobehavioral Reviews (1992), 16:437-447.
Ensell et al., "Silicon-based microelectrodes for neurophysiology, micromachined from silicon-on-insulator wafers", Med. Biol. Eng. Comput. (2000), 38:175-179.
Eisen, "Treatment of amyotrophic lateral sclerosis", Drugs Aging (1999), 14(3):173-196.
Ernst et al., "Photoactivation of Channelrhodopsin", J. Biol. Chem. (2008), 283(3):1637-1643.
Evanko, "Optical excitation yin and yang", Nature Methods (2007), 4:384.
Esposito et al., "The integrase family of tyrosine recombinases: evolution of a conserved active site domain", Nucleic Acids Research (1997), 25(18):3605-3614.
Fabian et al., "Transneuronal transport of lectins", Brain Research (1985), 344:41-48.
Falconer et al., "High-throughput screening for ion channel modulators", Journal of Biomolecular Screening (2002), 7(5):460-465.
Farber et al., "Identification of Presynaptic Neurons by Laser Photostimulation", Science (1983), 222:1025-1027.
Feng et al., "Imaging Neuronal Subsets in Transgenic Mice Expressing Multiple Spectral Variants of GFP", Neuron (2000), 28:41-51.
Fenno et al., "The development and application of optogenetics", Annual Review of Neuroscience (2011), 34(1):389-412.
Fiala et al., "Optogenetic approaches in neuroscience", Current Biology (2010), 20(20):R897-R903.
Fisher et al., "Spatiotemporal Activity Patterns During Respiratory Rhythmogenesis in the Rat Ventrolateral Medulla," The Journal of Neurophysiol (2006), 95:1982-1991.
Fitzsimons et al., "Promotors and Regulatory Elements that Improve Adeno-Associated Virus Transgene Expression in the Brain", Methods (2002), 28:227-236.
Foster, "Bright blue times", Nature (2005), 433:698-699.
Fox et al., "A gene neuron expression fingerprint of C. elegans embryonic motor neurons", BMC Genomics (2005), 6(42):1-23.
Garrido et al., "A targeting motif involved in sodium channel clustering at the axonal initial segment", Science (2003), 300(5628):2091-2094.
Genbank Accession No. DQ094781 (Jan. 15, 2008).
Gelvich et al., "Contact flexible microstrip applicators (CFMA) in a range from microwaves up to short waves", IEEE Transactions on Biomedical Engineering (2002), 49(9):1015-1023.
Gigg et al., "Glutamatergic hippocampal formation projections to prefrontal cortex in the rat are regulated by GABAergic inhibition and show convergence with glutamatergic projections from the limbic thalamus", Hippocampus (1994), 4(2):189-198.
Gilman et al., "Isolation of sigma-28-specific promoters from *Bacillus subtilis* DNA" Gene (1984), 32(1-2):1 1-20.
Glick et al., "Factors affecting the expression of foreign proteins in *Escherichia coli*", Journal of Industrial Microbiology (1987), 1(5):277-282.
Goekoop et al., "Cholinergic challenge in Alzheimer patients and mild cognitive impairment differentially affects hippocampal activation-a pharmacological fMRI study", Brain (2006), 129:141-157.
Gold et al., "Representation of a perceptual decision in developing oculomotor commands", Nature (2000), 404:390-394.
Gonzalez et al., "Cell-Based Assays and Instrumentation for Screening Ion-Channel Targets", DDT (1999), 4(9):431-439.
Gordon et al., "Regulation of Thy-1 Gene Expression in Transgenic Mice", Cell (1987), 50:445-452.
Gorelova et al., "The course of neural projection from the prefrontal cortex to the nucleus accumbens in the rat", Neuroscience (1997), 76(3):689-706.
Goshen et al., "Dynamics of Retrieval Strategies for Remote Memories", Cell (2011), 147:678-589.
Gottesman et al., "Bacterial regulation: global regulatory networks", Ann. Rev. Genet. (1984), 18:415-441.
Gradinaru et al., "Targeting and readout strategies for fast optical neural control in vitro and in vivo", J Neuroscience (2007), 27(52):14231-14238.
Gradinaru et al., "ENpHR: a Natronomonas Halorhodopsin Enhanced for Optogenetic Applications", Brain Cell Biol. (2008), 36(1-4):129-139.
Gradinaru et al., "Optical Deconstruction of Parkinsonian neural circuitry", Science (2009), 324(5925):354-359.
Gradinaru et al., "Molecular and Cellular Approaches for Diversifying and Extending Optogenetics", Cell (2010), 141(1):154-165.
Greenberg et al., "Three-year outcomes in deep brain stimulation for highly resistant obsessive-compulsive disorder", Neuropsychopharmacology (2006), 31:2384-2393.
Gregory et al., "Integration site for *Streptomyces* phage φBT1 and development of site-specific integrating vectors", Journal of Bacteriology (2003), 185(17):5320-5323.
Groth et al., "Phage integrases: biology and applications", Journal of Molecular Biology (2004), 335:667-678.
Groth et al., "A phage integrase directs efficient site-specific integration in human cells", PNAS (2000), 97(11):5995-6000.
Guatteo et al., "Temperature sensitivity of dopaminergic neurons of the substantia nigra pars compacta: Involvement of transient receptor potential channels", Journal of Neurophysiol. (2005), 94:3069-3080.
Gulick et al., "Transfection using DEAE-Dextran" Supplement 40, Current Protocols in Molecular Biology (1997), Supplement 40:9. 2.1-9.2.10.
Gunaydin et al., "Ultrafast optogenetic control", Nature Neuroscience (2010), 13(3):387-392.
Gur et al., "A Dissociation Between Brain Activity and Perception: Chromatically Opponent Cortical Neurons Signal Chromatic Flicker that is not Perceived", Vision Research (1997), 37(4):377-382.
Hallet et al., "Transposition and site-specific recombination: adapting DNA cut-and-paste mechanisms to a variety of genetic rearrangements", FEMS Microbiology Reviews (1997), 21(2):157-178.
Hamer et al., "Regulation In Vivo of a cloned mammalian gene: cadmium induces the transcription of a mouse metallothionein gene in SV40 vectors", Journal of Molecular Applied Genetics (1982), 1(4):273-288.
Han et al., "Multiple-Color Optical Activation, Silencing, and Desynchronization of Neural Activity with Single-Spike Temporal Resolution", PLoS One (2007), 2(3):1-12.
Han et al., "Two-color, bi-directional optical voltage control of genetically-targeted neurons", CoSyne (2007), Abstract Presentation, Poster III-67, p. 269, Presented Feb. 24, 2007.
Hausser et al., "Tonic Synaptic Inhibition Modulates Neuronal Output Pattern and Spatiotemporal Synaptic Integration", Neuron (1997), 19:665-678.
Hegemann et al., "All-trans Retinal Constitutes the Functional Chromophore in *Chlamydomonas* rhodopsin", Biophys. J. (1991), 60:1477-1489.
Herlitze et al., "New Optical Tools for Controlling Neuronal Activity", Curr. Opin. Neurobiol. (2007), 17(1):87-94.
Herry et al., "Switching on and off fear by distinct neuronal circuits", Nature (2008), 454:600-606.
Hikida et al., "Increased sensitivity to cocaine by cholinergic cell ablation in nucleus accumbens," PNAS (2001), 98(23):13351-13354.
Hikida et al., "Acetylcholine enhancement in the nucleus accumbens prevents addictive behaviors of cocaine and morphine", PNAS (2003), 100(10):6169-6173.

(56) References Cited

OTHER PUBLICATIONS

Hildebrandt et al., "Bacteriorhodopsin expressed in *Schizosaccharomyces pombe* pumps protons through the plasma membrane", PNAS (1993), 90:3578-3582.
Hira et al., "Transcranial optogenetic stimulation for functional mapping of the motor cortex", J Neurosci Methods (2009), 179:258-263.
Hirase et al., "Multiphoton stimulation of neurons", J Neurobiol (2002), 51(3):237-247.
Hodaie et al., "Chronic Anterior Thalamus Stimulation for Intractable Epilepsy", Epilepsia (2002), 43:603-608.
Hoffman et al., "K+ Channel Regulation of Signal Propagation in Dendrites of Hippocampal Pyramidal Neurons", Nature (1997), 387:869-874.
Hofherr et al., "Selective Golgi export of Kir2.1 controls the stoichiometry of functional Kir2.x channel heteromers", Journal of Cell Science (2005), 118:1935-1943.
Hosokawa et al., "Imaging spatio-temporal patterns of long-term potentiation in mouse hippocampus", Philos. Trans. R. Soc. Lond. B. (2003), 358:689-693.
Hustler et al., "Acetylcholinesterase staining in human auditory and language cortices: regional variation of structural features", Cereb Cortex (1996), 6(2):260-70.
Hynynen et al., "Clinical applications of focused ultrasound—The brain", Int. J. Hyperthermia (2007), 23(2):193-202.
International Search Report for International Application No. PCT/US2009/053474, dated Oct. 8, 2009.
Isenberg et al., "Cloning of a Putative Neuronal Nicotinic Aceylcholine Receptor Subunit", Journal of Neurochemistry (1989), 52:988-991.
Iyer et al., "Virally mediated optogenetic excitation and inhibition of pain in freely moving nontransgenic mice", Nat Biotechnol. (2014), 32(3):274-278.
Ji et al., "Light-evoked Somatosensory Perception of Transgenic Rats that Express Channelrhodopsin-2 in Dorsal Root Ganglion Cells", PLoS One (2012), 7(3):e32699.
Jimenez et al., "Nuclear disconnection within the amygdala reveals a direct pathway to fear", Learning Memory (2009), 16:766-768.
Jekely, "Evolution of Phototaxis", Phil. Trans. R. Soc. B (2009), 364:2795-2808.
Jennings et al., "Distinct extended amygdala circuits for divergent motivational states," Nature (2013), 496:224-228.
Johansen et al., "Optical Activation of Lateral Amygdala Pyramidal Cells Instructs Associative Fear Learning", PNAS (2010), 107(28):12692-12697.
Johnston et al., "Isolation of the yeast regulatory gene *GAL4* and analysis of its dosage effects on the galactose/melibiose regulon", PNAS (1982), 79:6971-6975.
Kandel et al., "Electrophysiology of Hippocampal Neurons: I. Sequential Invasion and Synaptic Organization", J Neurophysiol (1961), 24:225-242.
Kandel et al., "Electrophysiology of Hippocampal Neurons: II. After-Potentials and Repetitive Firing", J Neurophysiol. (1961), 24:243-259.
Karreman et al., "On the use of double FLP recognition targets (FRTs) in the LTR of retroviruses for the construction of high producer cell lines", Nucleic Acids Research (1996), 24(9):1616-1624.
Kato et al., "Present and future status of noninvasive selective deep heating using RF in hyperthermia", Med & Biol. Eng. & Comput 31 Supp: S2-11 (1993), Abstract, p. S2 only.
Katz et al., "Scanning laser photostimulation: a new approach for analyzing brain circuits", Journal of Neuroscience Methods (1994), 54:205-218.
Khodakaramian et al., "Expression of Cre Recombinase during Transient Phage Infection Permits Efficient Marker Removal in *Streptomyces*", Nucleic Acids Research (2006), 34(3:e20):1-5.
Khosravani et al., "Voltage-Gated Calcium Channels and Idiopathic Generalized Epilepsies", Physiol. Rev. (2006), 86:941-966.

Kianianmomeni et al., "Channelrhodopsins of Volvox carteri are Photochromic Proteins that are Specifically Expressed in Somatic Cells under Control of Light, Temperature, and the Sex Inducer", Plant Physiology (2009), 151(1):347-366.
Kim et al., "PDZ domain proteins of synapses", Nature Reviews Neuroscience (2004), 5(10):771-781.
Kim et al., "Diverging neural pathways assemble a behavioural state from separable features in anxiety", Nature (2013), 496(7444):219-223.
Kim et al., "Light-Driven Activation of $\beta$2-Adrenergic Receptor Signaling by a Chimeric Rhodopsin Containing the $\beta$2-Adrenergic Receptor Cytoplasmic Loops," Biochemistry (2005), 44(7):2284-2292.
Kingston et al., "Transfection of DNA into Eukaryotic Cells," Supplement 63, Current Protocols in Molecular Biology, 1996, 9.1.1-9.1.11, 11 pages.
Kingston et al., "Transfection and Expression of Cloned DNA," Supplement 31, Current Protocols in Immunology, 1999, 10.13.1-10.13.9.
Kinoshita, et al., "Optogenetically Induced Supression of Neural Activity in the Macaque Motor Cortex", Poster Sessions Somatomotor System, Others, Society for Neuroscience Meeting (2010), pp. 141-154.
Kita et al., "Effects of dopamine agonists and antagonists on optical responses evoked in rat frontal cortex slices after stimulation of the subcortical white matter," Exp. Brain Research (1999), 125:383-388.
Kitabatake et al., "Impairment of reward-related learning by cholinergic cell ablation in the striatum", PNAS (2003), 100(13):7965-7970.
Kitayama et al., "Regulation of neuronal differentiation by N-methyl-D-aspartate receptors expressed in neural progenitor cells isolated from adult mouse hippocampus," Journal of Neurosci Research (2004), 76(5):599-612.
Klausberger et al., "Brain-state- and cell-type-specific firing of hippocampal interneurons in vivo", Nature (2003), 421:844-848.
Kocsis et al., "Regenerating Mammalian Nerve Fibres: Changes in Action Potential Wave from and Firing Characteristics Following Blockage of Potassium Conductance", Proc. R. Soc. Lond. (1982), B 217:77-87.
Kokel et al., "Photochemical activation of TRPA1 channels in neurons and animals", Nat. Chem. Biol. (2013), 9(4):257-263.
Knopfel et al., "Optical Probing of Neuronal Circuit Dynamics: Genetically Encoded Versus Classical Fluorescent Sensors", Trends Neurosci (2006), 29(3):160-166.
Kuhlman et al., "High-Resolution Labeling and Functional Manipulation of Specific Neuron Types in Mouse Brain by Cre-Activated Viral Gene Expression" PLoS One (2008), e2005, 3(4):1-11.
Kunkler et al., "Optical Current Source Density Analysis in Hippocampal Organotypic Culture Shows that Spreading Depression Occurs with Uniquely Reversing Current," The Journal of Neuroscience (2005), 25(15):3952-3961.
Lalumiere, "A new technique for controlling the brain: optogenetics and its potential for use in research and the clinic", Brain Stimulation (2011), 4:1-6.
Lanyi et al., "The primary structure of a Halorhodopsin from Natronobacterium Pharaonis" Journal of Biological Chemistry (1990), 265(3):1253-1260.
Landy, "Mechanistic and structural complexity in the site-specific recombination pathways of Int and FLP", Current Opinion in Genetics and Development (1993), 3:699-707.
Lee et al., "Sterotactic Injection of Adenoviral Vectors that Target Gene Expression to Specific Pituitary Cell Types: Implications for Gene Therapy", Neurosurgery (2000), 46(6):1461-1469.
Lee et al., "Potassium Channel Gene Therapy Can Prevent Neuron Death Resulting from Necrotic and Apoptotic Insults", Journal of Neurochemistry (2003), 85:1079-1088.
Levitan et al., "Surface Expression of Kv1 Voltage-Gated K+ Channels Is Governed by a C-terminal Motif," Trends Cardiovasc. Med. (2000), 10(7):317-320.
Li et al., "Surface Expression of Kv1 Channels is Governed by a C-Terminal Motif", J. Bio. Chem. (2000), 275(16):11597-11602.

(56) References Cited

OTHER PUBLICATIONS

Li et al., "Fast noninvasive activation and inhibition of neural and network activity by vertebrate rhodopsin and green algae channel rhodopsin." PNAS (2005), 102(49):17816-17821.
Lim et al., "A Novel Targeting Signal for Proximal Clustering of the Kv2.1 K+ Channel in Hippocampal Neurons", Neuron (2000), 25:385-397.
Lima, et al., "Remote Control of Behavior through Genetically Targeted Photostimulation of Neurons", Cell (2005), 121:141-152.
Liman et al., "Subunit Stoichiometry of a Mammalian K+ Channel Determined by Construction of Multimeria cans," Neuron (1992), 9:861-871.
Liu et al., "Optogenetics 3.0", Cell (2010), 141(1):22-24.
Lin, "A user's guide to channel rhodopsin variants: features, limitations and future developments", Exp. Physiol. (2010), 96(1):19-25.
Liske et al., "Optical inhibition of motor nerve and muscle activity in vivo", Muscle Nerve (2013), 47(6):916-921.
Llewellyn et al., "Orderly recruitment of motor units under optical control in vivo", Nat Med. (2010), 16(10):1161-1165.
Louis et al., "Cloning and sequencing of the cellular-viral junctions from the human adenovirus type 5 transformed 293 cell line," Virology (1997), 233:423-429.
Loetterle et al., "Cerebellar Stimulation: Pacing the Brain", American Journal of Nursing (1975), 75(6):958-960.
Lonnerberg et al., "Regulatory Region in Choline Acetyltransferase Gene Directs Developmental and Tissue-Specific Expression in Transgenic mice", Proc. Natl. Acad. Sci. USA (1995), 92(9):4046-4050.
Luecke et al., "Structural Changes in Bacteriorhodopsin During Ion Transport at 2 Angstrom Resolution," Science (1999), 286:255-260.
Lyznik et al., "FLP-mediated recombination of *FRT* sites in the maize genome," Nucleic Acids Research (1996), 24(19):3784-3789.
Ma et al., "Role of ER Export Signals in Controlling Surface Potassium Channel Numbers," Science (2001), 291:316-319.
Malin et al., "Involvement of the rostral anterior cingulate cortex in consolidation of inhibitory avoidance memory: Interaction with the basolateral amygdala", Neurobiol Learn Mem. (2007), 87(2):295-302.
Marin et al., The Amino Terminus of the Fourth Cytoplasmic Loop of Rhodopsin Modulates Rhodopsin-Transduction Interaction, The Journal of Biological Chemistry (2000), 275:1930-1936.
Mancuso et al., "Optogenetic probing of functional brain circuitry", Experimental Physiology (2010), 96(1):26-33.
Mann et at., "Perisomatic Feedback Inhibition Underlies Cholinergically Induced Fast Network Oscillations in the Rat Hippocampus in Vitro," Neuron (2005), 45:105-117.
Mattis et al., "Principles for applying optogenetic tools derived from direct comparative analysis of microbial opsins", Nat Methods (2011), 9(2):159-72.
Mattson, "Apoptosis in Neurodegenerative Disorders", Nature Reviews (2000), 1:120-129.
Mayberg et al., "Deep Brain Stimulation for Treatment-Resistant Depression," Focus (2008), 6(1):143-154.
Mayford et al., "Control of memory formation through regulated expression of CaMKII transgene", Science (1996), 274(5293):1678-1683.
McAllister, "Cellular and Molecular Mechanisms of Dendrite Growth", Cereb Cortex (2000), 10(10):963-973.
McKnight, "Functional relationships between transcriptional control signals of the thymidine kinase gene of herpes simplex virus", Cell (1982), 31:355-365.
Melyan et al., "Addition of human melanopsin renders mammalian cells Photoresponsive", Nature (2005), 433:741-745.
Mermelstein et al., "Critical Dependence of cAMP Response Element-Binding Protein Phosphorylation on L-Type Calcium Channels Supports a Selective Response to EPSPs in Preference to Action Potentials", The Journal of Neuroscience (2000), 20(1):266-273.

Meyer et al., "High density interconnects and flexible hybrid assemblies for active biomedical implants," IEEE Transactions on Advanced Packaging (2001), 24(3):366-372.
Milella et al., "Opposite roles of dopamine and orexin in quinpirole-induced excessive drinking: a rat model of psychotic polydipsia", Psychopharmacology (2010), 211:355-366.
Monje et al., "Irradiation Induces Neural Precursor-Cell Dysfunction", Natural Medicine (2002), 8(9):955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology (1999), 80:571-583.
Mortensen et al., "Selection of Transfected Mammalian Cells," Supplement 86, Current Protocols in Molecular Biology (1997), 9.5.1-09.5.19.
Mourot et al., "Rapid Optical Control of Nociception with an Ion Channel Photoswitch", Nat Methods (2012), 9(4):396-402.
Nacher, et al., "NMDA receptor antagonist treatment increases the production of newneurons in the aged rat hippocampus", Neurobiology of Aging (2003), 24(2):273-84.
Nagel et al., "Functional Expression of Bacteriorhodopsin in Oocytes Allows Direct Measurement of Voltage Dependence of Light Induced H+ Pumping," FEBS Letters (1995), 377:263-266.
Nagel et al., "Channelrhodopsin-I: a light-gated proton channel in green algae", Science (2002), 296:2395-2398.
Nagel et al., "Channelrhodopsin-2, a directly light-gated cation-selective membrane channel", PNAS (2003), 100(24):13940-13945.
Nakagami et al., "Optical Recording of Trisynaptic Pathway in Rat Hippocampal Slices with a Voltage-Sensitive Dye", Neuroscience (1997), 81(1):1-8.
Naqvi et al., "Damage to the insula disrupts addiction to cigarette smoking," Science (2007), 315:531-534.
Natochin et al., "Probing rhodopsin-transducin interaction using Drosophila Rh1-bovine rhodopsin chimeras," Vision Res. (2006), 46(27):4575-81.
Nieh et al., "Optogenetic dissection of neural circuits underlying emotional valence and motivated behaviors", Brain Research (E-pub 2012), 1511:73-92.
Niren Berg et al., "The Light Response of Retinal Ganglion Cells is Truncated by a Displaced Amacrine Circuit", Neuron (1997), 18:637-650.
Nonet, "Visualization of synaptic specializations in live C. elegans with synaptic vesicle protein-GFP fusions", J. Neurosci. Methods (1999), 89:33-40.
Nunes-Duby et al., "Similarities and differences among 105 members of the Int family of site-specific recombinases", Nucleic Acids Research (1998), 26(2):391-406.
O'Gorman et al., "Recombinase-mediated gene activation and site-specific integration in mammalian cells", Science (1991), 251(4999):1351-1355.
Olivares, "Phage R4 integrase mediates site-specific integration in human cells", Gene (2001), 278:167-176.
Ory et al., "A stable human-derived packaging cell line for production of high titer retrovirus/vesicular stomatitis virus G pseudotypes," PNAS (1996), 93:11400-11406.
Palmer et al., "The Adult Rat Hippocampus Contains Primordial Neural Stem Cells", Molecular and Cellular Neuroscience (1997), 8:389-404.
Palmer et al., "Fibroblast Growth Factor-2 Activates a Latent Neurogenic Program in Neural Stem Cells from Diverse Regions of the Adult CNS", The Journal of Neuroscience (1999), 19:8487-8497.
Pan et al., "Functional Expression of a Directly Light-Gated Membrane Channel in Mammalian Retinal Neurons: A Potential Strategy for Restoring Light Sensitivity to the Retina After Photoreceptor Degeneration," Investigative Ophthalmology & Visual Science (2005), 46 E-Abstract 4631. Abstract only.
Panda et al., "Illumination of the Melanopsin Signaling Pathway", Science (2005), 307:600-604.

(56) References Cited

OTHER PUBLICATIONS

Pape et al., "Plastic Synaptic Networks of the Amygdala for the Acquisition, Expression, and Extinction of Conditioned Fear", Physiol. Rev. (2010), 90:419-463.
Paulhe et al., "Specific Endoplasmic Reticulum Export Signal Drives Transport of Stem Cell Factor (Kitl) to the Cell Surface," The Journal of Biological Chemistry (2004), 279(53):55545-55555.
Pear, "Transient Transfection Methods for Preparation of High-Titer Retroviral Supernatants" Supplement 68, Current Protocols in Molecular Biology (1996), 9.11.I1-9.11.I8.
Peralvarez-Marin et al., "Inter-helical hydrogen bonds are essential elements for intra-protein signal transduction: The role of Asp115 in bacteriorhodopsin transport function", J. Mol. Biol. (2007), 368:666-676.
Peterlin et al., "Optical probing of neuronal circuits with calcium indicators," PNAS (2000), 97(7):3619-3624.
Petersen et al., "Spatiotemporal Dynamics of Sensory Responses in Layer 2/3 of Rat Barrel Cortex Measured in Vivo by Voltage-Sensitive Dye Imaging Combined with Whole-Cell Voltage Recordings and Neuron Reconstructions," The Journal of Neuroscience (2003), 23(3):1298-1309.
Petrecca et al., "Localization and Enhanced Current Density of the Kv4.2 Potassium Channel by Interaction with the Actin-Binding Protein Filamin," The Journal of Neuroscience (2000), 20(23):8736-8744.
Pettit et al., "Local Excitatory Circuits in the Intermediate Gray Layer of the Superior Colliculus", J Neurophysiol. (1999), 81(3):1424-1427.
Pinkham et al., "Neural bases for impaired social cognition in schizophrenia and autism spectrum disorders", Schizophrenia Research (2008), 99:164-175.
Potter, "Transfection by Electroporation." Supplement 62, Current Protocols in Molecular Biology (1996), 9.3.1-9.3.6.
Pouille et al., "Routing of spike series by dynamic circuits in the hippocampus", Nature (2004), 429:717-723.
Qiu et al., "Induction of photosensitivity by heterologous expression of melanopsin", Nature (2005), 433:745-749.
Rammes et al., "Synaptic Plasticity in the Basolateral Amygdala in Transgenic Mice Expressing Dominant-Negative cAMP Response Element-binding Protein (CREB) in Forebrain", Eur J. Neurosci (2000), 12(7):2534-46.
Randic et al., "Long-term Potentiation and Long-term Depression of Primary Afferent Neurotransmission in the Rat Spinal Cord", Journal of Neuroscience, (1993), 13(12):5228-41.
Rathnasingham et al., "Characterization of implantable microfabricated fluid delivery devices," IEEE Transactions on Biomedical Engineering (2004), 51(1):138-145.
Rein et al., "The Optogenetic (r)evolution", Mol. Genet. Genomics (2012), 287(2):95-109.
Remy et al., "Depression in Parkinson's Disease: Loss of Dopamine and Noradrenaline Innervation in the Limbic System", Brain (2005), 128(6):1314-1322.
Ritter et al., "Monitoring Light-induced Structural Changes of Channelrhodopsin-2 by UV-Visible and Fourier Transform Infrared Spectroscopy", The Journal of Biological Chemistry (2008), 283(50):35033-35041.
Rivera et al., "BDNF-Induced TrkB Activation Down-Regulates the K+-Cl− cotransporter KCC2 and Impairs Neuronal Cl− Extrusion", The Journal of Cell Biology (2002), 159:747-752.
Rosenkranz et al., "The prefrontal cortex regulates lateral amygdala neuronal plasticity and responses to previously conditioned stimuli", J. Neurosci. (2003), 23(35):11054-11064.
Rousche et al., "Flexible polyimide-based intracortical electrode arrays with bioactive capability," IEEE Transactions on Biomedical Engineering (2001), 48(3):361-371.
Rubinson et at., "A lentivirus-based system to functionally silence genes in primary mammalian cells, stem cells and transgenic mice by RNA interference," Nature Genetics (2003), 33:401-406.
Rudiger et at., "Specific arginine and threonine residues control anion binding and transport in the light-driven chloride pump halorhodopsin," The EMBO Journal (1997), 16(13):3813-3821.
Salzman et al., "Cortical microstimulation influences perceptual judgements of motion direction", Nature (1990), 346:174-177.
Sajdyk et al., "Excitatory Amino Acid Receptors in the Basolateral Amygdala Regulate Anxiety Responses in the Social Interaction Test", Brain Research (1997), 764:262-264.
Sato et al., "Role of Anion-binding Sites in cytoplasmic and extracellular channels of Natronomonas pharaonis halorhodopsin," Biochemistry (2005), 44:4775-4784.
Sauer, "Site-specific recombination: developments and applications," Current Opinion in Biotechnology (1994), 5(5):521-527.
Schiff et al., "Behavioral improvements with thalamic stimulation after severe traumatic brain injury," Nature (2007), 448:600-604.
Schlaepfer et al., "Deep Brain stimulation to Reward Circuitry Alleviates Anhedonia in Refractory Major Depression," Neuropsychopharmacology (2008), 33:368-377.
Schroll et al., "Light-induced activation of distinct modulatory neurons triggers appetitive or aversive learning in drosophila larvae", Current Biology (2006), 16(17):1741-1747.
Sclimenti et al., "Directed evolution of a recombinase for improved genomic integration at a native human sequence," Nucleic Acids Research (2001), 29(24):5044-5051.
Shepherd et al., "Circuit Analysis of Experience-Dependent Plasticity in the Developing Rat Barrel Cortex", Neuron (2003), 38:277-289.
Silver et al., "Amino terminus of the yeast GAL4 gene product is sufficient for nuclear localization" PNAS (1984), 81(19):5951-5955.
Simmons et al., "Localization and function of NK3 subtype Tachykinin receptors of layer pyramidal neurons of the guinea-pig medial prefrontal cortex", Neuroscience (2008), 156(4):987-994.
Sineshchekov et al., "Two Rhodopsins Mediate Phototaxis to Low and High Intensity Light in Chlamydomas Reinhardtil", PNAS (2002), 99(13):8689-94.
Singer et al., "Elevated Intrasynaptic Dopamine Release in Tourette's Syndrome Measured by PET," American Journal of Psychiatry (2002), 159:1329-1336.
Slamovits et al., "A bacterial proteorhodopsin proton pump in marie eukaryotes", Nature Comm (2011), 2:183.
Slimko et al., "Selective Electrical Silencing of Mammalian Neurons in Vitro by the use of Invertebrate Ligand-Gated Chloride Channels", The Journal of Neuroscience (2002), 22(17):7373-7379.
Smith et al., "Diversity in the serine recombinases", Molecular Microbiology (2002) 44(2):299-307.
Sohal et al., "Parvalbumin neurons and gamma rhythms enhance cortical circuit performance", Nature (2009), 459(7247):698-702.
Song et al., "Differential Effect of TEA on Long-Term Synaptic Modification in Hippocampal CA1 and Dentate Gyrus in vitro." Neurobiology of Learning and Memory (2001), 76(3):375-387.
Song, "Genes responsible for native depolarization-activated K+ currents in neurons," Neuroscience Research (2002), 42:7-14.
Stark et al., "Catalysis by site-specific recombinases," Trends Genet. (1992), 8(12):432-439.
Stockklausner et al., "A sequence motif responsible for ER export and surface expression of Kir2.0 inward rectifier K+ channels," FEBS Letters (2001), 493:129-133.
Stoll et al., "Phage TP901-I site-specific integrase functions in human cells," Journal of Bacteriology (2002), 184(13):3657-3663.
Swanson, "Lights, Opsins, Action! Optogenetics Brings Complex Neuronal Circuits into Sharper Focus", The Dana Foundation (2009), [URL: http://www.dana.org/news/features/detail.aspx?id=24236], PDF File, pp. 1-3.
Swiss-Prot_Q2QCJ4, Opsin 1, Oct. 31, 2006, URL:http://www.ncbi.nlm.nig.gov/protein/Q2QCJ4.
The Nervous System in Action, Synapses, Chapter 13, http://michaeldmann.net/mann13.html, downloaded Apr. 2014.
Tamai, "Progress in Pathogenesis and Therapeutic Research in Retinitis Pigmentosa and Age Related Macular Degeneration", Nippon Ganka Gakkai Zasshi (2004), 108(12):750-769.

(56) References Cited

OTHER PUBLICATIONS

Tam et al., "Identification of an Outer Segment Targeting Signal in the Coon Terminus of Rhodopsin Using Transgenic *Xenopus laevis*", The Journal of Cell Biology (2000), 151(7):1369-1380.
Takahashi et al., "Diversion of the Sign of Phototaxis in a *Chlamydomonas reinhardtii* Mutant Incorporated with Retinal and Its Analogs," FEBS Letters (1992), 314(3):275-279.
Takahashi et al., "Induction of Pluripotent Stem Cells from Mouse Embryonic and Adult Fibroblast Cultures by Defined Factors", Cell (2006), 126:663-676.
Tatarkiewicz et al., "Reversal of Hyperglycemia in Mice After Subcutaneous Transplantation of Macroencapsulated Islets", Transplantation (1999), 67(5):665-671.
Tonnesen et al., "Optogenetic Control of Epileptiform Activity", PNAS (2009), 106(29):12162-7.
Tottene et al., "Familial Hemiplegic Migraine Mutations Increase $Ca^{2+}$ Influx Through Single Human $Ca_v2.1$ Current Density in Neurons", PNAS USA (2002), 99(20):13284-13289.
Towne et al., "Efficient transduction of non-human primate motor neurons after intramuscular delivery of recombinant AAV serotype 6", Gene Ther. (2010), 17(1):141-6.
Towne et al., "Optogenetic control of targeted peripheral axons in freely moving animals", PLoS One (2013), 8(8):e72691.
Towne et al., "Recombinant adeno-associated virus serotype 6 (rAAV2/6)-mediated gene transfer to nociceptive neurons through different routes of delivery", Mol. Pain (2009), 5:52.
Tsau et al., "Distributed Aspects of the Response to Siphon Touch in Aplysia: Spread of Stimulus Information and Cross-Correlation Analysis," The Journal of Neuroscience (1994), 14(7):4167-4184.
Tsai et al., "Phasic Firing in Dopaminergic Neurons in Sufficient for Behavioral Conditioning", Science (2009), 324:1080-1084.
[No Authors Listed], "Two bright new faces in gene therapy," Nature Biotechnology (1996), vol. 14:556.
Tye et. al., "Amygdala circuitry mediating reversible and bidirectional control of anxiety", Nature (2011), 471(7338): pp. 358-362.
Tye et al., "Optogenetic investigation of neural circuits underlying brain disease in animal models," Nature Reviews Neuroscience (2012), 13(4):251-266.
Tye et al., Supplementary Materials: "Amygdala circuitry mediating reversible and bidirectional control of anxiety", Nature (2011), 471(7338):358-362.
"SubName: Full=Channelrhodopsin-1", retrieved from EBI accession No. UNIPROT: B4Y103. Database accession No. B4Y103. Sep. 23, 2008.
Ulmanen et al., "Transcription and translation of foreign genes in *Bacillus subtilis* by the aid of a secretion vector," Journal of Bacteriology (1985), 162(1):176-182.
Van Der Linden, "Functional brain imaging and pharmacotherapy in social phobia: single photon emission computed tomography before and after Treatment with the selective serotonin reuptake inhibitor citalopram," Prog. Neuro-psychopharmacol Biol. Psychiatry (2000), 24(3):419-38.
Vanin, et al., "Development of high-titer retroviral producer cell lines by using Cre-mediated recombination," Journal of Virology (1997), 71(10):7820-7826.
Varo et al.," Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Vetter et al., "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. (2007), 9:I9.I-19.39.
Ward et al., "Construction and characterisation of a series of multi-copy promoter-probe plasmid vectors for *Streptomyces* using the aminoglycoside phosphotransferase gene from Tn5 as indicator", Mol. Gen. Genet. (1986), 203:468-478.

Watson et al., "Targeted transduction patterns in the mouse brain by lentivirus vectors pseudotyped with VSV, Ebola, Mokola, LCMV, or MuLV envelope proteins," Molecular Therapy (2002), 5(5):528-537.
Wang et al., "Direct-current Nanogenerator Driven by Ultrasonic Waves," Science (2007), 316:102-105.
Wang et al., "Molecular Determinants Differentiating Photocurrent Properties of Two Channelrhodopsins from Chlamydomonas", The Journal of Biological Chemistry (2009), 284(9):5685-5696.
Wang et. al., "High-speed mapping of synaptic connectivity using photostimulation in Channelrhodopsin-2 transgenic mice", PNAS (2007) 104(19):8143-8148.
Wang et al., "Mrgprd-Expressing Polymodal Nociceptive Neurons Innervate Most Known Classes of Substantia Gelatinosa Neurons", J Neurosci (2009), 29(42):13202-13209.
Weick et al., "Interactions with PDZ Proteins Are Required for L-Type Calcium Channels to Activate cAMP Response Element-Binding Protein-Dependent Gene Expression," The Journal of Neuroscience (2003), 23(8):3446-3456.
Wells et al., "Application of Infrared light for in vivo neural stimulation," Journal of Biomedical Optics (2005), 10(6):064003-1-064003-12.
Williams et al., "From optogenetic technologies to neuromodulation therapies", Sci Transl Med. (2013), 5(177):177.
Witten et. al., Supporting Online Material for: "Cholinergic Interneurons Control Local Circuit Activity and Cocaine Conditioning", Science (2010), 330:17 pages.
Witten et. al., "Cholinergic Interneurons Control Local Circuit Activity and Cocaine Conditioning", Science (2010), 330(6011):1677-1681.
Xiong et al., "Interregional connectivity to primary motor cortex revealed using MRI resting state images", Hum Brain Mapp. (1999), 8(2-3):151-156.
Yamazoe et al., "Efficient generation of dopaminergic neurons from mouse embryonic stem cells enclosed in hollow fibers", Biomaterials (2006), 27:4871-4880.
Yan et al., "Cloning and Characterization of a Human $\beta,\beta$-Carotene-15, 15'-Dioxygenase that is Highly Expressed in the Retinal Pigment Epithelium", Genomics (2001), 72:193-202.
Yizhar et al., "Optogenetics in neural systems", Neuron Primer (2011), 71(1):9-34.
Yizhar et. al., "Neocortical excitation/inhibition balance in information processing and social dysfunction", Nature (2011), 477:171-178, and Supplemental Materials; 41 pages.
Yoon et al., "A micromachined silicon depth probe for multichannel neural recording," IEEE Transactions Biomedical Engineering (2000), 47(8):1082-1087.
Yoshimura et al., "Excitatory cortical neurons form fine-scale functional networks", Nature (2005), 433:868-873.
Zacharias et al., "Recent advances in technology for measuring and manipulating cell signals," Current Opinion in Neurobiology (2000), 10:416-421.
Zemelman, et al. "Selective Photostimulation of Genetically ChARGed Neurons", Neuron (2002), 33:15-22.
Zemelman et al., "Photochemical gating of heterologous ion channels: Remote control over genetically designated populations of neurons", PNAS (2003), 100(3):1352-1357.
Zhang et al., "Channelrhodopsin-2 and optical control of excitable cells," Nature Methods (2006), 3(10):785-792.
Zhang et al., "Red-Shifted Optogenetic Excitation: a Tool for Fast Neural Control Derived from *Volvox carteri*", Nature Neurosciences (2008), 11(6):631-633.
Zhang, "Multimodal fast optical interrogation of neural circuitry," Nature (2007), 446:633-641.
Zhang et al., "The Microbial Opsin Family of Optogenetic Tools", Cell (2011), 147(7):1146-1457.
Zhao et al., "Improved Expression of Halorhodopsin for Light-Induced Silencing of Neuronal Activity", Brain Cell Biology (2008), 36 (1-4):141-154.
Zrenner, "Will Retinal Implants Restore Vision?" Science (2002), 295(5557):1022-1025.

(56) References Cited

OTHER PUBLICATIONS

Zufferey et al., "Self-Inactivating Lentivirus Vector for Safe and Efficient in Vivo Gene Delivery", Journal of Virology (1998), 72(12):9873-9880.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Jones, et al.; "Animal Models of Schizophrenia"; British Journal of Pharmacology; vol. 164, pp. 1162-1194 (2011).
Adinoff; "Neurobiologic Processes in Drug Reward and Addiction"; Harv. Rev. Psychiatry; vol. 12, No. 6, pp. 305-320 (2004).
Chow, et al.; "High-performance genetically targetable optical neural silencing by light-driven proton pumps"; Nature; vol. 463, pp. 98-102 (Jan. 7, 2010).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Rogers, et al.; "Effects of ventral and dorsal CA1 subregional lesions on trace fear conditioning"; Neurobiology of Learning and Memory; vol. 86, pp. 72-81 (2006).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).

Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No, 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Johnson, et al.; "Differential Biodistribution of Adenoviral Vector in Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Lammel, et al., "Input-Specific Control of Reward and Aversion in the Ventral Tegmental Area", Nature, Nov. 8, 2012, 491(7423): 212-217.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

(56) References Cited

OTHER PUBLICATIONS

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Cowan et al., "Targeting gene expression to endothelium in transgenic animals: a comparison of the human ICAM-2, PECAM-1, and endoglin promoters", Xenotransplantation, 2003, vol. 10, pp. 223-231.

Definition of Psychosis (2015).

Ebert et al., "A Moloney MLV-rat somatotropin fusion gene produces biologically active somatotropin in a transgenic pig", Mot. Endocrinology, 1988, vol. 2, pp. 277-283.

Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.

Karra, et al. "Transfection Techniques for Neuronal Cells", The Journal of Neuroscience, 2010, vol. 30, No. 18, pp. 6171-6177.

Kelder et al., "Glycoconjugates in human and transgenic animal milk", Advances in Exp. Med. And Biol., 2001, vol. 501, pp. 269-278.

Mullins et al., "Fulminant hypertension in transgenic rats harbouring the mouse *Ren*-2 gene", Nature, 1990, vol. 344, pp. 541-544.

Mullins et al., "Expression of the DBA/2J *Ren*-2 gene in the adrenal gland of transgenic mice", EMBO, 1989, vol. 8, pp. 4065-4072.

Taurog et al., "HLA-B27 in inbred and non-inbred transgenic mice", J. Immunol., 1988, vol. 141, pp. 4020-4023.

Wall, "Transgenic livestock: Progress and prospects for the future", Theriogenology, 1996, vol. 45, pp. 57-68.

Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.

Written opinion of PCT Application No. PCT/US2011/059383 (May 9, 2012).

\* cited by examiner

FIGURE 6A

INHIBITORY

The amino acid sequence of NpHR without the signal peptide:

VTQRELFEFVLNDPLLASSLYNLALAGLSILFVFMTRGLDDPRAKLIAVSTILVPVVSIASYTGLASGLTISVLEMPAGHFAEGSSVMLGGEEVDGVVTMWGRYLTWALSTPMILLALGLLAGSNATKLFTAITFDIAMCVTGLAALTSSHLMRWFWYAISCACFLVVLYILLVEWAQDAKAAGTADMFNTLKLLTVMWLGYPIVWALGVEGIAVLPVGVTSWGYSFLDIVAKYIFAFLLLNYLTSNESVVSGSILDVPSASGTPADD (SEQ ID NO:1).

The amino acid sequence of eYFP-NpHR3.0:

MTETLPPVTESAVALQAEVTQRELFEFVLNDPLLASSLYNLALAGLSILFVFMTRGLDDPRAKLIAVSTILVPVVSIASYTGLASGLTISVLEMPAGHFAEGSSVMLGGEEVDGVVTMWGRYLTWALSTPMILLALGLLAGSNATKLFTAITFDIAMCVTGLAALTSSHLMRWFWYAISCACFLVVLYILLVEWAQDAKAAGTADMFNTLKLLTVVMWLGYPIVWALGVEGIAVLPVGVTSWGYSFLDIVAKYFAFLLLNYLTSNESVVSGSILDVPSASGTPADDAAAKSRITSEGEYIPLDQIDNVVSKGEELFTGVVPILVELDGDVNGHKFSVSGEGEGDATYGKLTLKFICTTGKLPVPWPILVTTFGYGLQCFARYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSYQSALSKDPNEKRDHMVLLEFVTAAGITLGMDELYKFCYENEV (SEQ ID NO:2).

FIGURE 6B

INHIBITORY

The amino acid sequence of eYFP-NpHR3.1:

MVTQRELFEFVLNDPLLASSLYINIALAGLSILLFVFMTRGLDDDPRAKLIAVSTILVPVVSI
ASYTGLASGLTISVLEMPAGHFAEGSSVMLGGEEVDGVVTMWGRYLTWALSTPMILLA
LGLLAGSNATKLFTAIIFDIAMCVTGLAAALTSSHLMRWFWYAISCACFLVLYILLVE
WAQDAKAAGTADMFNTLKLLTVVMWLGYPIVWALGVEGIAVLPVGVTSWGYSFLDIV
AKYIFAFLLLNYLTSNESVVSGSILDVPSASGTPADDAAKSRITSEGEYIPLDQIDINVS
KGEELFTGVVPILVELDGDVNGHKFSVSGEGEGDATYGKLTLKFICTTGKLPVPWPTLVI
TFGYGLQCFARYPDHMKQHDFFKSAMPEGYVQERTIFFKDDGNYKTRAEVKFEGDTLV
NRIELKGIDFKEDGNLGHKLEYNYNSHNVYIMADKQKNGIKVNFKIRHNIEDGSVQLAD
HYQQNTPIGDGPVLLPDNHYLSYQSALSKDPNEKRDHMVLLEFVTAAGITLGMDELYKF
CYENEV (SEQ ID NO:3).

The amino acid sequence of GtR3:

ASSFGKALLEFVFIVFACITLLLGNAAKSKAASRVLFPATFVTGIASIAYFSMASGGGWVI
APDCRQLFVARYLDWLITPLLLIDLGLVAGVSRWDMALCLSDVLMIATGAFGSLTVG
NVKWVWFFGMCWFLHIIFALGKSWAEAAKAKGGDSASVYSKIAGITVIFWFCYPVV
WVFAEGFGNFSVIFEVLIYGVLDVISKAVFGLILMSGAATGYESI (SEQ ID NO:4).

FIGURE 6C

INHIBITORY

The amino acid sequence of eArch:

MDPIALQAGYDLLGDGRPETLWLGIGTLMLIGIFYFLVRGWGVTDKDAREYYAVTIL
VPGIASAAYLSMFFGIGLTEVTVGGEMLDIYYARYADWLFTPLLLDLALLAKVDRV
TIGTLVGVDALMIVTGLIGALSHTAIARYSWWLFSTICMIVLYFLATSLRSAAKERGPE
VASTFNTLTALVLWLWTAYPILWIIGTEGAGVVGLGIETLLFMVLDVTAKVGFGFILLR
SRAILGDTEAPEPSAGADVSAAD (SEQ ID NO:12).

The amino acid sequence of eArch3.0-EYFP:

MDPIALQAGYDLLGDGRPETLWLGIGTLMLIGIFYFLVRGWGVTDKDAREYYAVTIL
VPGIASAAYLSMFFGIGLTEVTVGGEMLDIYYARYADWLFTPLLLDLALLAKVDRV
TIGTLVGVDALMIVTGLIGALSHTAIARYSWWLFSTICMIVLYFLATSLRSAAKERGPE
VASTFNTLTALVLWLWTAYPILWIIGTEGAGVVGLGIETLLFMVLDVTAKVGFGFILLR
SRAILGDTEAPEPSAGADVSAADRPVVAVSKAAAKSRITSEGEYIPLDQIDNVSKGEE
LFTGVVPILVELDGDVNGHKFSVSGEGEGDATYGKLTLKFICTGKLPVPWPTLVTFG
YGLQCFARYPDHMKQHDFFKSAMPEGYVQERTIFFKDDGNYKTRAEVKFEGDTLVNR
IELKGIDFKEDGNILGHKLEYNYNSHNVYIMADKQKNGIKVNFKIRHNIEDGSVQLAD
HYQQNTPIGDGPVLLPDNHYLSYQSALSKDPNEKRDHMVLLEFVTAAGITLGMDELY
KFCYENEV (SEQ ID NO:13).

FIGURE 6D

INHIBITORY

ArchT 3.0

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLIGIETLLFMVLDVTAKVGFGFILLRSRAIL
GDTEAPEP (SEQ ID NO:14)

Mac 3.0

MIVDQFEEVLMKTSQLFPLPTATQSAQPTHVAPVPTVLPDTPIYETVGDSGSKTLWVFFV
LMLIASAAFTALSWKIPVNRRLYHVITTILTAALSYFAMATGHGVALNKIVIRTQHDH
VPDTYETVYRQVYARYIDWAITTPLLLDLGLLAGMSGAHIFMAIVADLIMVLTGLFAA
FGSEGTPQKWGWYTIACIAYIFVVWHLVLNGGANARVKGEKLRSFFVAIGAYTLIIWTAY
PIVWGLADGARKIGVDGEIIAYAVLDVLAKGVFGAWLLVTHANLRESDVELNGFWANGLN
REGAIRIGEDDGARPVVAVSK (SEQ ID NO:15)

FIGURE 6E

EXCITATORY

The amino acid sequence of ChR2:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEKNPSMLYLATGHRVQ
WLRYAEWLLTCPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:5)

The amino acid sequence of SFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEKNPSMLYLATGHRVQ
WLRYAEWLLTSPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:6)

FIGURE 6F

EXCITATORY

The amino acid sequence of SSFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEKNPSMLYLATGHRVQ
WLRYAEWLLTSPVILIHLSNLTGLSNDYSRRTMGLLVSAIGTIVWGATSAMATGYVKVIF
FCLGLCYGANTFHAAKAYIEGYHTVPKGRCRQVVIGMAWLFFVSWGMFPILFILGPEG
FGVLSVYGSTVGHTIIDLMSKNCWGLLGHYLRVLIHEHILIHGDIRKTKLNIGGTEIEVET
LVEDEAEAGAVP (SEQ ID NO:7).

The amino acid sequence of C1V1:

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYAEWLLTCPVLLIHL
SNLTGLKDDYSKRTMGLLVSDVGCIVWGATSAMCTGWTKILFFLISLSYGMTYFHA
AKVYIEAFHTVPKGICRELVRVMAWTFFVAWGMFPVLFLLGTEGFGHISPYGSAIGHSI
LDLLAKNMWGVLGNYLRVKIHEHILLYGDIRKKQKITIAGQEMEVETLVAEEED (SEQ
ID NO:8).

FIGURE 6G

EXCITATORY

The amino acid sequence of C1V1 (E122T):

MSRRPWLLALALAVALAAGSAGASTGSDATVPVATQDGPDYVFHRAHERMLFQTSYTL
ENNGSVICIPNNGQCFCLAWLKSNGTNAEKLAANILQWITFALSALCLMFYGYQTWKST
CGWEEIYVATIEMIKFIIEYFHEFDEPAVIYSSNGNKTVWLRYAEWLLTCPVLLIHLSNLT
GLKDDYSKRTMGLLVSDVGCIVWGATSAMCTGWTKILFFLISLSYGMYTYFHAAKVYIE
AFHTVPKGICRELVRVMAWTFFVAWGMFPVLFLLGTEGFGHISPYGSAIGHSILDLIAKN
MWGVLGNYLRVKIHEHILLYGDIRKKQKITIAGQEMEVETLVAEEED (SEQ ID NO:9).

The amino acid sequence of C1V1 (E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYATWLLTCPVLLIHL
SNLTGLKDDYSKRTMGLLVSDVGCIVWGATSAMCIGWIKILFFLISLSYGMYIYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED (SEQ
ID NO:10).

FIGURE 6H

EXCITATORY

The amino acid sequence of C1V1 (E122T/E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGQTW
KSTCGWEIIYVATIEMIKFIIEYFHEFDEPAVIYSSNGNKTVWLRYATWLLTCPVLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITLAGQEMEVETLVAEEED (SEQ
ID NO:11).

FIGURE 10
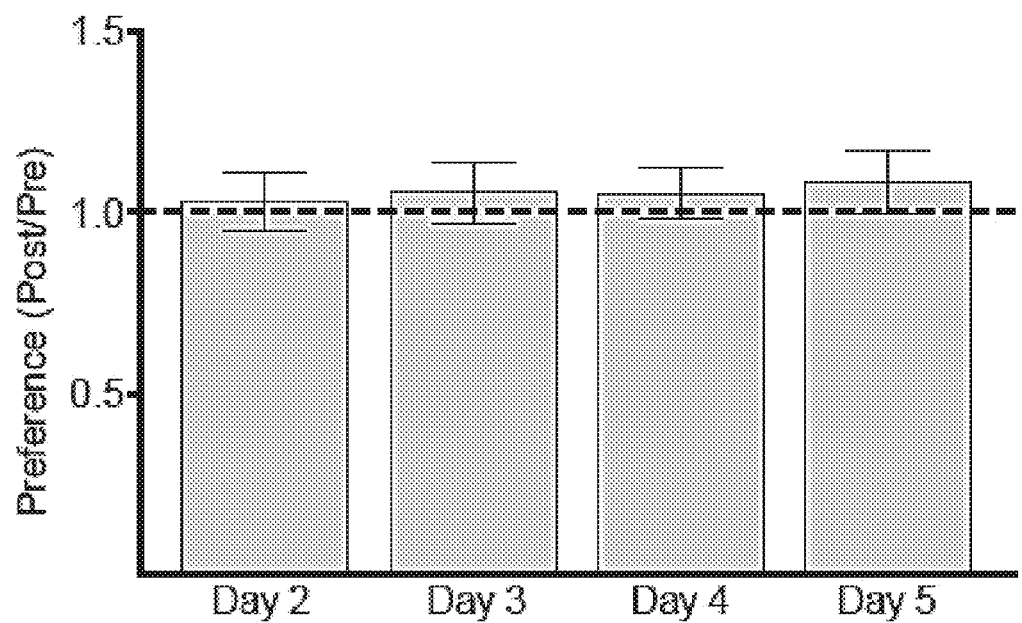

FIGURE 11A
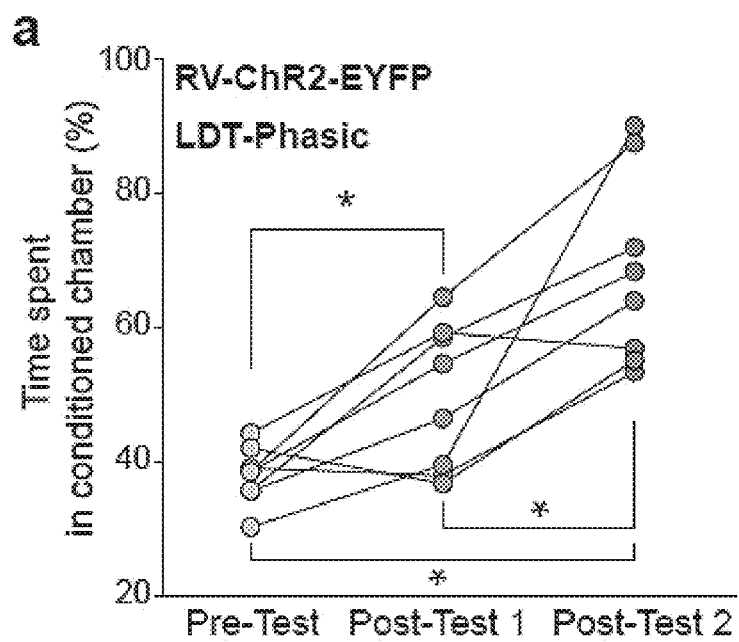
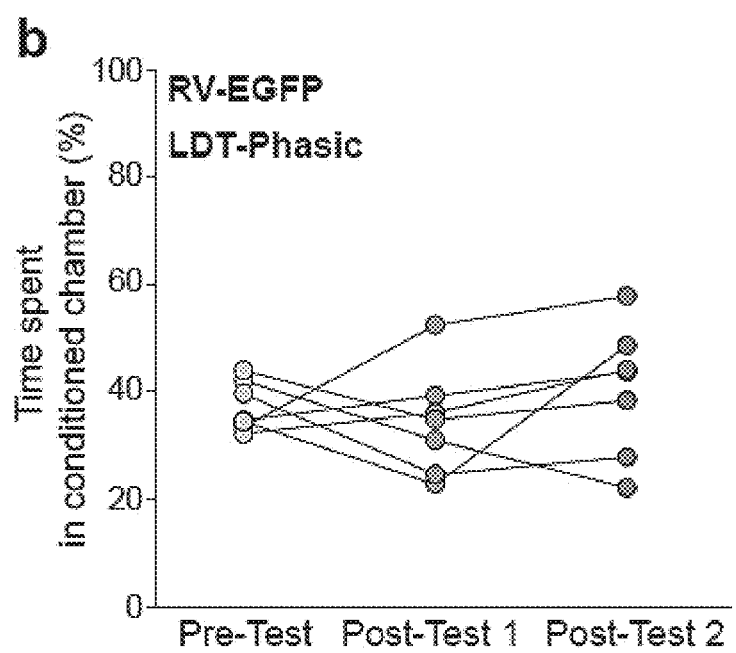

FIGURE 11B
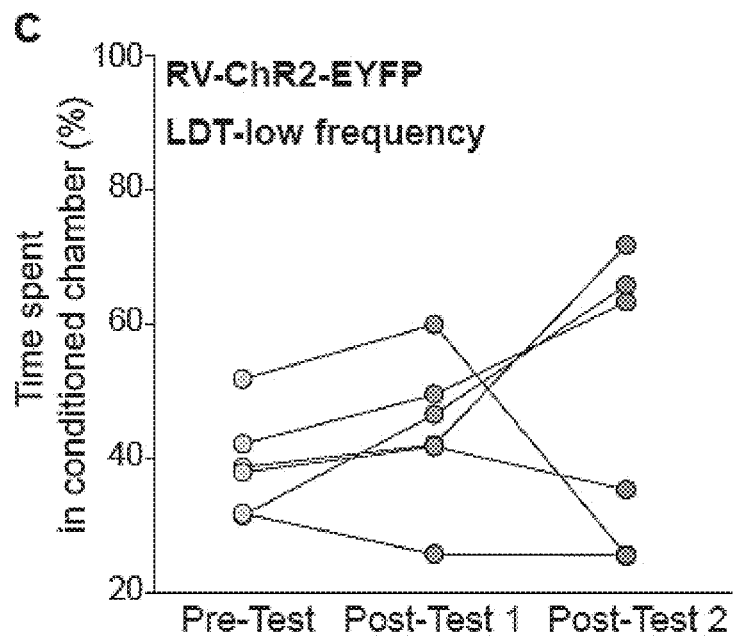
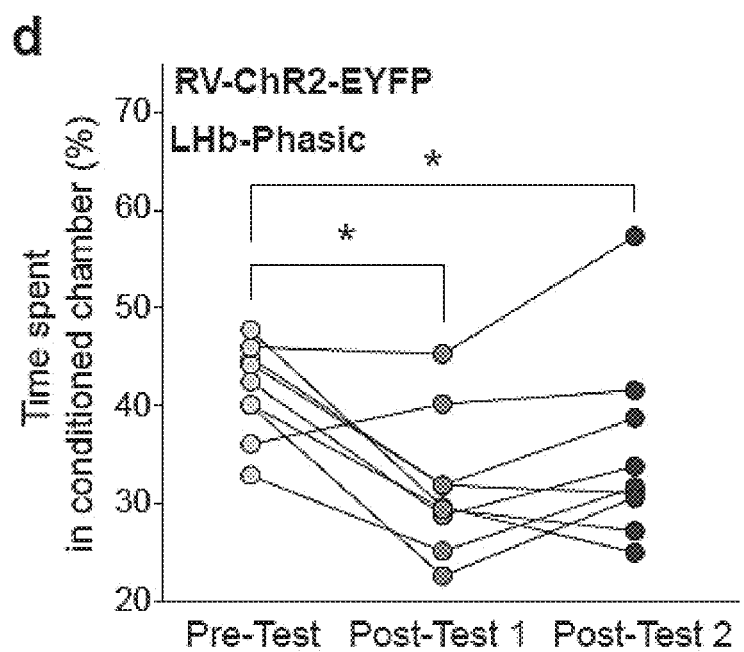

FIGURE 11C
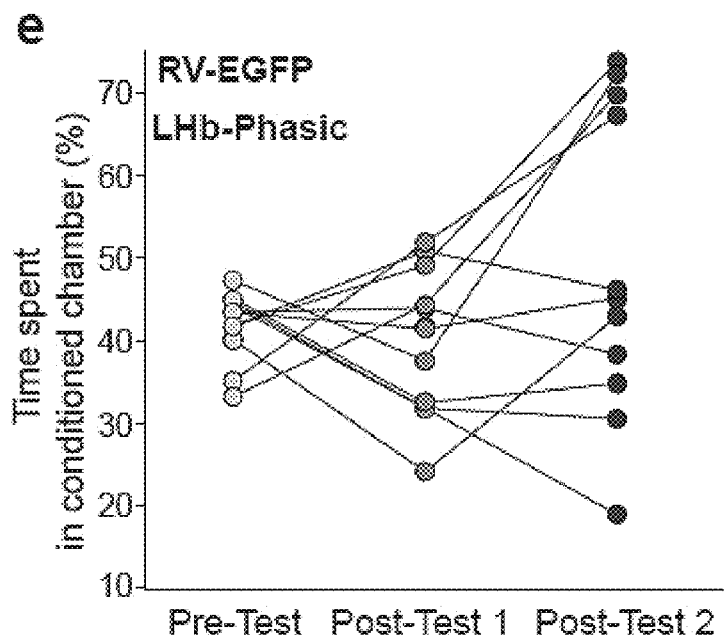
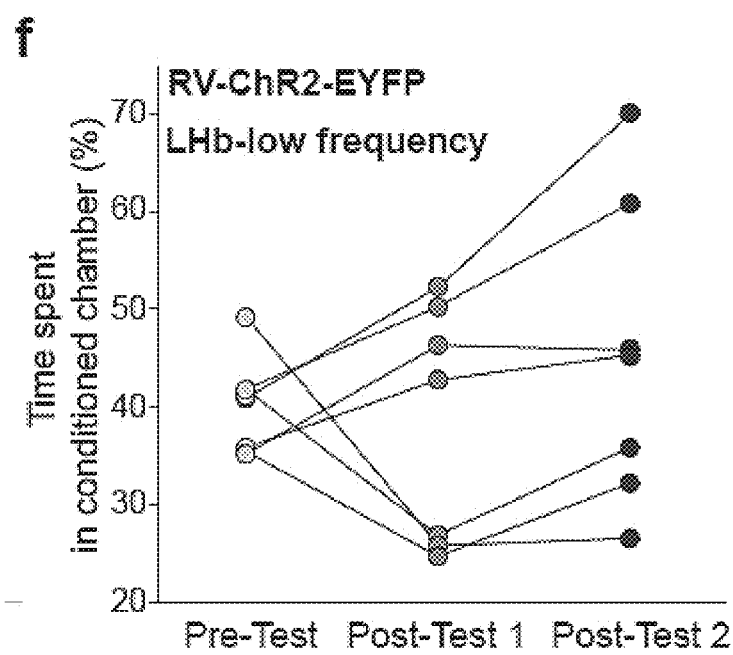

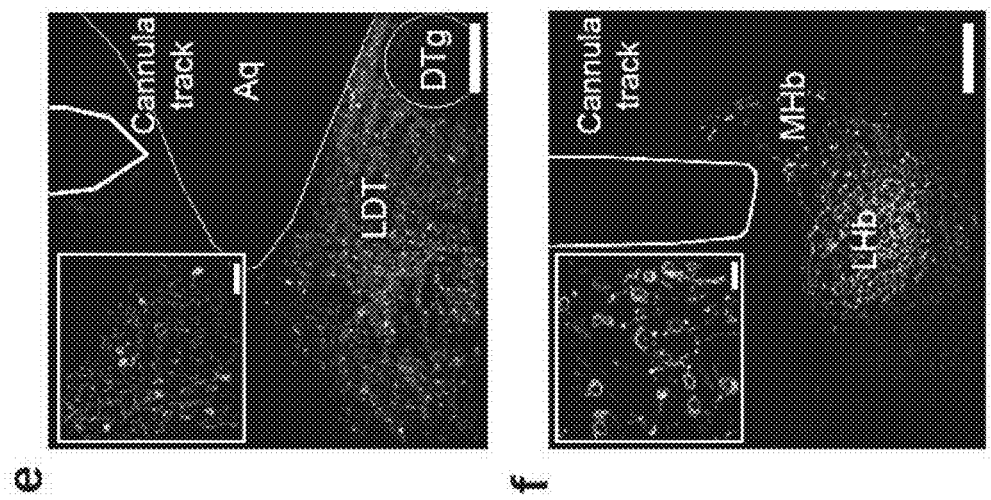

FIGURE 14D
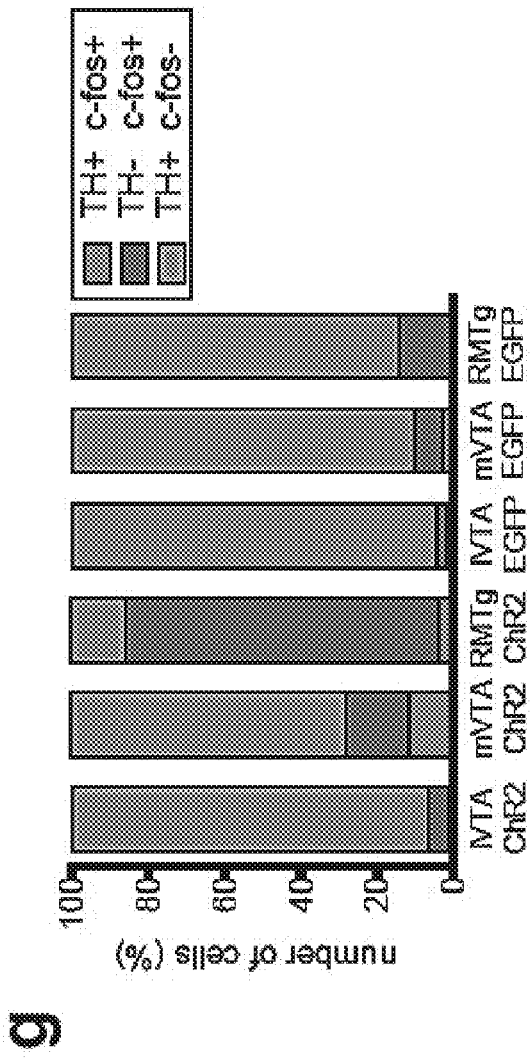
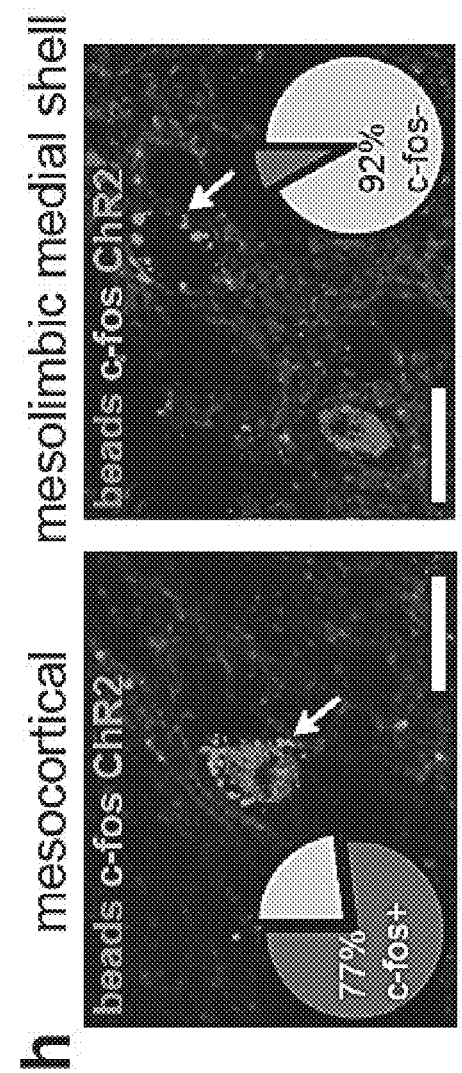

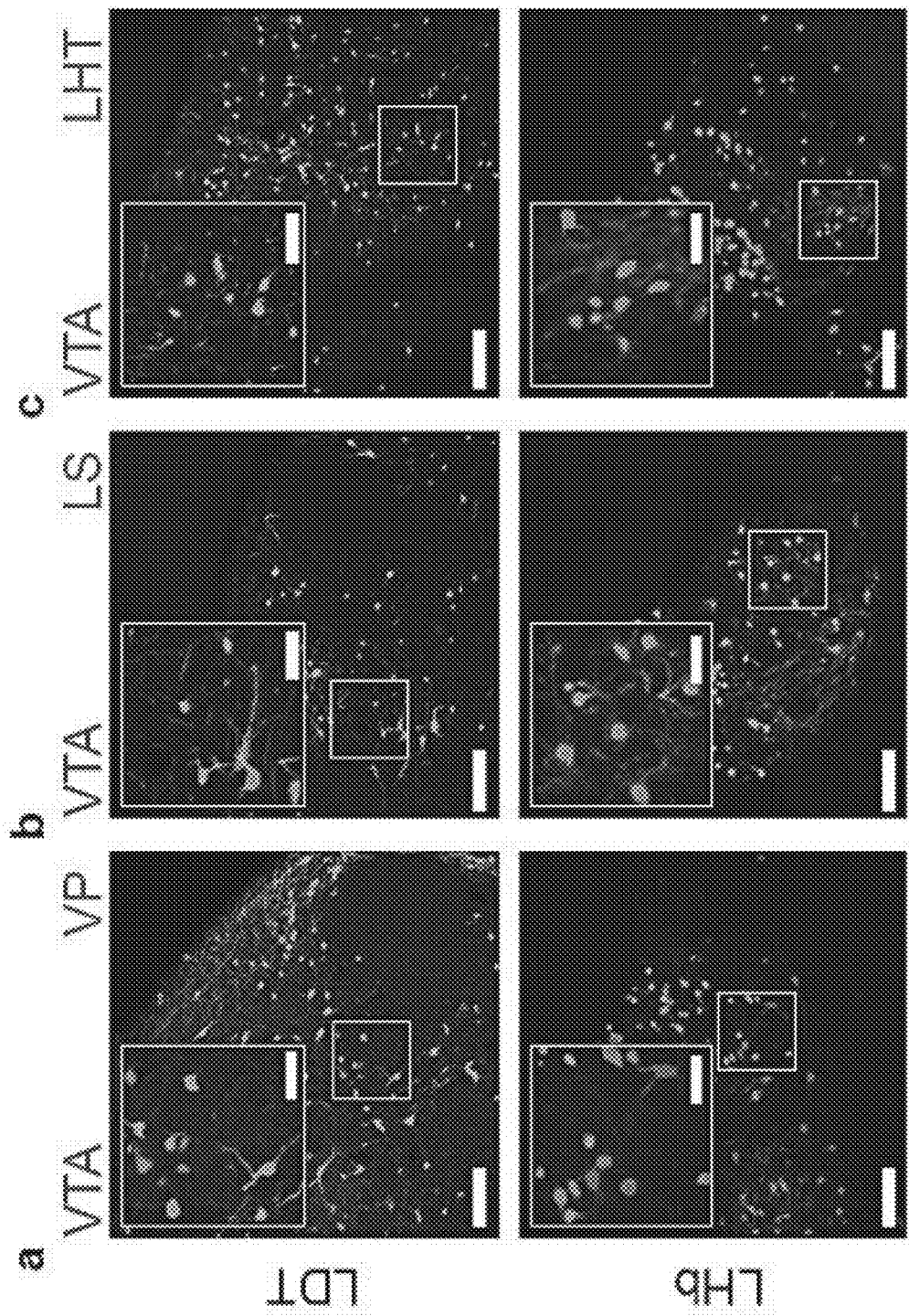

FIGURE 17C
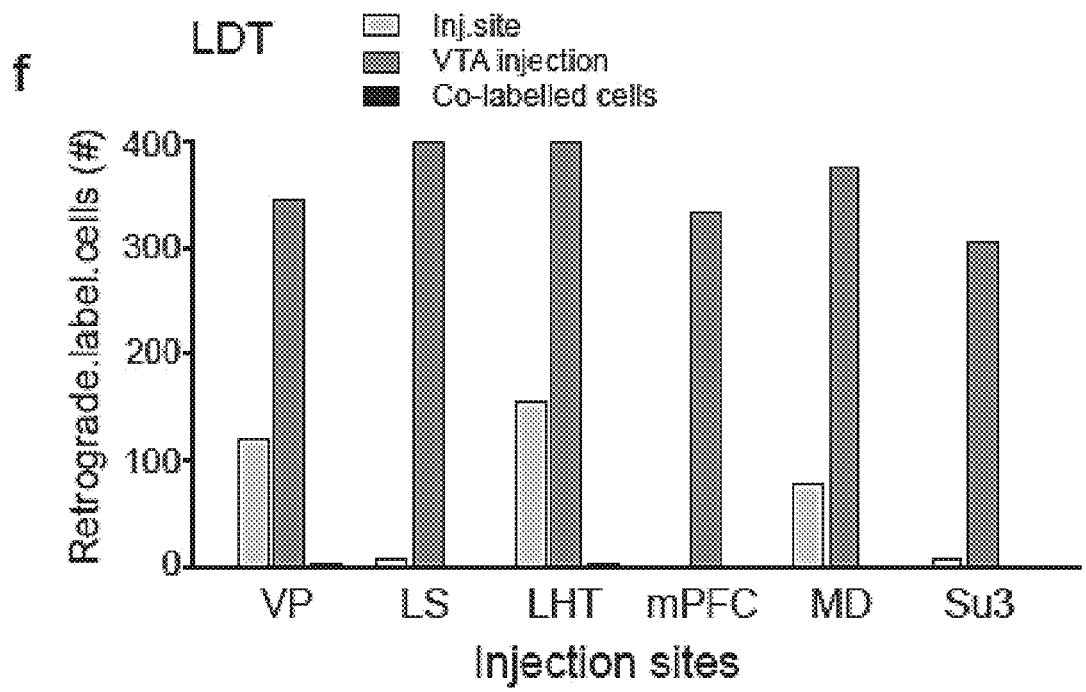
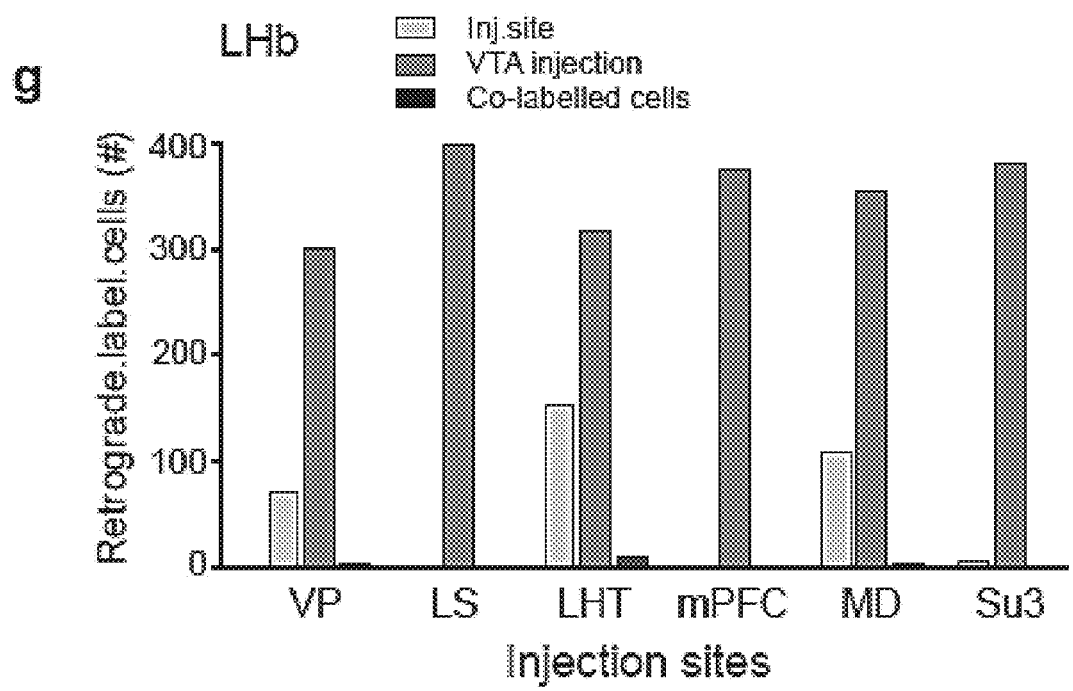

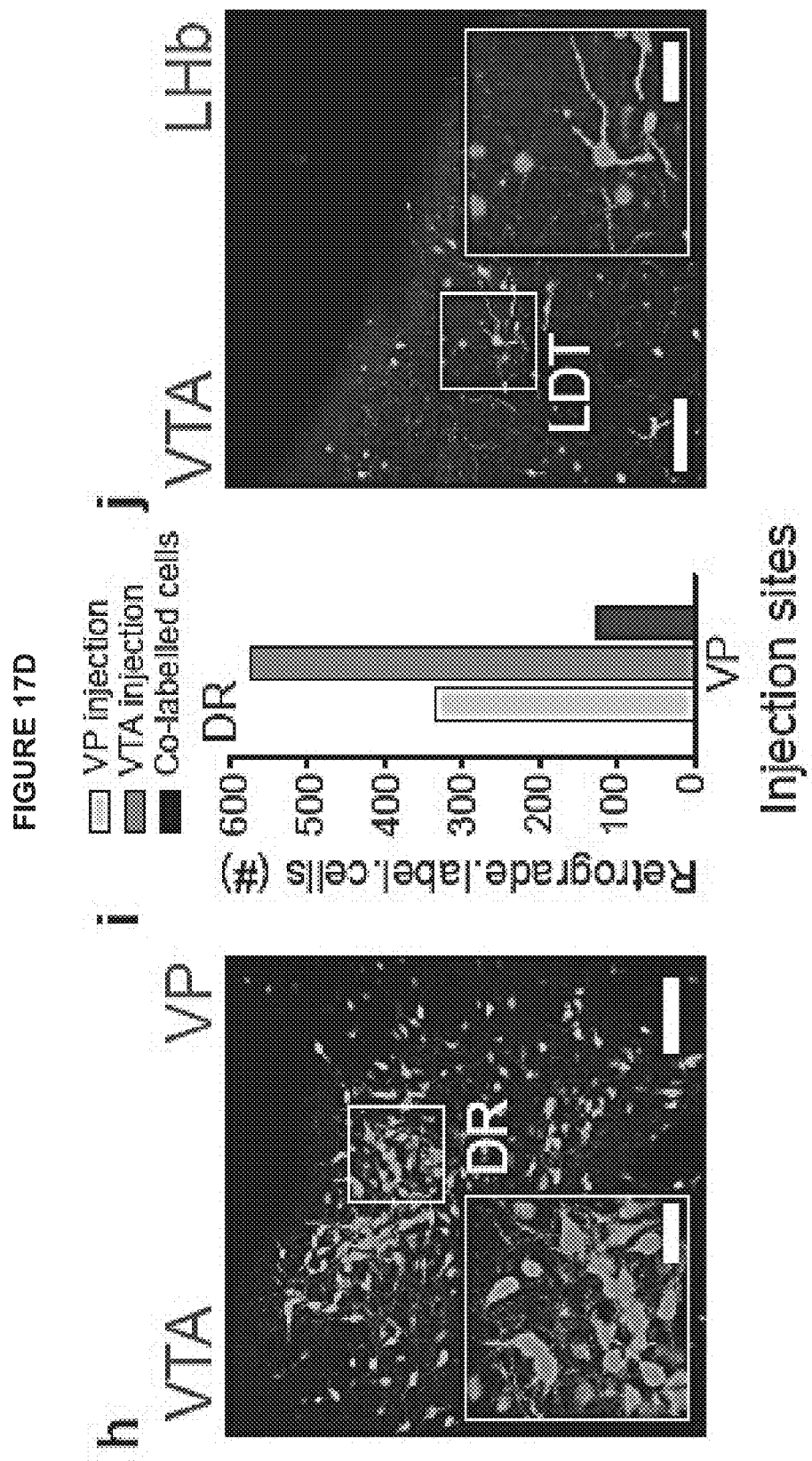

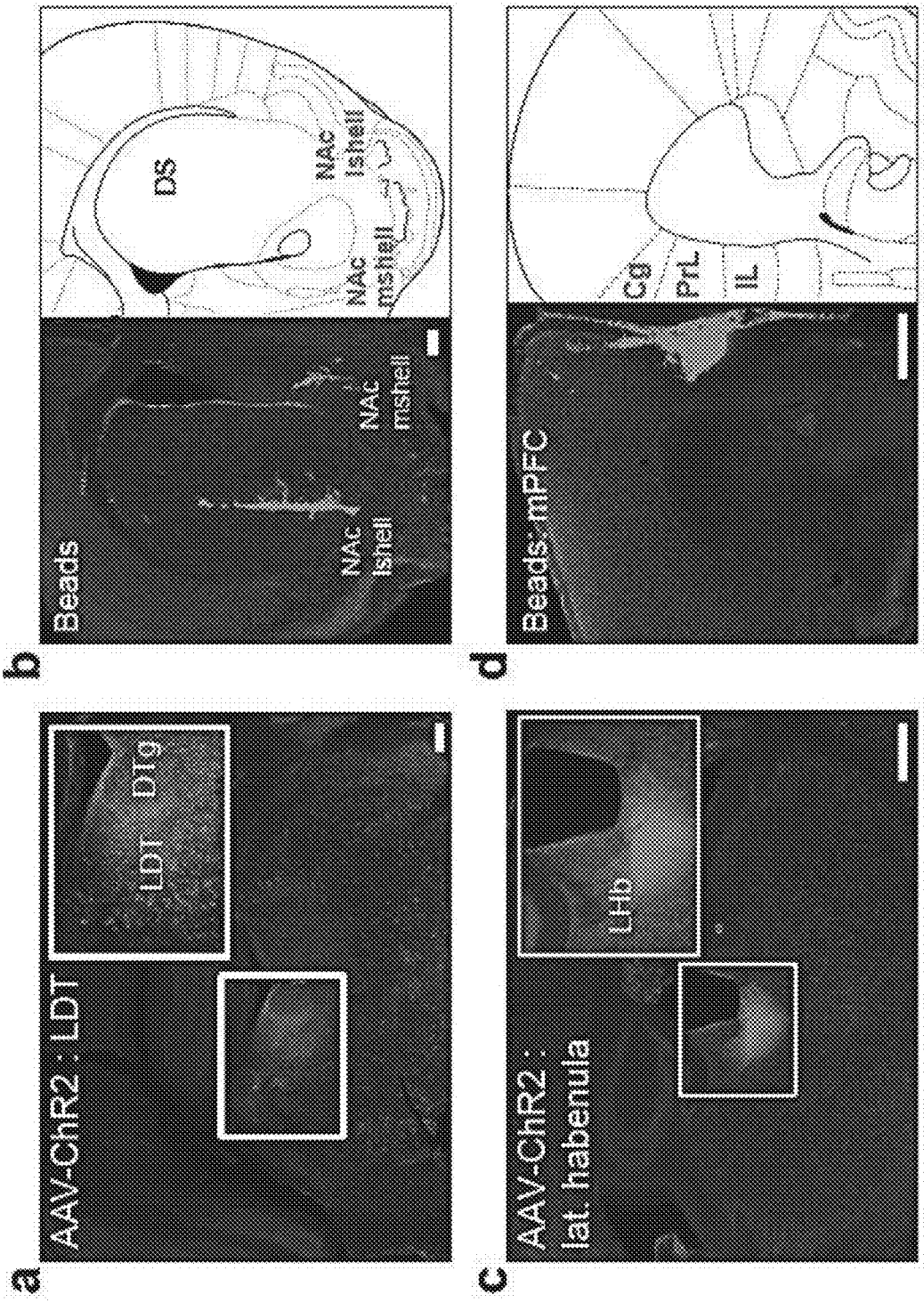

FIGURE 19C
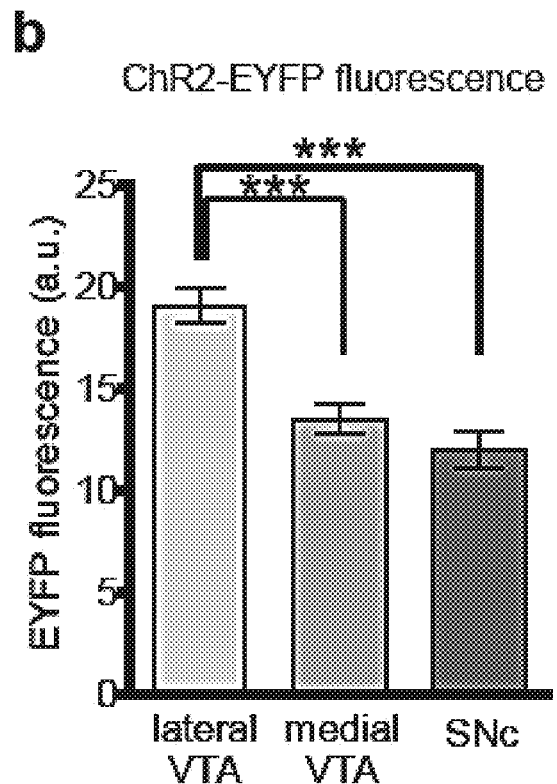
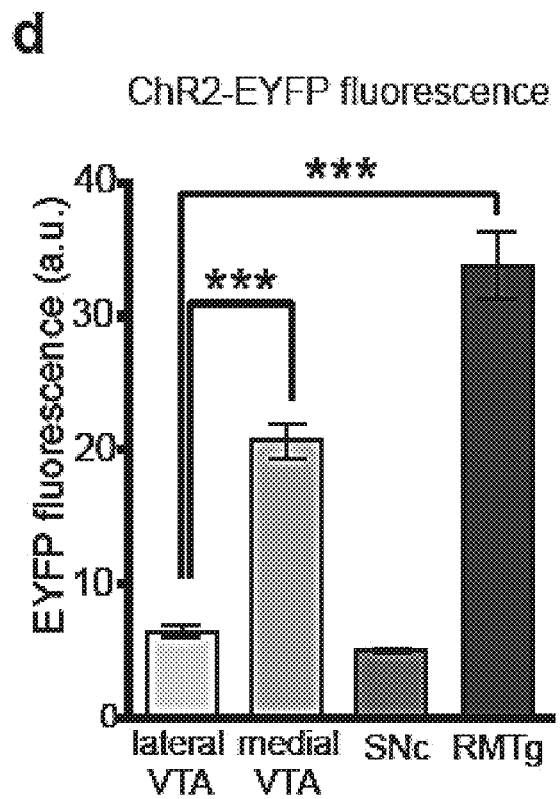

FIGURE 20A
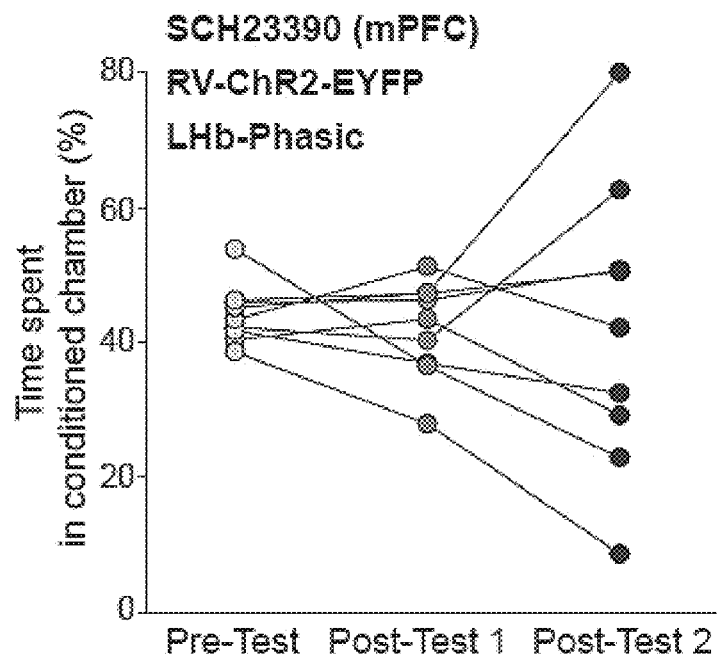
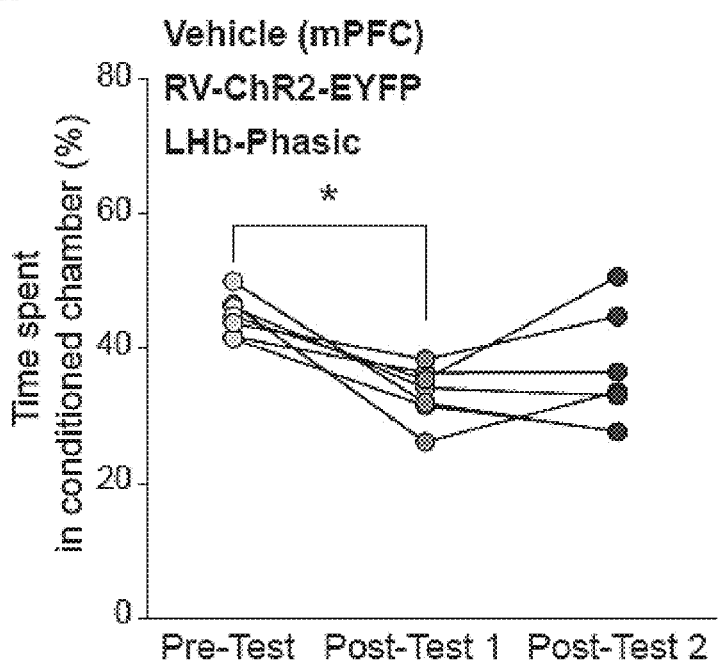

FIGURE 20B
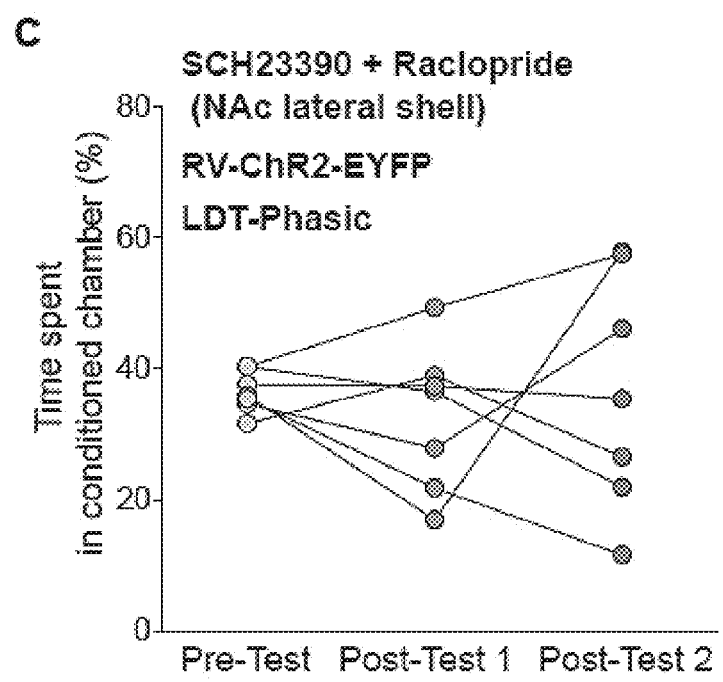
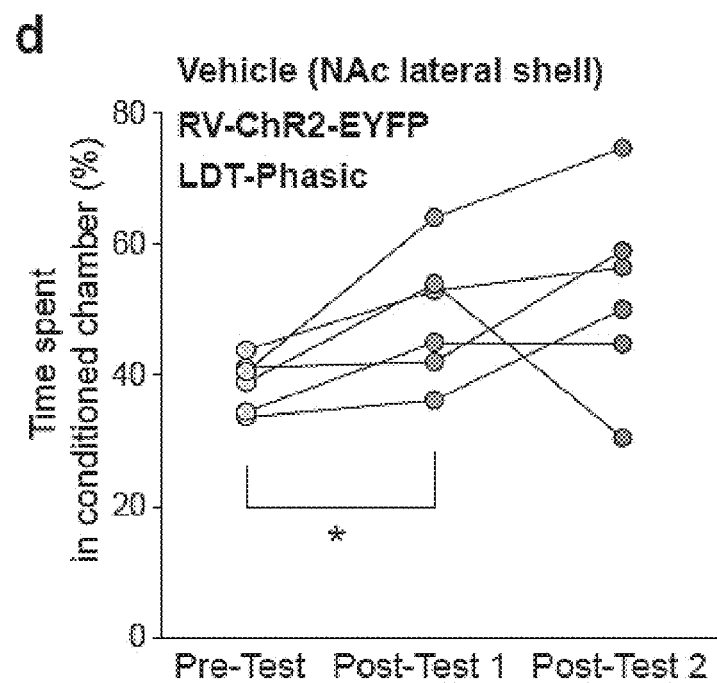

FIGURE 21B
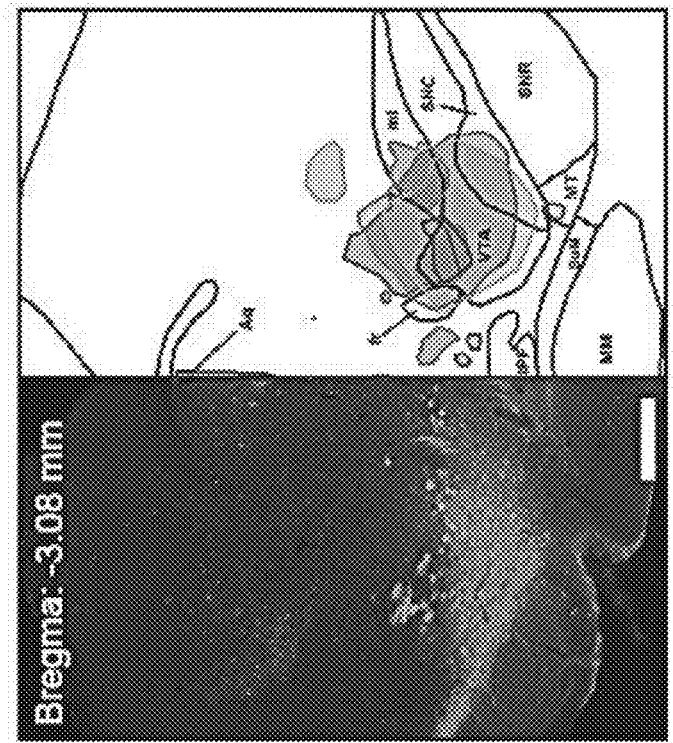
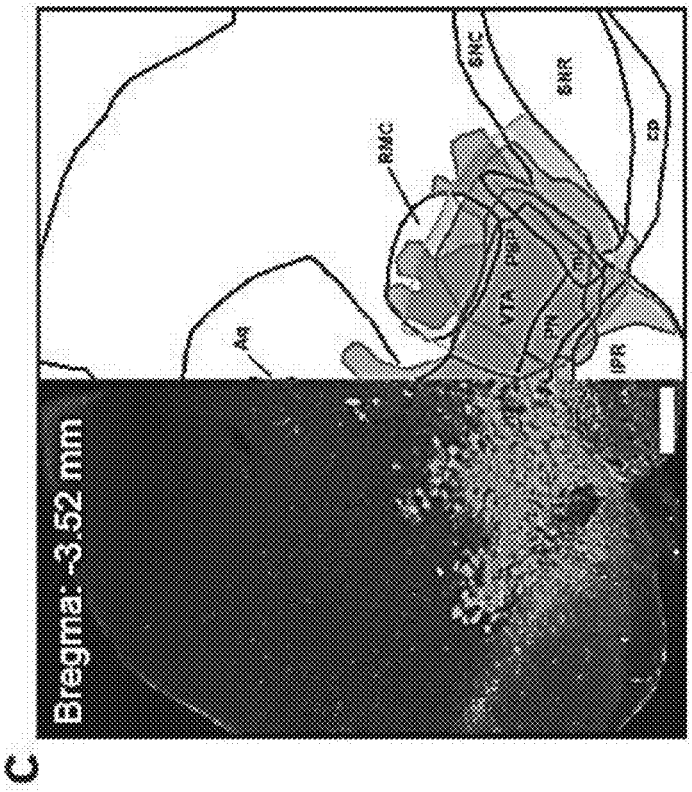

OPTOGENETIC CONTROL OF INPUTS TO THE VENTRAL TEGMENTAL AREA

CROSS-REFERENCE

This application claims the benefit of U.S. Provisional Patent Application Nos. 61/789,486, filed Mar. 15, 2013, and 61/890,000, filed Oct. 11, 2013, which applications are incorporated herein by reference in their entirety.

STATEMENT REGARDING FEDERALLY SPONSORED RESEARCH

This invention was made with Government support under contract MH086403 awarded by the National Institutes of Health. The Government has certain rights in the invention.

INCORPORATION BY REFERENCE OF SEQUENCE LISTING PROVIDED AS A TEXT FILE

A Sequence Listing is provided herewith as a text file, "STAN-1019 SeqList_ST25.txt" created on Mar. 12, 2014 and having a size of 50 KB. The contents of the text file are incorporated by reference herein in their entirety.

INTRODUCTION

The functional roles of VTA dopamine (DA) neurons have received great attention because they are the primary source of DA in target structures such as the medial prefrontal cortex (mPFC) and nucleus accumbens (NAc), which play important roles in a broad range of motivated behaviors and neuropsychiatric disorders[1-3]. Although DA neuron activity often correlates with a reward prediction error (i.e. the difference between expected and actual rewards) these cells also can signal aversion, saliency, uncertainty and novelty. They are heterogeneous in their anatomical location, targets to which they project, electrophysiological properties and several molecular features. In addition, the VTA receives both excitatory and inhibitory input from distributed brain areas. Thus different subpopulations of VTA DA and GABAergic neurons may subserve different functions but little is known about the afferent control of their activity and the circuits in which they are embedded.

SUMMARY

The present disclosure provides a method of inducing or modulating reward- or aversive-related behaviors in animals using light-responsive opsins. The present disclosure provides methods of identifying or screening compounds that may be used to treating mental disorders, or are relevant to disrupt or improve reward- or aversive related behaviors.

BRIEF DESCRIPTION OF THE DRAWINGS

FIGS. 6A-H provide amino acid sequences of various light-responsive proteins.

FIG. 10 depicts a schematic of the genome of the recombinant rabies virus expressing ChR2-EYFP, cells expressing the ChR2-EYFP, and control preference/avoidance for chambers of a preference/aversion assay.

FIGS. 11A-C depict various behavioral assays of mice injected with RV-ChR2-EYFP or RV-EGFP.

FIGS. 13A-B depict assays of locomotor activity and anxiety related to stimulation of LDT and LHb.

FIGS. 14A-D depict c-fos expression in VTA subpopulations induced by optical activation of LDT and LHb neurons.

FIGS. 17A-E depict retrograde labeling of various brain areas with two different fluorophores and related quantification.

FIGS. 18A-B depict injection of retrobeads and AAV-ChR2 for studies of synaptic connectivity.

FIGS. 19A-C depict fluorescent intensity of LDT and LHb terminals expressing ChR2-EYFP in VTA subregions.

FIGS. 20A-B depict behavioral assays of mice in which dopamine receptor antagonists were injected into the mPFC or NAc lateral shell and LHb or LDT neurons that project to VTA were optically stimulated.

FIGS. 21A-C depict expression of ChR2-EYFP in the midbrain, the LDT and the LHb following RV-ChR2 injections into the VTA.

DEFINITIONS

Figure 1:
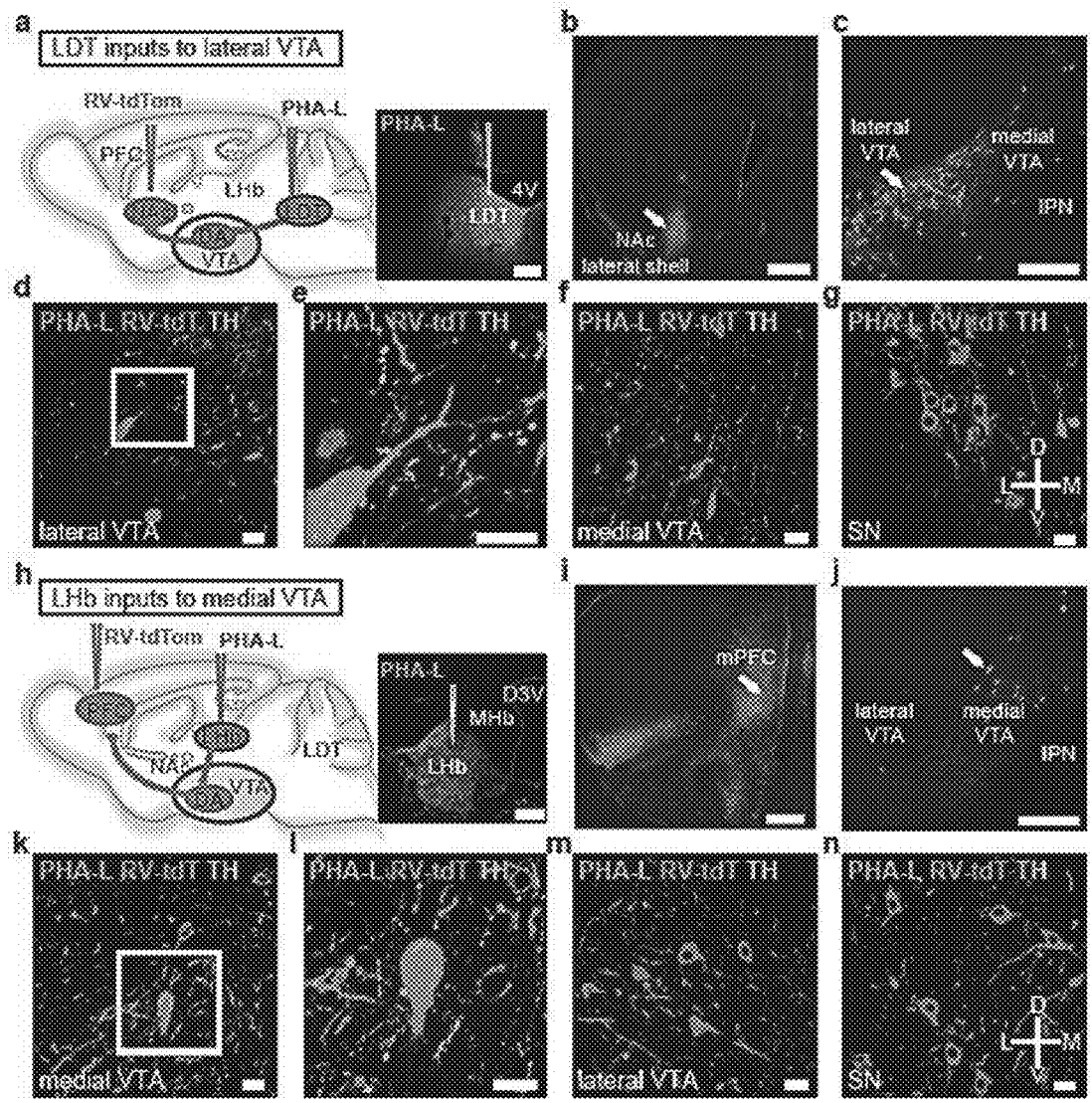
FIG. 1 depicts retrograde labeling of DA projection neurons and anterograde labeling of LDT or LHb fibers.

An "individual" can be a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a light-responsive protein" includes a plurality of such proteins and reference to "the reward- or aversive-related behavior" includes reference to one or more reward- or aversive-related behaviors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of inducing or modulating reward- or aversive-related behaviors in animals using light-responsive opsins. The present disclosure provides methods of identifying or screening compounds that may be used to treating mental disorders, or are relevant to disrupt or improve reward- or aversive related behaviors.

Modulating a Reward- or Aversive-Related Behavior

The present disclosure provides a method of inducing or modulating reward- or aversive-related behaviors in animals using light-responsive opsins. The method generally involves expressing a light-responsive opsin protein in one or both of two main inputs to the ventral tegmental area (VTA) from the laterodorsal tegmentum (LDT) and the lateral habenula (LHb); and exposing the inputs to light of a wavelength to which the light-responsive opsin protein responds.

In some cases, an excitatory light-activated opsin protein is expressed in an LHb neuron projecting to the VTA. In some cases, an inhibitory light-activated opsin protein is expressed in an LHb neuron projecting to the VTA. In some cases, an excitatory light-activated opsin protein is expressed in an LDT neuron projecting to the VTA. In some cases, an inhibitory light-activated opsin protein is expressed in an LDT neuron projecting to the VTA.

For example, an excitatory light-responsive polypeptide is expressed in an LHb neuron projecting to the VTA or in an LDT neuron projecting to the VTA, where the excitatory light-responsive polypeptide comprises an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11. In some cases, the excitatory light-responsive polypeptide comprises both ER export and membrane trafficking signals. For example, in some cases, the excitatory light-responsive polypeptide comprises, from the N-terminus to the C-terminus, the amino acid sequence at least 95% identical to the sequence shown in SEQ ID NO:5, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:5, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:17).

For example, an inhibitory light-responsive polypeptide is expressed in an LHb neuron projecting to the VTA or in an LDT neuron projecting to the VTA, where the inhibitory light-responsive polypeptide comprises an amino acid sequence having at least about 80%, at least about 85%, at least about 90%, at least about 95%, at least about 98%, or 100%, amino acid sequence identity to one of SEQ ID NOs:1, 2, 3, 4, 12, 13, 14, and 15. In some cases, the excitatory light-responsive polypeptide comprises both ER export and membrane trafficking signals. For example, in some cases, the excitatory light-responsive polypeptide comprises, from the N-terminus to the C-terminus, the amino acid sequence at least 95% identical to the sequence shown in SEQ ID NO:1, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:1, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:17).

Light-Responsive Opsin Proteins

Provided herein are optogenetic-based methods for selectively hyperpolarizing or depolarizing the neurons involved in reward- or aversive-related behaviors, using light-responsive opsin proteins to effectively modulate reward- or aversive-related behaviors, e.g., in individuals afflicted with disorders related to reward- or aversive-related behaviors. Optogenetics refers to the combination of genetic and optical methods used to control specific events in targeted cells of living tissue, even within freely moving mammals and other animals, with the temporal precision (millisecond-timescale) needed to keep pace with functioning intact biological systems. Optogenetics requires the introduction of fast light-responsive channel or pump proteins to the plasma membranes of target neuronal cells that allow temporally precise manipulation of neuronal membrane potential while maintaining cell-type resolution through the use of specific targeting mechanisms. Any microbial opsin that can be used to promote neural cell membrane hyperpolarization or depolarization in response to light may be used.

For example, the Halorhodopsin family of light-responsive chloride pumps (e.g., NpHR, NpHR2.0, NpHR3.0, NpHR3.1) and the GtR3 proton pump can be used to promote neural cell membrane hyperpolarization in response to light. As another example, eArch (a proton pump) can be used to promote neural cell membrane hyperpolarization in response to light. As another example, an ArchT opsin protein or a Mac opsin protein can be used to promote neural cell membrane hyperpolarization in response to light.

Additionally, members of the Channelrhodopsin family of light-responsive cation channel proteins (e.g., ChR2, SFOs, SSFOs, C1V1s) can be used to promote neural cell membrane depolarization or depolarization-induced synaptic depletion in response to a light stimulus.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive protein. Optionally, the light-responsive protein and the one or more amino acid sequence motifs may be separated by a linker. In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:16).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:16)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGAL-SAVGRELLFVTNPVVVNGS (SEQ ID NO:18))

2) the β2 subunit signal peptide of the neuronal nicotinic acetylcholine receptor (e.g., MAGHSNSMALFSFSLL-WLCSGVLGTEF (SEQ ID NO:19));

3) a nicotinic acetylcholine receptor signal sequence (e.g., MGLRALMLWLLAAAGLVRESLQG (SEQ ID NO:20)); and 4) a nicotinic acetylcholine receptor signal sequence (e.g., MRGTPLLLVVSLFSLLQD (SEQ ID NO:21)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use in a modified opsin of the present disclosure include, e.g., VXXSL (SEQ ID NO:22) (where X is any amino acid) (e.g., VKESL (SEQ ID NO:23); VLGSL (SEQ ID NO:24); etc.); NANSFCYENEVALTSK (SEQ ID NO:25); FXYENE (SEQ ID NO:26) (where X is any amino acid), e.g., FCYENEV (SEQ ID NO:17); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some embodiments, the signal peptide sequence in the protein can be deleted or substituted with a signal peptide sequence from a different protein.

Inhibitory Light-Responsive Opsin Proteins

In some embodiments, a subject method for modulating a behavioral feature involves use of an inhibitory light-responsive opsin protein. Inhibitory light-responsive opsin proteins include polypeptides having sequence similarity (e.g., at least about 85%, 90%, 91%, 92%, 93%, 94%, 95%, 96%, 97%, 98%, 99%, or 100% amino acid sequence identity) to one of SEQ ID NOs:1, 2, 3, 4, 12, 13, 14, and 15 (FIGS. 6A-H).

Light-Responsive Chloride Pumps

In some aspects of the methods provided herein, one or more members of the Halorhodopsin family of light-responsive chloride pumps are expressed on the plasma membranes of one or both of two main inputs to the VTA from LDT and the lateral LHb.

In some aspects, said one or more light-responsive chloride pump proteins expressed on the plasma membranes of the neurons described above can be derived from *Natronomonas pharaonis*. In some embodiments, the light-responsive chloride pump proteins can be responsive to amber light as well as red light and can mediate a hyperpolarizing current in the neuron when the light-responsive chloride pump proteins are illuminated with amber or red light. The wavelength of light which can activate the light-responsive chloride pumps can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 85%, 90%, 91%, 92%, 93%, 94%, 95%, 96%, 97%, 98%, 99%, or 100% identical to the sequence shown in SEQ ID NO: 1. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 85%, 90%, 91%, 92%, 93%, 94%, 95%, 96%, 97%, 98%, 99%, or 100% identical to the sequence shown in SEQ ID NO: 1 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:26), where X can be any amino acid. In another embodiment, the ER export signal can comprise the amino acid sequence VXXSL (SEQ ID NO:22), where X can be any amino acid. In some embodiments, the ER export signal can comprise the amino acid sequence FCYENEV (SEQ ID NO:17).

Endoplasmic reticulum (ER) export sequences that are suitable for use in a modified opsin of the present disclosure include, e.g., VXXSL (SEQ ID NO:22) (where X is any amino acid) (e.g., VKESL (SEQ ID NO:23); VLGSL (SEQ ID NO:24); etc.); NANSFCYENEVALTSK (SEQ ID NO:25); FXYENE (SEQ ID NO:26) (where X is any amino acid), e.g., FCYENEV (SEQ ID NO:17); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, the light-responsive chloride pump proteins described herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO: 1 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:16).

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:27). In another embodiment, the light-responsive chloride pump protein comprises an amino acid sequence at least 95% identical to SEQ ID NO:2.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO: 1, wherein the N-terminal signal peptide of SEQ ID NO:1 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:3.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:1. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:1 and an endoplasmic reticulum (ER) export signal. In some embodiments, the amino acid sequence at least 95% identical to the sequence shown in SEQ ID NO:1 is linked to the ER export signal through a linker. In some embodiments, the ER export signal comprises the amino acid sequence FXYENE (SEQ ID NO:26), where X can be any amino acid. In another embodiment, the ER export signal comprises the amino acid sequence VXXSL (SEQ ID NO:22), where X can be any amino acid. In some embodiments, the ER export signal comprises the amino acid sequence FCYENEV (SEQ ID NO:17). In some embodiments, the NpHR opsin protein comprises an amino acid sequence at least 95% identical to the sequence shown in SEQ ID NO:1, an ER export signal, and a membrane trafficking signal. In other embodiments, the NpHR opsin protein comprises, from the N-terminus to the C-terminus, the amino acid sequence at least 95% identical to the sequence shown in SEQ ID NO:1, the ER export signal, and the membrane trafficking signal. In other embodiments, the NpHR opsin protein comprises, from the N-terminus to the C-terminus, the amino acid sequence at least 95% identical to the sequence shown in SEQ ID NO:1, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence K S R I T S E G E Y I P L D Q I D I N V (SEQ ID NO:16). In some embodiments, the membrane trafficking signal is linked to the amino acid sequence at least 95% identical to the sequence shown in SEQ ID NO:1 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein (GFP), or a cyan fluorescent protein. In some embodiments, the light-responsive opsin protein further comprises an N-terminal signal peptide. In some embodiments, the light-responsive opsin protein comprises the amino acid sequence of SEQ ID NO:2. In some embodiments, the light-responsive opsin protein comprises the amino acid sequence of SEQ ID NO:3.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:1, an ER export signal, and a membrane trafficking signal. In another embodiment, the polynucleotides comprise a sequence which encodes an amino acid at least 95% identical to SEQ ID NO:2 and SEQ ID NO:3. The polynucleotides may be in an expression vector (such as, but not limited to, a viral vector described herein). The polynucleotides may be used for expression of the light-responsive chloride ion pump proteins.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Light-Responsive Proton Pumps

In some aspects of the methods provided herein, one or more light-responsive proton pumps are expressed on the plasma membranes of one or both of two main inputs to the VTA from LDT and the lateral LHb. In some embodiments, the light-responsive proton pump protein can be responsive to blue light and can be derived from *Guillardia theta*, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:4. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. The polynucleotides may be used for expression of the light-responsive protein in one or both of two main inputs to the VTA from LDT and the lateral LHb.

Further disclosure related to light-responsive proton pump proteins can be found in International Patent Application No. PCT/US2011/028893, the disclosure of which is hereby incorporated by reference in its entirety.

In some embodiments, the light-responsive proton pump protein can be responsive to green or yellow light and can be derived from *Halorubrum sodomense*, wherein the proton pump protein can be capable of mediating a hyperpolarizing current in the cell when the cell is illuminated with green or yellow light. The light can have a wavelength between about 560 and about 570 nm or can have a wavelength of about 566 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:12. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:12 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:12. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:12. The polynucleotides may be used for expression of the light-responsive protein in neural cells (e.g. one or both of two main inputs to the VTA from LDT and the lateral LHb).

Excitatory Light-Responsive Opsin Proteins

In some embodiments, a subject method for modulating a behavioral feature involves use of an excitatory light-responsive opsin protein. Excitatory light-responsive opsin proteins include polypeptides having sequence similarity (e.g., at least about 85%, 90%, 91%, 92%, 93%, 94%, 95%, 96%, 97%, 98%, 99%, or 100% amino acid sequence identity) to one of SEQ ID NOs:5, 6, 7, 8, 9, 10, and 11 (FIGS. 6A-H).

Light-Responsive Cation Channel Proteins

In some aspects of the methods provided herein, one or more light-responsive cation channels can be expressed on the plasma membranes of one or both of two main inputs to the VTA from LDT and the lateral LHb.

In some aspects, the light-responsive cation channel protein can be derived from *Chlamydomonas reinhardtii*, wherein the cation channel protein can be capable of mediating a depolarizing current in the cell when the cell is illuminated with light. In another embodiment, the light-responsive cation channel protein can comprise an amino acid sequence at least about 90%, 91%, 92%, 93%, 94%, 95%, 96%, 97%, 98%, 99%, or 100% identical to the sequence shown in SEQ ID NO:5. The light used to activate the light-responsive cation channel protein derived from *Chlamydomonas reinhardtii* can have a wavelength between about 460 and about 495 nm or can have a wavelength of about 480 nm. Additionally, the light can have an intensity of at least about 100 Hz. In some embodiments, activation of the light-responsive cation channel derived from *Chlamydomonas reinhardtii* with light having an intensity of 100 Hz can cause depolarization-induced synaptic depletion of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to depolarize the plasma membrane of one or both of two main inputs to the VTA from LDT and the lateral LHb in response to light.

In some embodiments, the light-responsive cation channel comprises a T159C substitution of the amino acid sequence set forth in SEQ ID NO:5. In some embodiments, the light-responsive cation channel comprises a L132C substitution of the amino acid sequence set forth in SEQ ID NO:5. In some embodiments, the light-responsive cation channel comprises an E123T substitution of the amino acid sequence set forth in SEQ ID NO:5. In some embodiments, the light-responsive cation channel comprises an E123A substitution of the amino acid sequence set forth in SEQ ID NO:5. In some embodiments, the light-responsive cation channel comprises a T159C substitution and an E123T substitution of the amino acid sequence set forth in SEQ ID NO:5. In some embodiments, the light-responsive cation channel comprises a T159C substitution and an E123A substitution of the amino acid sequence set forth in SEQ ID NO:5. In some embodiments, the light-responsive cation channel comprises a T159C substitution, an L132C substitution, and an E123T substitution of the amino acid sequence set forth in SEQ ID NO:5. In some embodiments, the light-responsive cation channel comprises a T159C substitution, an L132C substitution, and an E123A substitution of the amino acid sequence set forth in SEQ ID NO:5. In some embodiments, the light-responsive cation channel comprises an L132C substitution and an E123T substitution of the amino acid sequence set forth in SEQ ID NO:5. In some embodiments, the light-responsive cation channel comprises an L132C substitution and an E123A substitution of the amino acid sequence set forth in SEQ ID NO:5.

Further disclosure related to light-responsive cation channel proteins can be found in U.S. Patent Application Publication No. 2007/0054319 and International Patent Application Publication Nos. WO 2009/131837 and WO 2007/024391, the disclosures of each of which are hereby incorporated by reference in their entireties.

Step Function Opsins and Stabilized Step Function Opsins

In other embodiments, the light-responsive cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:5. In other embodiments, the SFO protein has a C128A mutation in SEQ ID NO:5. In other embodiments, the SFO protein has a C128S mutation in SEQ ID NO:5. In another embodiment, the SFO protein has a C128T mutation in SEQ ID NO:5. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:6.

In some embodiments, the SSFO protein can have a mutation at amino acid residue D156 of SEQ ID NO:5. In other embodiments, the SSFO protein can have a mutation at both amino acid residues C128 and D156 of SEQ ID NO:5. In one embodiment, the SSFO protein has an C128S and a D156A mutation in SEQ ID NO:5. In another embodiment, the SSFO protein can comprise an amino acid sequence at least about 90%, 91%, 92%, 93%, 94%, 95%, 96%, 97%, 98%, 99%, or 100% identical to the sequence shown in SEQ ID NO:7. In another embodiment, the SSFO protein can comprise a C128T mutation in SEQ ID NO:5. In some embodiments, the SSFO protein comprises C128T and D156A mutations in SEQ ID NO:5.

In some embodiments the SFO or SSFO proteins provided herein can be capable of mediating a depolarizing current in the cell when the cell is illuminated with blue light. In other embodiments, the light can have a wavelength of about 445 nm. Additionally, the light can have an intensity of about 100 Hz. In some embodiments, activation of the SFO or SSFO protein with light having an intensity of 100 Hz can cause depolarization-induced synaptic depletion of the neurons expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970 and U.S. Provisional Patent Application Nos. 61/410,704 and 61/511,905, the disclosures of each of which are hereby incorporated by reference in their entireties.

C1V1 Chimeric Cation Channels

In other embodiments, the light-responsive cation channel protein can be a C1V1 chimeric protein derived from the VChR1 protein of *Volvox carteri* and the ChR1 protein from *Chlamydomonas reinhardtii*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least about 90%, 91%, 92%, 93%, 94%, 95%, 96%, 97%, 98%, 99%, or 100% identical to the sequence shown in SEQ ID NO:8.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, the light can have an intensity of about 100 Hz. In some embodiments, activation of the C1V1 chimeric protein with light having an intensity of 100 Hz can cause depolarization-induced synaptic depletion of the neurons expressing the C1V1 chimeric protein. In some embodiments, the disclosed C1V1 chimeric protein can have specific properties and characteristics for use in depolarizing the membrane of one or both of two main inputs to the VTA from LDT and the lateral LHb in response to light.

C1V1 Chimeric Mutant Variants

In some aspects, the present disclosure provides polypeptides comprising substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, provided herein are C1V1 chimeric light-responsive opsin proteins that can have specific amino acid substitutions at key positions throughout the retinal binding pocket of the VChR1 portion of the chimeric polypeptide. In some embodiments, the C1V1 protein can have a mutation at amino acid residue E122 of SEQ ID NO:7. In some embodiments, the C1V1 protein can have a mutation at amino acid residue E162 of SEQ ID NO:7. In other embodiments, the C1V1 protein can have a mutation at both amino acid residues E162 and E122 of SEQ ID NO:7. In other embodiments, the C1V1 protein can comprise an amino acid sequence at least about 90%, 91%, 92%, 93%, 94%, 95%, 96%, 97%, 98%, 99%, or 100% identical to the sequence shown in SEQ ID NO:9, SEQ ID NO:10, or SEQ ID NO:11. In some embodiments, each of the disclosed mutant C1V1 chimeric proteins can have specific properties and characteristics for use in depolarizing the membrane of one or both of two main inputs to the VTA from LDT and the lateral LHb in response to light.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E122 mutant chimeric protein with light having an intensity of 100 Hz can cause depolarization-induced synaptic depletion of the neurons expressing the C1V1-E122 mutant chimeric protein. In some embodiments, the disclosed C1V1-E122 mutant chimeric protein can have specific properties and characteristics for use in depolarizing the membrane of one or both of two main inputs to the VTA from LDT and the lateral LHb in response to light.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E162 mutant chimeric protein with light having an intensity of 100 Hz can cause depolarization-induced synaptic depletion of the neurons expressing the C1V1-E162 mutant chimeric protein. In some embodiments, the disclosed C1V1-E162 mutant chimeric protein can have specific properties and characteristics for use in depolarizing the membrane of one or both of two main inputs to the VTA from LDT and the lateral LHb in response to light.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, the light can have an intensity of about 100 Hz. In some embodiments, activation of the C1V1-E122/E162 mutant chimeric protein with light having an intensity of 100 Hz can cause depolarization-induced synaptic depletion of the neurons expressing the C1V1-E122/E162 mutant chimeric protein. In some embodiments, the disclosed C1V1-E122/E162 mutant chimeric protein can have specific properties and characteristics for use in depolarizing the membrane of one or both of two main inputs to the VTA from LDT and the lateral LHb in response to light.

Further disclosure related to C1V1 chimeric cation channels as well as mutant variants of the same can be found in U.S. Provisional Patent Application Nos. 61/410,736, 61/410,744, and 61/511,912, the disclosures of each of which are hereby incorporated by reference in their entireties.

Polynucleotides

The disclosure also provides polynucleotides comprising a nucleotide sequence encoding a light-responsive protein described herein. In some embodiments, the polynucleotide comprises an expression cassette. In some embodiments, the polynucleotide is a vector comprising the above-described nucleic acid. In some embodiments, the nucleic acid encoding a light-responsive protein of the disclosure is operably linked to a promoter. Promoters are well known in the art. Any promoter that functions in the host cell can be used for expression of the light-responsive opsin proteins and/or any variant thereof of the present disclosure. In one embodiment, the promoter used to drive expression of the light-responsive opsin proteins can be a promoter that is specific to a particular neuron. Initiation control regions or promoters, which are useful to drive expression of the light-responsive opsin proteins or variant thereof in a specific animal cell are numerous and familiar to those skilled in the art. Virtually any promoter capable of driving these nucleic acids can be used. In some embodiments, the promoter used to drive expression of the light-responsive protein can be a Thy1 promoter (See, e.g., Llewellyn, et al., 2010, *Nat. Med.*, 16(10):1161-1166). In other embodiments, the promoter used to drive expression of the light-responsive protein can be the EF1α promoter, a cytomegalovirus (CMV) promoter, the CAG promoter, a synapsin-I promoter (e.g., a human synapsin-I promoter), a human synuclein 1 promoter, a calcium/calmodulin-dependent kinase II alpha (CAMKIIα) promoter, or any other promoter capable of driving expression of the light-responsive opsin proteins in a neuron of mammals.

Also provided herein are vectors comprising a nucleotide sequence encoding a light-responsive protein or any variant thereof described herein. The vectors that can be administered according to the present disclosure also include vectors comprising a nucleotide sequence which encodes an RNA (e.g., an mRNA) that when transcribed from the polynucleotides of the vector will result in the accumulation of light-responsive opsin proteins on the plasma membranes of target animal cells. Vectors which may be used include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" In *Parvoviruses* (J R Kerr, S F Cotmore. M E Bloom, R M Linden, C R Parrish, Eds.) p 5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos.

6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

Delivery of Light-Responsive Opsin Proteins

In some aspects, polynucleotides encoding the light-responsive opsin proteins disclosed herein (for example, an AAV vector) can be delivered directly to one or both of two main inputs to the VTA from LDT and the lateral LHb with a needle, catheter, or related device, using neurosurgical techniques known in the art, such as by stereotactic injection (See, e.g., Stein et al., *J. Virol*, 73:34243429, 1999; Davidson et al., *PNAS*, 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties) or fluoroscopy.

Other methods to deliver the light-responsive opsin proteins to the neurons of interest can also be used, such as, but not limited to, transfection with ionic lipids or polymers, electroporation, optical transfection, impalefection, or via gene gun.

Light and Electrical Sources

In some aspects of the present disclosure, the light-responsive opsin proteins disclosed herein can be activated by an implantable light source (such as a light cuff) or an implantable electrode placed around or near neurons expressing the light-responsive opsin proteins. Electrode cuffs and electrodes surgically placed around or near neurons for use in electrical stimulation of those neurons are well known in the art (See, for example, U.S. Pat. Nos. 4,602,624, 7,142,925 and 6,600,956 as well as U.S. Patent Publication Nos. 2008/0172116 and 2010/0094372, the disclosures of each of which are hereby incorporated by reference in their entireties). The light sources (such as a light cuff) or electrodes of the present invention can be comprised of any useful composition or mixture of compositions, such as platinum or stainless steel, as are known in the art, and may be of any useful configuration for stimulating the light-responsive opsin proteins disclosed herein.

The electrodes or implantable light source (such as a light cuff) may be placed around or near a neuron expressing a light-responsive protein.

In some embodiments, the implantable light source (such as a light cuff) does not completely surround the a region containing a neuron expressing a light-responsive protein, but, rather, can have a U-shape. In another embodiment, the implantable light source can have an attachment arm that can be used to guide the implantable light source (such as a light cuff) to the neuronal region to be exposed to light. The attachment arm can be removed following implantation of the light source or can be left in place to fix the position of the light source in proximity to the neurons of interest.

The implantable light source (such as a light cuff) can comprise an inner body, the inner body having at least one means for generating light which is configured to a power source. In some embodiments, the power source can be an internal battery for powering the light-generating means. In another embodiment, the implantable light source can comprise an external antenna for receiving wirelessly transmitted electromagnetic energy from an external source for powering the light-generating means. The wirelessly transmitted electromagnetic energy can be a radio wave, a microwave, or any other electromagnetic energy source that can be transmitted from an external source to power the light-generating means of the implantable light source (such as a light cuff). In one embodiment, the light-generating means is controlled by an integrated circuit produced using semiconductor or other processes known in the art.

In some aspects, the light means can be a light emitting diode (LED). In some embodiments, the LED can generate blue and/or green light. In other embodiments, the LED can generate amber and/or yellow light. In some embodiments, several micro LEDs are embedded into the inner body of the implantable light source (such as a light cuff). In other embodiments, the light-generating means is a solid state laser diode or any other means capable of generating light. The light generating means can generate light having an intensity sufficient to activate the light-responsive opsin proteins expressed on the plasma membrane of the nerves in proximity to the light source (such as a light cuff). In some embodiments, the light-generating means produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In other embodiments, the light-generating means produces light having an intensity of at least about 100 Hz.

In some aspects, the light-generating means can be externally activated by an external controller. The external controller can comprise a power generator which can be mounted to a transmitting coil. In some embodiments of the external controller, a battery can be connected to the power generator, for providing power thereto. A switch can be connected to the power generator, allowing an individual to manually activate or deactivate the power generator. In some embodiments, upon activation of the switch, the power generator can provide power to the light-generating means on the light source through electromagnetic coupling between the transmitting coil on the external controller and the external antenna of the implantable light source (such as a light cuff). The transmitting coil can establish an electromagnetic coupling with the external antenna of the implantable light source when in proximity thereof, for supplying power to the light-generating means and for transmitting one or more control signals to the implantable light source. In some embodiments, the electromagnetic coupling between the transmitting coil of the external controller and the external antenna of the implantable light source (such as a light cuff) can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, *Opticon* 1826, (8): Spring, 2010).

Non-Human Animal Model of Reward- or Aversive-Related Behavior

The present disclosure provides a non-human animal model of reward- or aversive-related behavior disorder, which non-human animal model expresses a light-activated opsin protein in one or both of two main inputs to the VTA from the LDT and the LHb. Exposure of the light-activated opsin protein to light of a wavelength to which the light-activated opsin protein responds results in an adverse reward- or aversive-related behavior. A subject non-human animal model is in some embodiments a mouse. A subject non-human animal model is in some embodiments a rat. A subject non-human animal model is in some embodiments a non-human primate. A subject non-human animal model is useful in screening methods to identify agents that modulate pathological reward- or aversive related behaviors, where such behaviors include addiction, eating disorders, anxiety disorders, and the like.

In some cases, a subject non-human animal model expresses an excitatory light-activated opsin protein in an LHb neuron projecting to the VTA. In some cases, a subject non-human animal model expresses an inhibitory light-activated opsin protein in an LHb neuron projecting to the VTA. In some cases, a subject non-human animal model expresses an excitatory light-activated opsin protein in an LDT neuron projecting to the VTA. In some cases, a subject non-human animal model expresses an inhibitory light-activated opsin protein in an LDT neuron projecting to the VTA.

For example, in some cases, a subject non-human animal model expresses an excitatory light-activated opsin protein in an LDT neuron projecting to the VTA, such that, when the LDT neuron is exposed to light of a wavelength to which the excitatory light-activated opsin protein responds, the non-human animal model exhibits strong conditioned place preference (CPP).

In other cases, a subject non-human animal model expresses an excitatory light-activated opsin protein in an LHb neuron projecting to the VTA, such that, when the LHb neuron is exposed to light of a wavelength to which the excitatory light-activated opsin protein responds, the non-human animal model exhibits strong conditioned place aversion.

For example, in some embodiments, a subject non-human animal model comprises an excitatory light-responsive polypeptide comprising an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11, where the polypeptide is expressed in an LDT neuron projecting to the VTA, and wherein, exposure of the LDT neuron projecting to the VTA to light of a wavelength to which the light-responsive protein responds results in strong CPP. In some cases, the excitatory light-responsive polypeptide comprises both ER export and membrane trafficking signals. For example, in some cases, the excitatory light-responsive polypeptide comprises, from the N-terminus to the C-terminus, the amino acid sequence at least 95% identical to the sequence shown in SEQ ID NO:5, an ER export signal, and a membrane trafficking signal. In other cases, the excitatory light-responsive polypeptide comprises, from the N-terminus to the C-terminus, the amino acid sequence at least 95% identical to the sequence shown in SEQ ID NO:5, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:17).

As another example, in some embodiments, a subject non-human animal model comprises an excitatory light-responsive polypeptide comprising an amino acid sequence having at least about 80%, at least about 85%, at least about 90%, at least about 95%, at least about 98%, or 100%, amino acid sequence identity to one of SEQ ID NOs:5, 6, 7, 8, 9, 10, and 11, where the polypeptide is expressed in an LHb neuron projecting to the VTA, and wherein, exposure of the LHb neuron projecting to the VTA to light of a wavelength to which the light-responsive protein responds results in strong CPA.

As another example, in some embodiments, a subject non-human animal model comprises an inhibitory light-responsive polypeptide comprising an amino acid sequence having at least about 80%, at least about 85%, at least about 90%, at least about 95%, at least about 98%, or 100%, amino acid sequence identity to one of SEQ ID NOs:1, 2, 3, 4, 12, 13, 14, and 15, where the polypeptide is expressed in an LDT neuron projecting to the VTA. For example, in some cases, the inhibitory light-responsive polypeptide comprises, from the N-terminus to the C-terminus, the amino acid sequence at least 95% identical to the sequence shown in SEQ ID NO:1, an ER export signal, and a membrane trafficking signal. In other cases, the inhibitory light-responsive polypeptide comprises, from the N-terminus to the C-terminus, the amino acid sequence at least 95% identical to the sequence shown in SEQ ID NO:1, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQ-IDINV (SEQ ID NO:16). In some cases, the ER export signal comprises the sequence FCYENEV (SEQ ID NO:17).

As another example, in some embodiments, a subject non-human animal model comprises an inhibitory light-responsive polypeptide comprising an amino acid sequence having at least about 80%, at least about 85%, at least about 90%, at least about 95%, at least about 98%, or 100%, amino acid sequence identity to one of SEQ ID NOs:1, 2, 3, 4, 12, 13, 14, and 15, where the polypeptide is expressed in an LHb neuron projecting to the VTA. For example, in some cases, the inhibitory light-responsive polypeptide comprises, from the N-terminus to the C-terminus, the amino acid sequence at least 95% identical to the sequence shown in SEQ ID NO:1, an ER export signal, and a membrane trafficking signal. In other cases, the inhibitory light-responsive polypeptide comprises, from the N-terminus to the C-terminus, the amino acid sequence at least 95% identical to the sequence shown in SEQ ID NO:1, a membrane trafficking signal, and a ER export signal. In some cases, the membrane trafficking signal is derived from the amino acid sequence of the human inward rectifier potassium channel Kir2.1. In some cases, the membrane trafficking signal comprises the amino acid sequence KSRITSEGEYIPLDQIDINV (SEQ ID NO:16). In some cases, the ER export signal comprises the sequence FCYENEV (SEQ ID NO:17).

A nucleic acid (e.g., an expression vector) comprising a nucleotide sequence encoding a light-responsive protein can be introduced into a non-human animal (e.g., a rodent such as a rat or a mouse) by any convenient means. For example, a nucleic acid (e.g., an expression vector) comprising a nucleotide sequence encoding a light-responsive protein can be injected stereotactically into the VTA, into an LDT neuron projecting into the VTA, or into an LHb neuron projecting into the VTA.

Suitable expression vectors include, but are not limited to, lentiviral, HSV, adenoviral, rabies virus vectors, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art. Suitable expression vectors are described above, and in the Examples.

Screening Methods

Provided herein are two different methods to induce reward- or aversive related behaviors. First, by injection of a vector, e.g., an adeno-associated virus vector, that expresses a light sensitive opsin into a defined target region and optical stimulation of terminals that express this opsin in another brain region. Second, by injection of a viral vector, e.g., a retrogradely transported virus (e.g. rabies virus) vector, which expresses a light-sensitive (light-responsive) opsin into a defined brain area and optical stimulation of cell bodies that project to this brain area and express the opsin.

A subject screening method generally involves contacting a non-human animal model of a reward- or aversive-related behavior disorder with a test agent; and determining the effect of the test agent on a reward- or aversive-related behavior, e.g., when a neuron expressing a light-activated opsin is exposed to light of a wavelength that activates the opsin. A test agent that reduces an adverse reward- or aversive-related behavior is considered a candidate agent for treating a reward- or aversive-related behavior disorder.

For example, a test agent that reduces a reward- or aversive-related behavior, exhibited by a subject non-human animal model, by at least about 5%, at least about 10%, at least about 15%, at least about 20%, at least about 25%, or more than 25% (e.g., 25% to 50%; 50% to 75%; etc.) can be considered a candidate agent for ameliorating (treating) a pathological reward- or aversive-related behavior. Test agents identified using a subject method can be considered candidate agents for treating any of a variety of pathological reward- or aversive-related behaviors, e.g., addiction, anxiety disorders, and the like.

As described above, a non-human animal model of reward- or aversive-related behavior disorder expresses a light-activated opsin protein in one or both of two main inputs to the VTA from the LDT and the LHb. Exposure of the light-activated opsin protein to light of a wavelength to which the light-activated opsin protein responds results in an adverse reward- or aversive-related behavior. A test agent that reduces the adverse reward- or aversive-related behavior is considered a candidate agent for treating a reward- or aversive-related behavior disorder.

A light-responsive protein expressed in a subject non-human animal model can be activated by an implantable light source, where suitable light sources are described above and in the Examples. Suitable wavelengths for activating an inhibitory or an excitatory opsin protein are described above.

Various symptoms can be analyzed in a subject non-human animal model. Suitable tests include the conditioned place preference (CPP) test; and the conditioned place aversion (CPA) test. Other tests that may be used include, e.g., the forced swim test (FST) (see, e.g., Porsolt et al. (1977) *Nature* 266:730; and Petit-Demouliere, et al. (2005) *Psychopharmacology* 177: 245); the tail suspension test (see, e.g., Cryan et al. (2005) *Neurosci. Behav. Rev.* 29:571; and Li et al. (2001) *Neuropharmacol.* 40:1028); conditioned place aversion (see, e.g., Bechtholt-Gompf et al. (2010) *Neuropsychopharmacol.* 35:2049); the novelty hypophagia test (Dulawa, et al. (2005) *Neurosci. Biobehav. Rev.* 29:771); the social defeat stress test (see, e.g., Blanchard et al. (2001) *Physiol Behav.* 73:261-271; and Kudryavtseva et al. (1991) *Pharmacol. Biochem. Behav.* 38: 315); the sucrose preference test (see, e.g., Kurre Nielsen, et al. (2000) *Behavioural Brain Research* 107:21-33); the open field test (see, e.g., Holmes (2001) *Neurosci. Biobehav. Rev.* 25:261-273); the elevated plus maze test (see, e.g., Holmes (2001) supra); and the like. Any such test can be used in a subject screening method.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents can be small organic or inorganic compounds having a molecular weight of more than 50 daltons and less than about 2,500 daltons. Candidate agents can comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, and derivatives, structural analogs or combinations thereof.

Assays of the present disclosure include controls, where suitable controls include a subject non-human animal model that has been exposed to activating light, but has not been administered the test agent.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Input-Specific Control of Reward and Aversion in the VTA

Materials and Methods

Animals.

Male adult (10-12 weeks of age) C57Bl6 (Charles River) or TH-Cre [B6.Cg-Tg(Th-cre)1Tmd/J; Jackson Laboratory] mice were used for all experiments. All procedures complied with the animal care standards set forth by the National Institutes of Health and were approved by Stanford University's Administrative Panel on Laboratory Animal Care.

Virus Generation.

The adeno-associated viruses (AAVs) used in this study were generated as previously described[38] either by the Deisseroth lab (AAV-ChR2) or the Stanford Neuroscience Gene Vector and Virus Core (AAV-DIO-RVG). Rabies virus (RV) was generated from a full length cDNA plasmid containing all components of RV (SAD L16)[39]. We replaced the rabies virus glycoprotein with enhanced green fluorescent protein (EGFP), tdTomato or ChR2-H134R fused to enhanced yellow fluorescent protein (EYFP) to generate RV expressing EGFP (RV-EGFP), tdTomato (RV-tdTomato), or ChR2-H134R (RV-ChR2). To harvest RV from this cDNA we used a modified version of published protocols[39,40]. Briefly, HEK293T cells were transfected with a total of 6 plasmids; 4 plasmids expressing the RV components pTIT-N, pTIT-P, pTIT-G, and pTIT-L; one plasmid expressing T7 RNA polymerase (pCAGGS-T7), and the aforementioned glycoprotein-deleted RV cDNA plasmid expressing EGFP, tdTomato, or ChR2. For the amplification of RV, the media bathing these HEK293T cells was collected 3-4 days post-transfection and moved to baby hamster kidney (BHK) cells stably expressing RV glycoprotein (BHK-B19G)[40]. After three days, the media from BHK-B19G cells was collected, centrifuged for 5 min at 3,000×g to remove cell debris, and concentrated by ultracentrifugation (55,000×g for 2 hr). Pellets were suspended in DPBS, aliquoted and stored at −80° C. The titer of concentrated RV was measured by infecting HEK293 cells and monitoring fluorescence.

Stereotaxic Injections and Optic Fiber/Cannula Implantations.

As previously described[4,5], all stereotaxic injections were performed under general ketamine-medetomidine anesthesia and using a stereotaxic instrument (Kopf Instruments). Adult (10-12 weeks; 25-30 g) male C57BL/6 and TH-Cre mice were group-housed until surgery. Mice were maintained on a 12:12 light cycle (lights on at 07:00). For retrobead labeling (100 nl; LumaFluor Inc., Naples, Fla.) mice were injected unilaterally with fluorescent retrobeads in the nucleus accumbens (NAc) lateral shell (bregma 1.45 mm; lateral 1.75 mm; ventral 4.0 mm), NAc medial shell (bregma 1.78 mm; lateral 0.5 mm; ventral 4.1 mm), or medial prefrontal cortex (mPFC) (two injections at four different sites: bregma 1.95 mm, 2.05 mm, 2.15 mm, and 2.25 mm; lateral 0.27 mm; ventral 2.1 mm and 1.6 mm; injected total volume in mPFC: 400 nl; the target area was the prelimbic and infralimbic cortex) using a 1 µl Hamilton syringe (Hamilton, Reno, Nev.). Note that these empirically derived stereotaxic coordinates do not precisely match those given in the mouse brain atlas (Franklin and Paxinos, 2001), which we used as references for the injection-site images. On average, the caudo-rostral axis appeared to be approximately shifted caudally by 400 µm. Little labeling was observed in the pipette tract (i.e. cingulate and motor cortices for mPFC injections or in the dorsal striatum for NAc lateral shell injections). To allow adequate time for retrograde transport of the Retrobeads into the somas of midbrain DA neurons, minimal survival periods prior to sacrifice depended on the respective injection areas: NAc lateral shell, 3 days; NAc medial shell, 14 days; and mPFC, 21 days. For viral infections a small amount of concentrated rabies virus (RV) solution (0.5-1 µl of RV-EGFP, RV-tdTomato or RV-ChR2) or AAV-DIO-RVG or AAV-ChR2-EYFP was injected unilaterally in the LDT (bregma −5.0 mm; lateral 0.5 mm; ventral 3.0 mm) or LHb (bregma −1.58 mm; lateral 0.4 mm; ventral 2.65 mm) or into the VTA (bregma −3.4 mm; lateral 0.35 mm; ventral 4.0 mm) or mPFC or NAc lateral shell (same coordinates as for retrobead injections) using a syringe pump (Harvard Apparatus, MA) at a slow rate (100-150 nl/min). The injection needle was withdrawn 5 min after the end of the infusion.

For the dual RV injections (FIG. 17), one virus (RV-EGFP or RV-tdTomato) was injected into the VTA and the other was injected into either the ventral pallidum (bregma 0.62 mm; lateral 1.10 mm; ventral 4.75 mm), lateral septum (bregma 0.62 mm; lateral 0.35 mm; ventral 3.0 mm), lateral hypothalamus (bregma −0.94 mm; lateral 1.00 mm; ventral 4.75 mm), mPFC (two injections at four different sites: bregma 1.95 mm, 2.05 mm, 2.15 mm, and 2.25 mm; lateral 0.27 mm; ventral 2.1 mm and 1.6 mm), mediodorsal thalamic nucleus (bregma −1.22 mm; lateral 0.25 mm; ventral 3.25 mm) or supraoculomotor central grey (bregma −4.04 mm; lateral 0.3 mm; ventral 2.7 mm). For anterograde labeling of LDT and LHb terminals in the VTA the anterograde tracer *Phaseolus vulgaris leucoagglutinin* (PHA-L; 50 nl; 2.5% in 0.01 M phosphate buffer; Vector, Burlingame, Calif.) was injected into the LDT or LHb (same coordinates as for virus injections). The survival period for the PHA-L injected animals was 3 weeks and for the AAV-ChR2 injected animals 8-12 weeks.

For behavioral experiments mice that were injected with RV-EGFP or RV-ChR2 in the VTA received unilateral implantation of a doric patch-cord chronically implantable fiber (NA=0.22; Doric lenses, Quebec, Canada) over the LDT (bregma −5.0 mm, lateral 0.5 mm, ventral 2.0 mm) or LHb (bregma −1.58 mm, lateral 0.4 mm, ventral 2.0 mm). One layer of adhesive cement (C&B metabond; Parkell, Edgewood, N.Y.) followed by cranioplastic cement (Dental cement; Stoelting, Wood Dale, Ill.) was used to secure the fiber guide system to the skull. After 20 min, the incision was closed with a suture and tissue adhesive (Vetbond; Fisher, Pittsburgh, Pa.). The animal was kept on a heating pad until it recovered from anesthesia. For intra-VTA stimulation of LHb or LDT axon terminals, AAV-ChR2 was injected into LHb or LDT, respectively. 10 weeks following the virus injection a doric optic fiber was implanted unilaterally over the caudal medial VTA for stimulation of LHb axon terminals (bregma −3.4 mm; lateral 0.35 mm; ventral 3.6 mm) and over the lateral VTA for stimulation of LDT axon terminals (bregma −3.4 mm; lateral 0.5 mm; ventral 3.6 mm). Behavioral experiments were performed 2 weeks after the implantation. For microinjection of DA receptor antagonists into the mPFC or NAc lateral shell a guide cannula (PlasticOne, Roanoke, Va.) was implanted directly over the ipsilateral mPFC (bregma: 2.2 mm; lateral 0.3 mm; ventral −2.0 mm) or NAc lateral shell (bregma: 1.45 mm; lateral 1.75 mm; ventral 4.0 mm) of the mice in which RV-ChR2 injection into the VTA and the implantation of doric optic fibers were made. Optical fiber and cannula placements were confirmed in all animals. Although placements varied slightly from mouse to mouse, behavioral data from all mice were included in the study.

Electrophysiology.

Mice were deeply anaesthetized with pentobarbital (200 mg/kg ip; Ovation Pharmaceuticals, Deerfield, Ill.). Coronal midbrain slices (250 μm) were prepared after intracardial perfusion with ice-cold artificial cerebrospinal fluid (ACSF) containing elevated sucrose (in mM): 50 sucrose, 125 NaCl, 25 $NaHCO_3$, 2.5 KCl, 1.25 $NaH_2PO_4$, 0.1 $CaCl_2$, 4.9 $MgCl_2$, and 2.5 glucose (oxygenated with 95% $O_2$/5% $CO_2$). After 90 min of recovery, slices were transferred to a recording chamber and perfused continuously at 2-4 ml/min with oxygenated ACSF (125 NaCl, 25 $NaHCO_3$, 2.5 KCl, 1.25 $NaH_2PO_4$, 11 glucose, 1.3 $MgCl_2$, and 2.5 $CaCl_2$) at ~30° C. For recording of excitatory postsynaptic currents (EPSCs) picrotoxin (50 μM, Sigma) was added to block inhibitory currents mediated by $GABA_A$ receptors. The internal solution contained (in mM): 117 $CsCH_3SO_3$, 20 HEPES, 0.4 EGTA, 2.8 NaCl, 5 TEA, 4 MgATP, 0.3 NaGTP, 5 QX314, 0.1 Spermine, and 0.1% neurobiotin. For recording of inhibitory postsynaptic currents (IPSCs) the internal solution contained (in mM): 130 CsCl, 1 EGTA, 10 HEPES, 2 MgATP, 0.2 NaGTP, and 0.1% neurobiotin (for both internal solutions pH 7.35, 270-285 mOsm). Patch pipettes (3.8-4.4 MΩ) were pulled from borosilicate glass (G150TF-4; Warner Instruments).

Labeled DA neurons were visualized with a 40× water-immersion objective on an upright fluorescent microscope (BX51WI, Olympus USA) equipped with infrared-differential interference contrast (IR-DIC) video microscopy and epifluorescence (Olympus USA) for detection of retrobeads. ChR2 was stimulated by flashing 473 nm light (5 ms pulses; 0.1 Hz; 1-2 mW) through the light path of the microscope using a ultrahigh-powered LED powered by an LED driver (Prizmatix, Modiin Ilite, Israel) under computer control. The light intensity of the LED was not changed during the experiments and the whole slice was illuminated. A dual lamp house adapter (Olympus USA) was used to switch between fluorescence lamp and LED light source. Excitatory postsynaptic currents (EPSCs) were recorded in whole-cell voltage clamp (Multiclamp 700B, Molecular Devices, CA, USA), filtered at 2 KHz, digitized at 10 KHz (ITC-18 interface, HEKA) and collected on-line using custom Igor Pro software (Wavemetrics, Lake Oswego, Oreg., USA). Series resistance (15-25 MΩ) and input resistance were monitored on-line with a 4 mV hyperpolarizing step (50 ms) given with each afferent stimulus. VTA/SN and RMTg neurons were voltage-clamped at −70 mV and EPSC or IPSC amplitudes were calculated by measuring the peak current from the average EPSC or IPSC response from 10-15 consecutive sweeps.

For pharmacological characterization light-evoked EPSCs or IPSCs were recorded for 5 min followed by bath perfusion of 10 μM CNQX (Tocris Bioscience, Ellisville, Mich., USA) or 50 μM picrotoxin (Sigma) for an additional 10 min, respectively. 10-15 consecutive sweeps pre- and post-drug were averaged and peak EPSCs or IPSCs amplitudes were then measured. For detection of IPSCs, DA cells were recorded from the caudal VTA in slices that contained the RMTg. For determination of DA or GABAergic phenotype, neurons were filled with neurobiotin (Vector, Burlingame, Calif., USA) during the patch clamp experiment, then fixed in 4% PFA and 24 h later immunostained for TH or GAD67. Approximately 80% of all whole-cell patch clamped neurons could be successfully recovered. The DA phenotype or GABAergic phenotype (in the RMTg) was confirmed in all of these neurons.

Immunohistochemistry. Immunohistochemistry and confocal microscopy were performed as described previously[4,5]. Briefly, after intracardial perfusion with 4% paraformaldehyde in PBS, pH 7.4, the brains were post-fixed overnight and coronal midbrain slices (50 or 100 μm) were prepared. The primary antibody used were mouse anti-tyrosine hydroxylase (TH) (1:1000; Millipore, Temecula, Calif., USA), rabbit anti-tyrosine hydroxylase (TH) (1:1000; Calbiochem, San Diego, Calif., USA), rabbit anti-PHA-L (1:1000; Vector, Burlingame, Calif., USA), goat anti-glutamate transporter (EAAC1; 1:1000; Millipore), rabbit anti-ChAT (1:200; Millipore), mouse anti-GAD67 (clone 1G10.2; 1:500; Millipore), rabbit anti-c-fos (1:500, Calbiochem) and rabbit anti-NeuN (1:1000; Millipore). The secondary antibodies used were Alexa Fluor488 anti-rabbit, AlexaFluor546 anti-goat, AlexaFluor546 anti-rabbit, AlexaFluor546 anti-mouse, Alexa Fluor647 anti-rabbit, Alexa Fluor647 anti-mouse (all 1:750), AlexaFluor488 streptavidin (1:1000) (all Molecular Probes, Eugene, Oreg.). Image acquisition was performed with a confocal system (Zeiss LSM510) using 10×, 40× or 63× objectives and on a Zeiss Axiolmager M1 upright widefield fluorescence/DIC microscope with CCD camera using 2.5× and 10× objectives. Images were analyzed using the Zeiss LSM Image Browser software and ImageJ software.

Figure 14A:
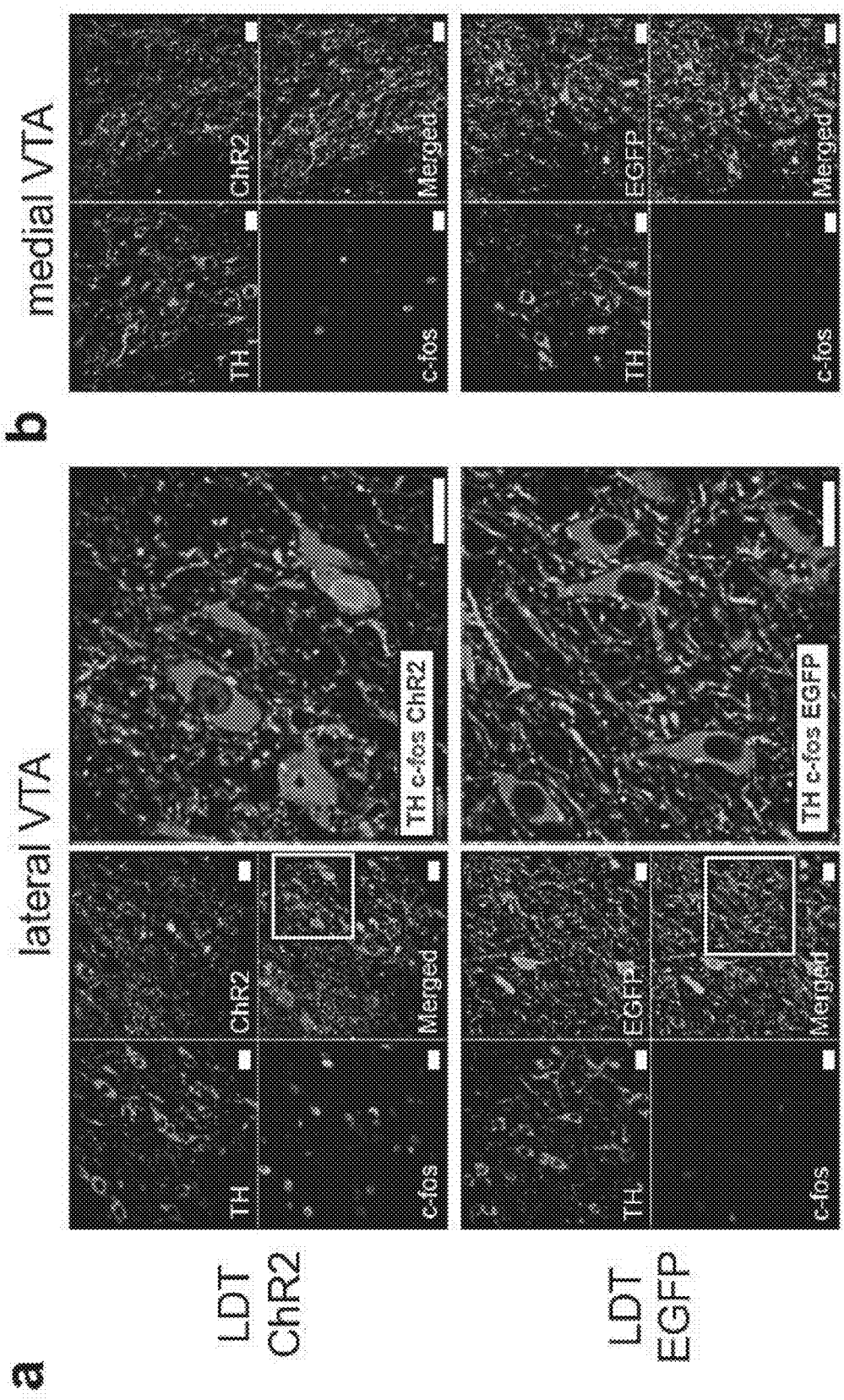
Figure 14B:
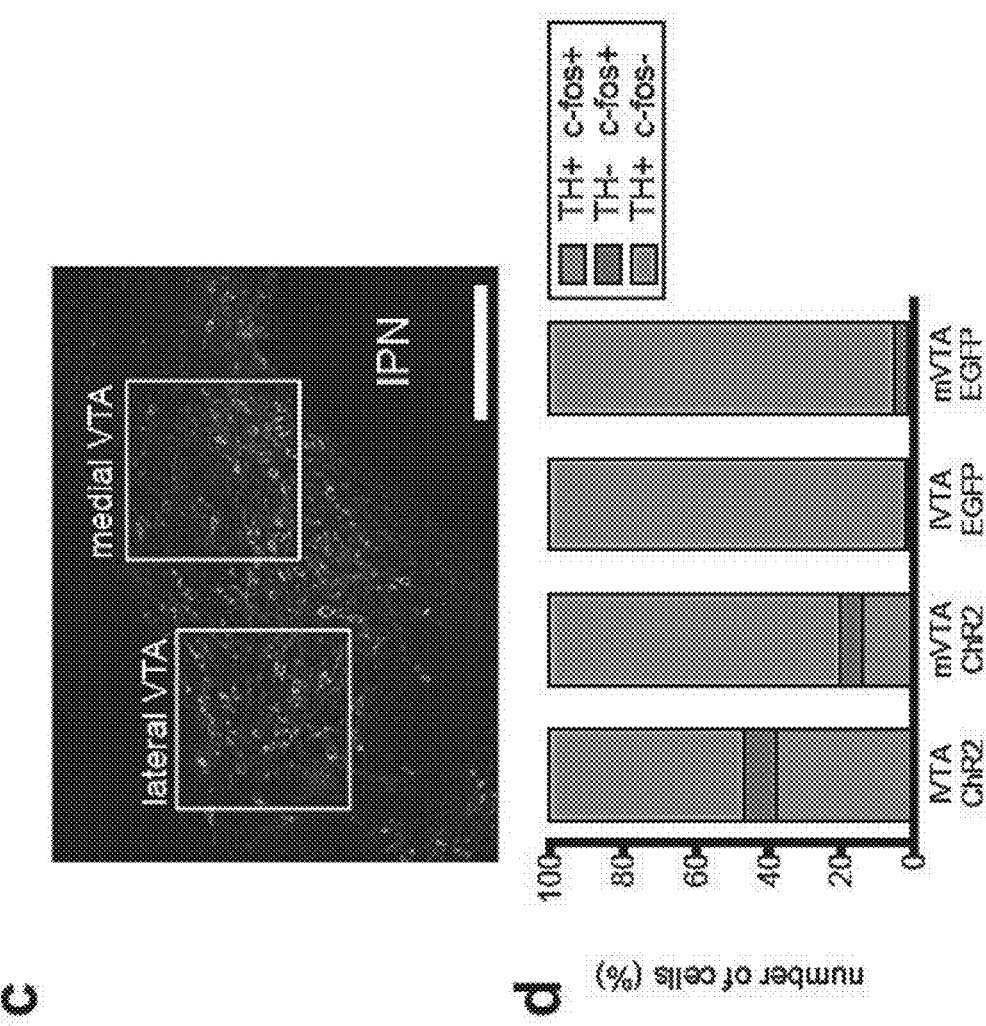
Figure 14C:
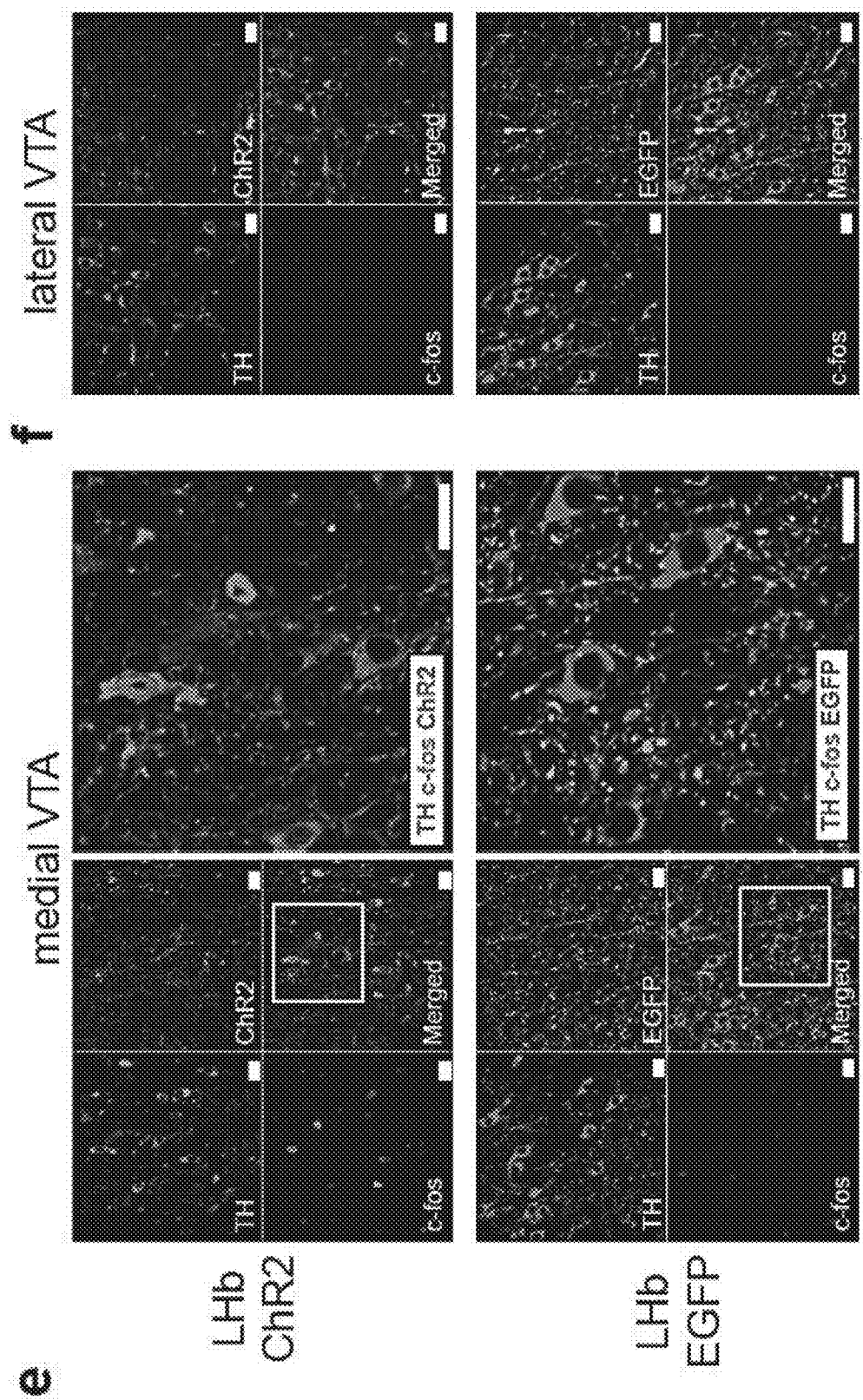

For quantification of ChR2-EYFP fluorescence intensity and quantification of c-fos-positive cells, confocal images were acquired using identical pinhole, gain, and laser settings. Images in the medial and lateral VTA as well as the SN from the same tissue sections were acquired at the same focus level. The medial and lateral VTA was defined as the area that corresponds to the anatomical location of distinct DA subpopulations[4,5]. The medial VTA was defined as the region comprising the medial paranigral nucleus (PN) and medial parabrachial pigmented nucleus (PBP), while the lateral VTA was defined as the lateral parabrachial pigmented nucleus (FIG. 14). No additional post-processing was performed on any of the collected images. ChR2 fluorescence intensity was then quantified using a scale from 0-255 in ImageJ to determine the mean intensity across the entire image. For retrobead, AAV and PHA-L injections as well as RV injections in the mPFC and NAc lateral shell the injection-sites were confirmed in all animals by preparing coronal sections (100 µm). Counterstaining of injection sites was performed with green or red Nissl (NeuroTrace 500/525 or 530/615, Molecular Probes, Eugene, Oreg.).

We routinely carried out complete serial analyses of the injection sites Animals with significant contaminations outside target areas were discarded (see Lammel et al., 2008[4] for serial analysis of retrobead injection-sites and definition of DA target areas). For RV injections into the VTA we confirmed that all animals had the center of the viral injection located in the caudal VTA (Bregma −3.4 mm). However, quantification of the "spread" of the RV-ChR2 injected into the VTA is difficult because for expression of the transgene, the RV must be taken up by terminals and the transgene must be synthesized in the cytosol and then transported within the axons. Any EYFP within the VTA and adjacent structures will represent axons/terminals of cells that project to the VTA and adjacent structures as well as the cell bodies of neurons (i.e. RMTg) that have local connectivity within the VTA and adjacent structures. Thus transgene expression in structures adjacent to the VTA does not indicate that LHb or LDT neurons project to these structures. Nevertheless, in FIG. 21 we present a serial reconstruction for the caudo-rostral extent of the midbrain showing the expression of ChR2-EYFP one week after injection of RV-ChR2 into the VTA (n=5 mice). TH-stained coronal midbrain sections (100 µM) were prepared from the injected mice and reconstructed using Neurolucida software (Micro-Brightfield, Colchester, Vt.). Sections were labeled relative to bregma using landmarks and neuroanatomical nomenclature as described in the Franklin and Paxinos mouse brain atlas (2001). We report all brain areas in which detectable EYFP was observed. The strongest transgene expression was observed in the caudal VTA and several of its distinct subnuclei, most commonly in the interpeduncular nucleus (IPN). We also always detected high transgene expression in the RMTg. Thus when referred to in the text, the VTA includes the RMTg, which was originally termed the "tail of the VTA"[22].

Figure 22A:
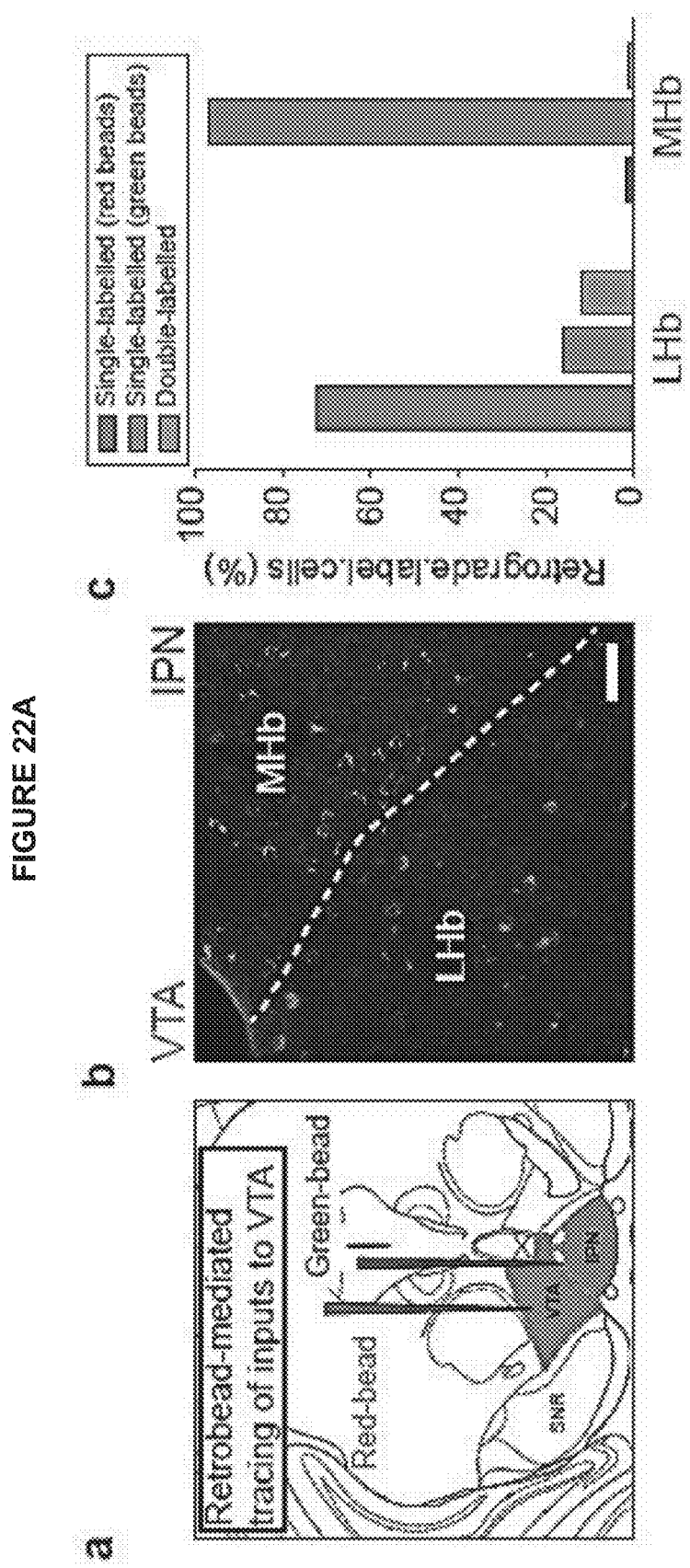
FIGS. 22A-B depict retrobead injections into the VTA or IPN and quantification of connectivity.
Figure 22B:
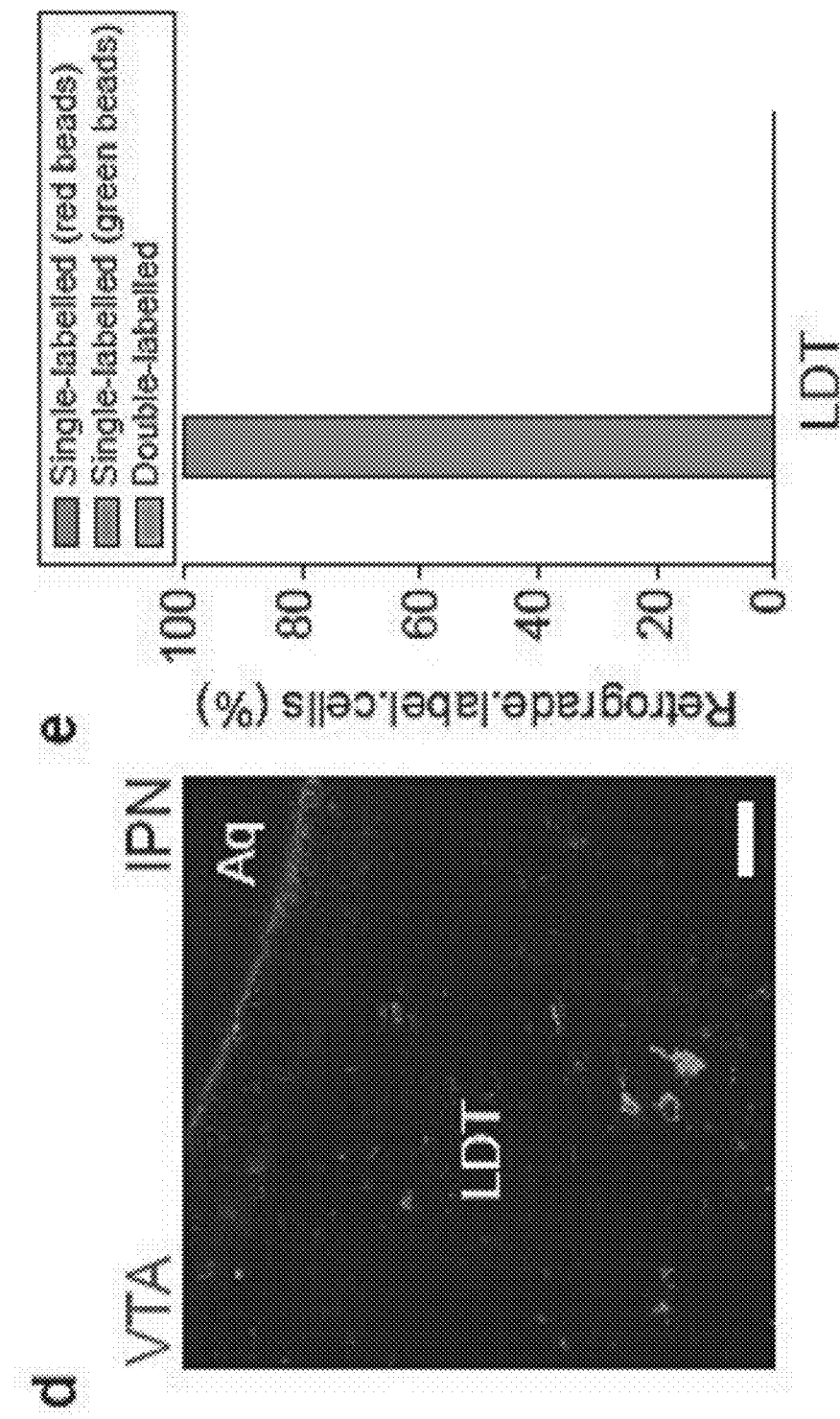

Because the IPN expressed ChR2-EYFP following intra-VTA injections, we conducted additional double retrograde tracing experiments in which we injected small amounts of green Retrobeads (20 nl; LumaFlauor Inc., Naples, Fla.) into the IPN (bregma −3.9 mm; lateral 0 mm; ventral 4.55 mm) and red Retrobeads (60 nl; LumaFlauor Inc., Naples, Fla.) into the VTA (bregma −3.4 mm; lateral 0.35 mm; ventral 4.0 mm). Fluorescently-labeled latex Retrobeads were used in these experiments (n=2 mice) because they show very limited diffusion from the injection site even after several weeks in vivo and thus can be highly localized. While a large number of cells in the lateral habenula contained red beads (~84%, 79/94 cells), confirming a projection from this structure to the VTA, only a small proportion of these cells (~12%, 11/94 cells) also contained green beads (FIG. 22). In contrast, a large number of medial habenula cells contained green beads (~98%, 214/218 cells) and less than 2% (3/218 cells) of these also contained red beads (FIG. 22), demonstrating that the medial habenula preferentially projects to the IPN. In the LDT, many cells (>100) contained red beads and none of these cells contained green beads (FIG. 22). These results suggest that LDT cells likely only project to VTA and not the IPN while the proportion of LHb neurons that project to the IPN in addition to the VTA is small.

Figure 21A:
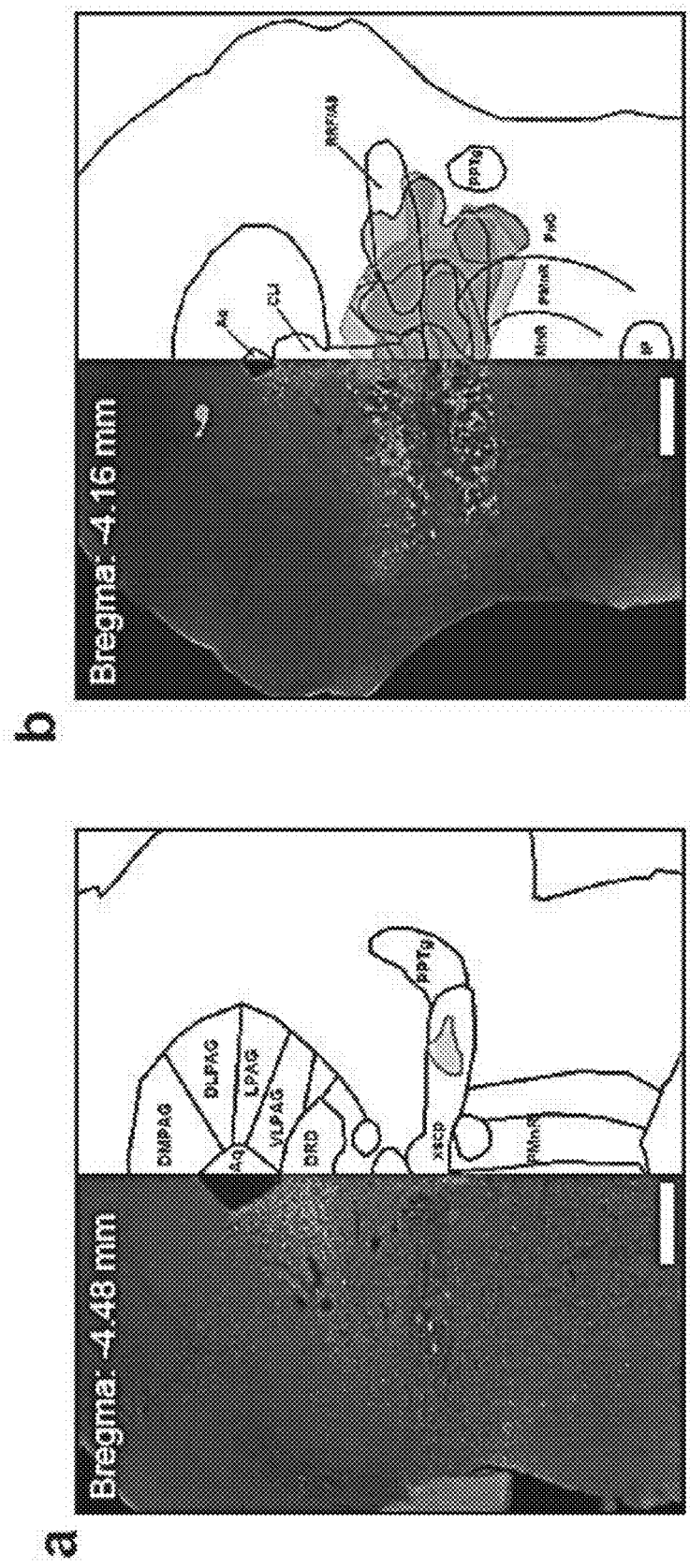
Figure 21C:
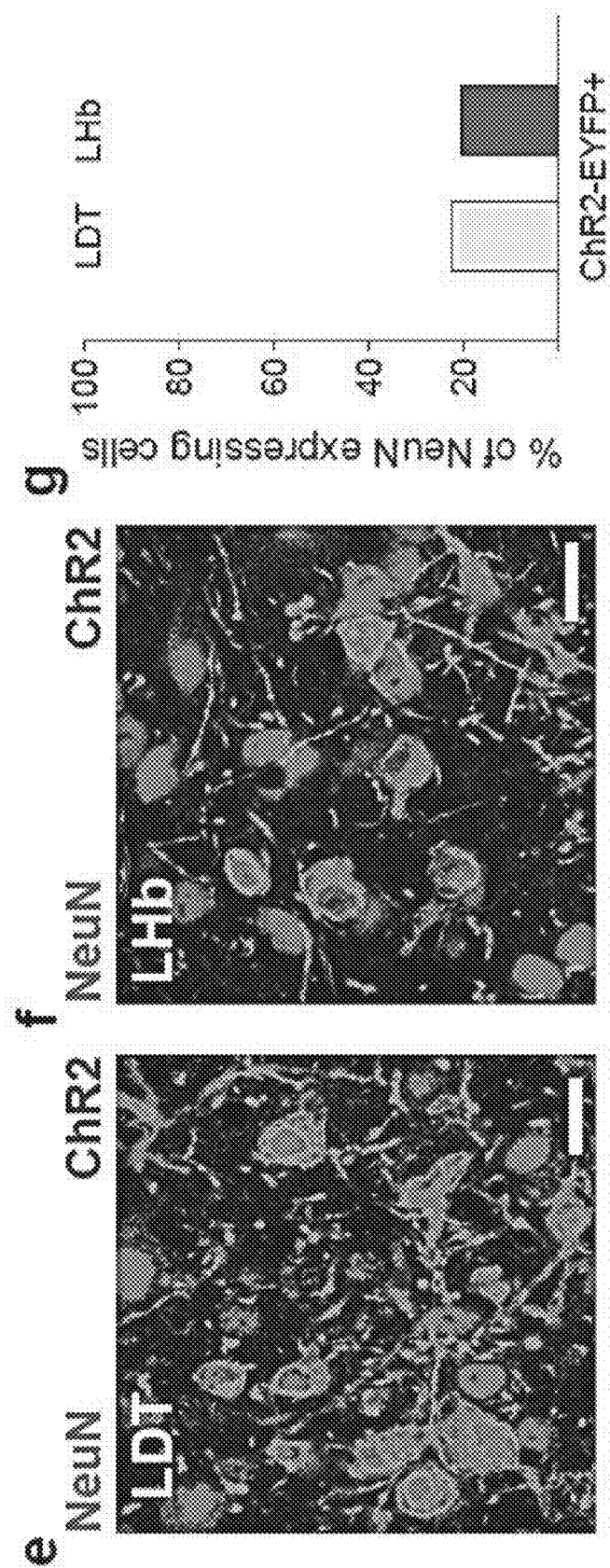

For quantification of the expression of RV-ChR2-EYFP in the LDT and LHb 50 µm coronal sections from mice which had been injected with RV-ChR2-EYFP in the VTA were stained for NeuN. 66 confocal images from the LDT and 55 confocal images from the LHb were obtained using a 40× objective (n=3 mice). The percent of ChR2-EYFP-positive cells relative to the number of NeuN-positive cells in a 125 µm×125 µm area was analyzed using the ImageJ software. Approximately 20% of all NeuN-positive LDT and LHb neurons expressed ChR2-EYFP following RV-ChR2 injection into the VTA (FIG. 21).

Behavioral Assays.

All behavioral tests were conducted during the same circadian period (13:00-19:00). The conditioned place preference (CPP) and aversion (CPA) protocols were performed in a rectangular cage with a left chamber measuring 28 cm×24 cm with black and white stripes on the walls and a metal grill floor, a center chamber measuring 11.5 cm×24 cm with white walls and a smooth plastic floor; and a right chamber measuring 28 cm×24 cm with black and white squares on the walls and a punched metal floor. The apparatus was designed so that mice did not have any consistent bias for a particular chamber (FIG. 10). The CPP/CPA test consisted of 3 sessions over 3 days. On day 1 (1 week after infusion of RV-EGFP or RV-ChR2 into the VTA), individual mice were placed in the center chamber and allowed to freely explore the entire apparatus for 15 min (pre-test). On day 2 mice were confined to one of the side chambers for 30 min during optical stimulation. Stimulation in left or right chambers was counter-balanced across mice. For stimulation the optical fiber was connected to a 473 nm laser diode (OEM Laser Systems, East Lansing, Mich.) through an FC/PC adapter. Laser output was controlled using a Master-8 pulse stimulator (A.M.P.I., Jerusalem, Israel) which delivered 8 pulses of 5 ms light flashes at 30 Hz every 5 s (phasic stimulation) or 5 ms light flashes delivered at 1 Hz (low frequency stimulation). For stimulation of LDT and LHb axon terminals in the VTA 15 pulses of 5 ms light flashes at 30 Hz every 2 s were delivered. Light output through the optical fibers was adjusted to 20 mW using a digital power meter console (Thorlabs, Newton, N.J.) and was checked before and after stimulation of each mouse. On day 3, similar to day 1, mice were placed in the center chamber and allowed to freely explore the entire apparatus for 15 min (Post-Test 1). After Post-Test 1 the blue light laser was switched on and the mouse received phasic or low frequency stimulation for whenever it was in the chamber in which it had been conditioned on day 2 for a total duration of 15 min (Post-Test 2). There was no interruption between Post-Test 1 and Post-Test 2. A video tracking system (BiObserve, Fort Lee, N.J.) recorded all animal movements. To calculate preference or aversion during Post-Test 1, we divided the relative time (in %) the mouse spent during Post-Test 1 in the conditioned chamber (i.e. the chamber in which it received either phasic or low frequency light stimulation of LDT or LHb inputs to the VTA) by the relative time (in %) the mouse spent in this chamber during the Pre-test (Post-Test 1/Pre ratio). During Post-Test 2, preference or aversion was calculated by dividing the relative time (in %) the mouse spent during Post-Test 2 in the conditioned chamber by the relative time (in %) the mouse spent in this chamber during the Pre-test (Post-Test 2/Pre ratio).

For microinjection of the D1 dopamine receptor antagonist SCH23390 into mPFC and the microinjection of the D1 and D2 dopamine receptor antagonists SCH23390 and raclopride into the NAc lateral shell a 33-gauge injector cannula connected to a syringe pump (Harvard Apparatus, MA) was inserted into the guide cannula which had been implanted in the mPFC or NAc lateral shell. All microinjections were delivered at a rate of 100 nl/min. Injector cannulas remained in place for an additional minute before being removed. Drugs were infused 5 min before the beginning of the light stimulation on day 2. For the pharmacological control experiments, the animals were treated identically except no optical stimulation was provided, Doses of drugs used for microinjections were: 50 ng SCH23390 in 0.2 μl saline (mPFC); 300 ng SCH23390 and 3 μg, raclopride in 0.3 μl saline/DMSO (NAc lateral shell).

The open field test was conducted on different cohorts of mice to measure the effect of optogenetic stimulation on anxiety-like responses and general locomotor ability. The mice were placed in the chamber (50×50 cm) and their movement was recorded and analyzed for 18 min using the same video-tracking software that was used in the CPP/CPA tests (BiObserve, Fort Lee, N.J.). After three minutes without optical stimulation, phasic stimulation was turned on for 3, three min epochs interspersed with 3 min epochs of no stimulation. For all analyses and graphs where total "off" and "on" conditions are displayed, the 3 "off" epochs were pooled and the 3 "on" epochs were pooled. The inner zone of the open field chamber was defined as the 23×23 cm central square area.

For quantification of c-fos immunreactivity, LDT and LHb inputs to the VTA were stimulated for 30 min using the phasic light stimulation protocol. During this time the mice remained in their home cage. The mice were perfused with 4% PFA 60 min after the in vivo light stimulation and 24 h later immunohistochemistry was performed.

Statistics.

Student's t tests, Mann-Whitney U-tests or one-way ANOVA tests were used to determine statistical differences using GraphPad prism 5 (Graphpad Software, San Diego, Calif.). Bonferroni post hoc analysis was applied, when necessary, to compare means. Statistical significance was set at $p<0.05$ (*), $p<0.01$ (), $p<0.001$ (*). All data values are presented as means±SEM.

38. Zhang, F., et al. Optogenetic interrogation of neural circuits: technology for probing mammalian brain structures. *Nat. Protoc.* 5, 439-456 (2010).
39. Mebatsion, T., Konig, M. & Conzelmann, K. K. Budding of rabies virus particles in the absence of the spike glycoprotein. *Cell* 84, 941-951 (1996).
40. Wickersham, I. R., Sullivan, H. A. & Seung, H. S. Production of glycoprotein-deleted rabies viruses for monosynaptic tracing and high-level gene expression in neurons. *Nat. Protoc.* 5, 595-606 (2010).

Results

Inputs to the VTA from LDT and LHb

Figure 7:
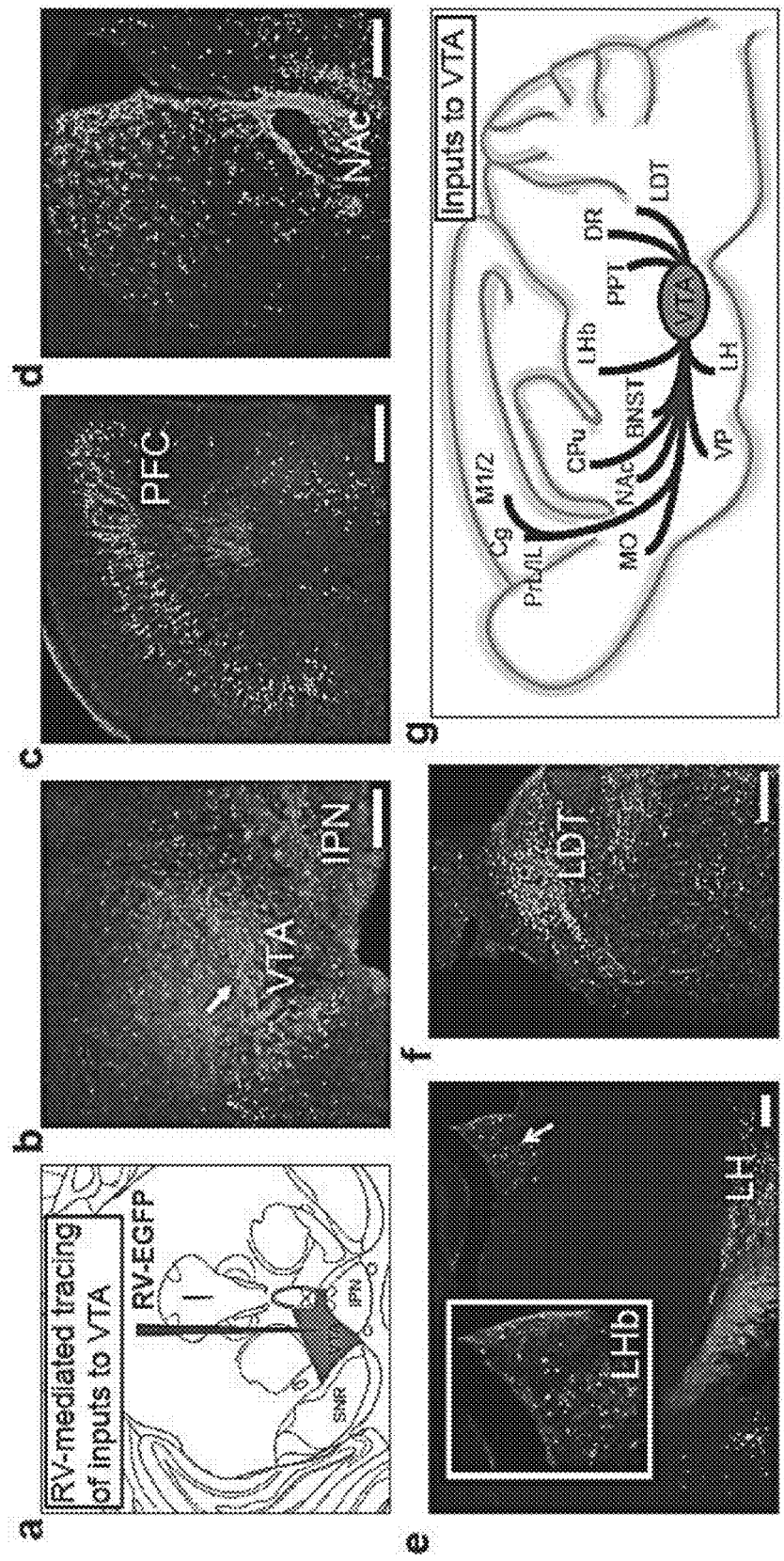
FIG. 7 depicts inputs to the VTA.
Figure 8:
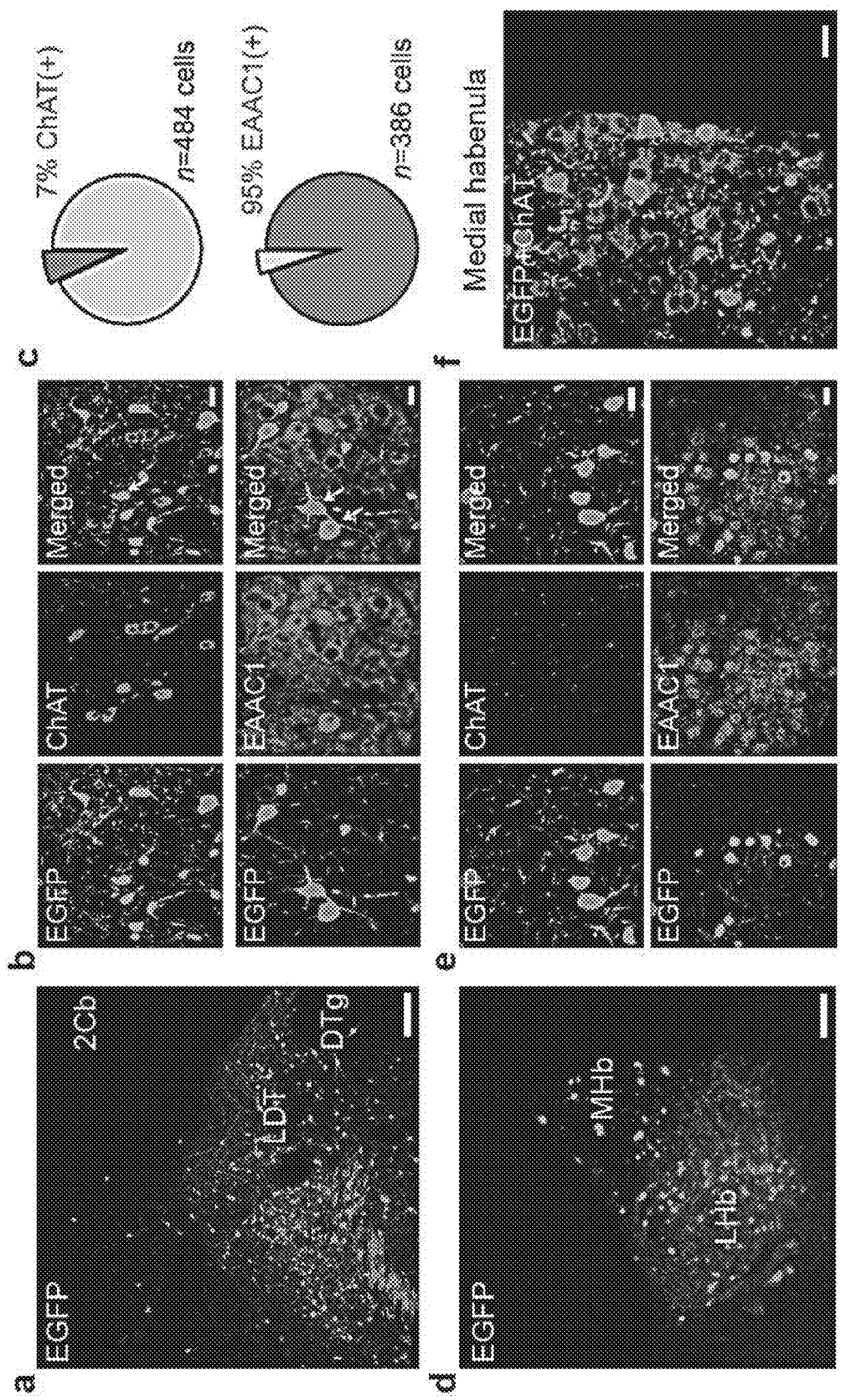
FIG. 8 depicts the mainly glutamatergic LDT and LHb neurons that project to the VTA.

To identify unambiguously the afferent inputs to the VTA, we used a rabies virus in which the glycoprotein is replaced by EGFP(RV-EGFP)[16]. Consistent with recent results[17], injection of RV-EGFP into the VTA resulted in expression of EGFP in diverse brain areas with large clusters of EGFP-expressing cells in the PFC, NAc, lateral hypothalamus, LHb and LDT (FIG. 7). We focused on inputs to the VTA from the LDT and LHb because both play roles in motivated behaviors by influencing VTA neuronal activity and the consequent release of DA in target structures[2,7,18]. EGFP-positive LDT neurons expressed markers for both glutamatergic neurons (the glutamate transporter EAAC1) and cholinergic neurons (choline acetyltransferase; ChAT) (FIG. 8)[19,20]. However, while 95% of LDT neurons projecting to VTA expressed EAAC1, only ~7% expressed ChAT. LHb neurons are excited by the absence of an expected reward[18] and likely send direct inputs to GABAergic cells in the tail of the VTA, the rostromedial tegmental nucleus (RMTg)[21, 22], that inhibit VTA DA neurons[23-26]. EGFP-positive LHb neurons were immunopositive for EAAC1 but not for ChAT (FIG. 8) indicating that LHb neurons projecting to VTA are glutamatergic[8].

Figure 9:
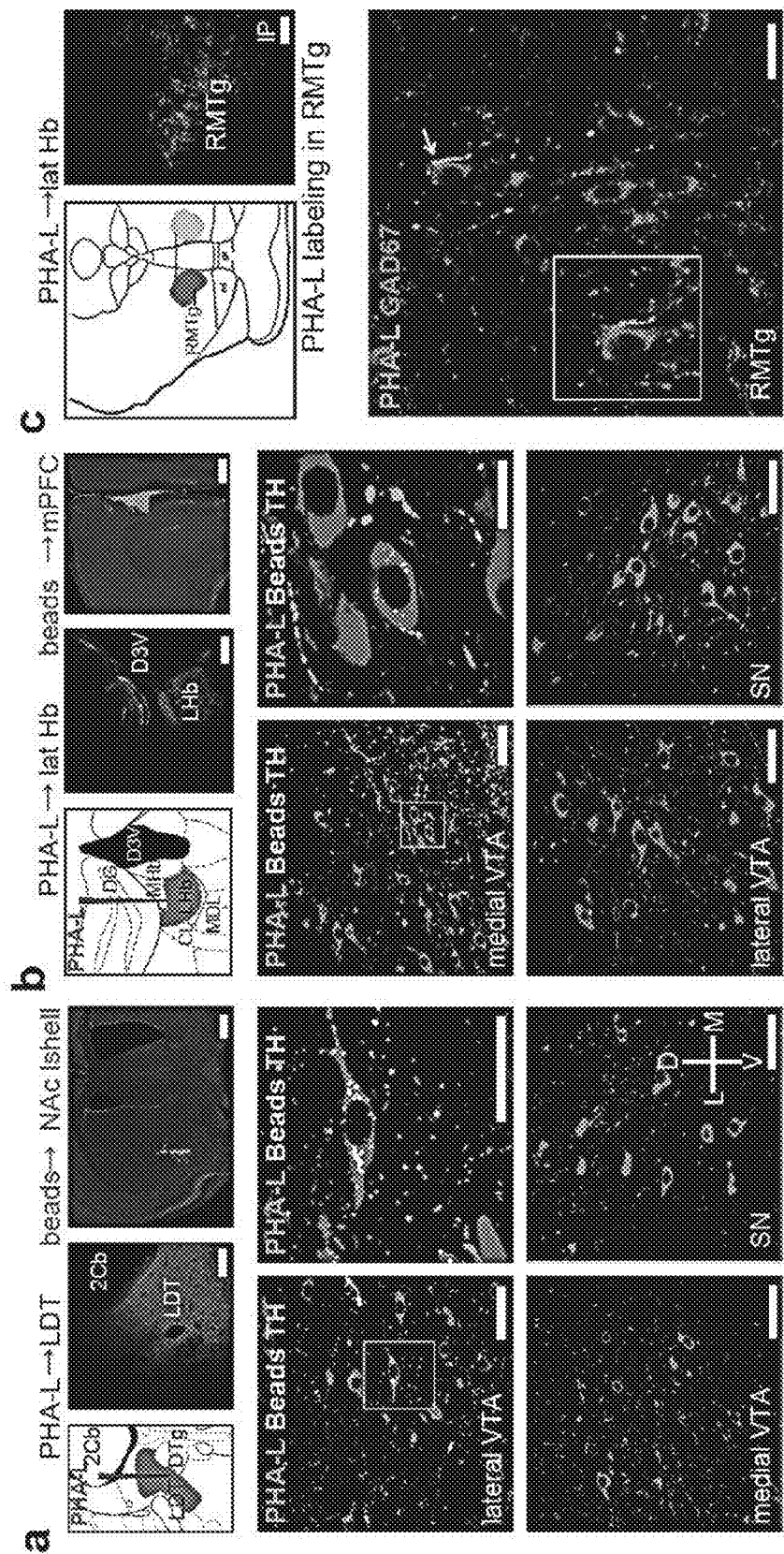
FIG. 9 depicts the LDT and LHb terminals in the VTA.

To visualize fibers within the VTA from LDT and LHb we injected the anterograde tracer *Phaseolus vulgaris leucoagglutinin* (PHA-L). It was apparent that the density of LDT and LHb inputs differed between VTA subregions in which different subpopulations of DA neurons reside[4, 5]. To test this conclusion, we simultaneously retrogradely labeled DA projection neurons and anterogradely labeled LDT or LHb fibers (FIG. 1). Injection of PHA-L into LDT and RV expressing tdTomato (RV-tdTomato) into NAc lateral shell (FIG. 1) revealed that RV-tdTomatocells were predominantly located in lateral VTA (FIG. 1) that in close proximity contained LDT terminals as well as TH-immunopositive processes (FIG. 1). More modest PHA-L labeling was observed in medial VTA (FIG. 1) and substantia nigra (SN; FIG. 1). In contrast, injection of PHA-L into LHb and RV-tdTomato into mPFC (FIG. 1) revealed RV-tdTomatocells mainly in medial VTA (FIG. 1) in close proximity to LHb terminals and TH-immunopositive processes (FIG. 1, 1). There was minimal PHA-L labeling of LHb inputs in the lateral VTA (FIG. 1) or SN (FIG. 1) but as expected[21, 22] PHA-L terminals were present in RMTg adjacent to GABAergic neurons (FIG. 9). In additional experiments, we injected fluorescent retrobeads into NAc lateral shell or mPFC and labeled LDT or LHb inputs with PHA-L, respectively. A similar anatomical distribution of pre- and post-synaptic elements was observed (FIG. 9).

Input Specific Control of Reward and Aversion

Figure 2:
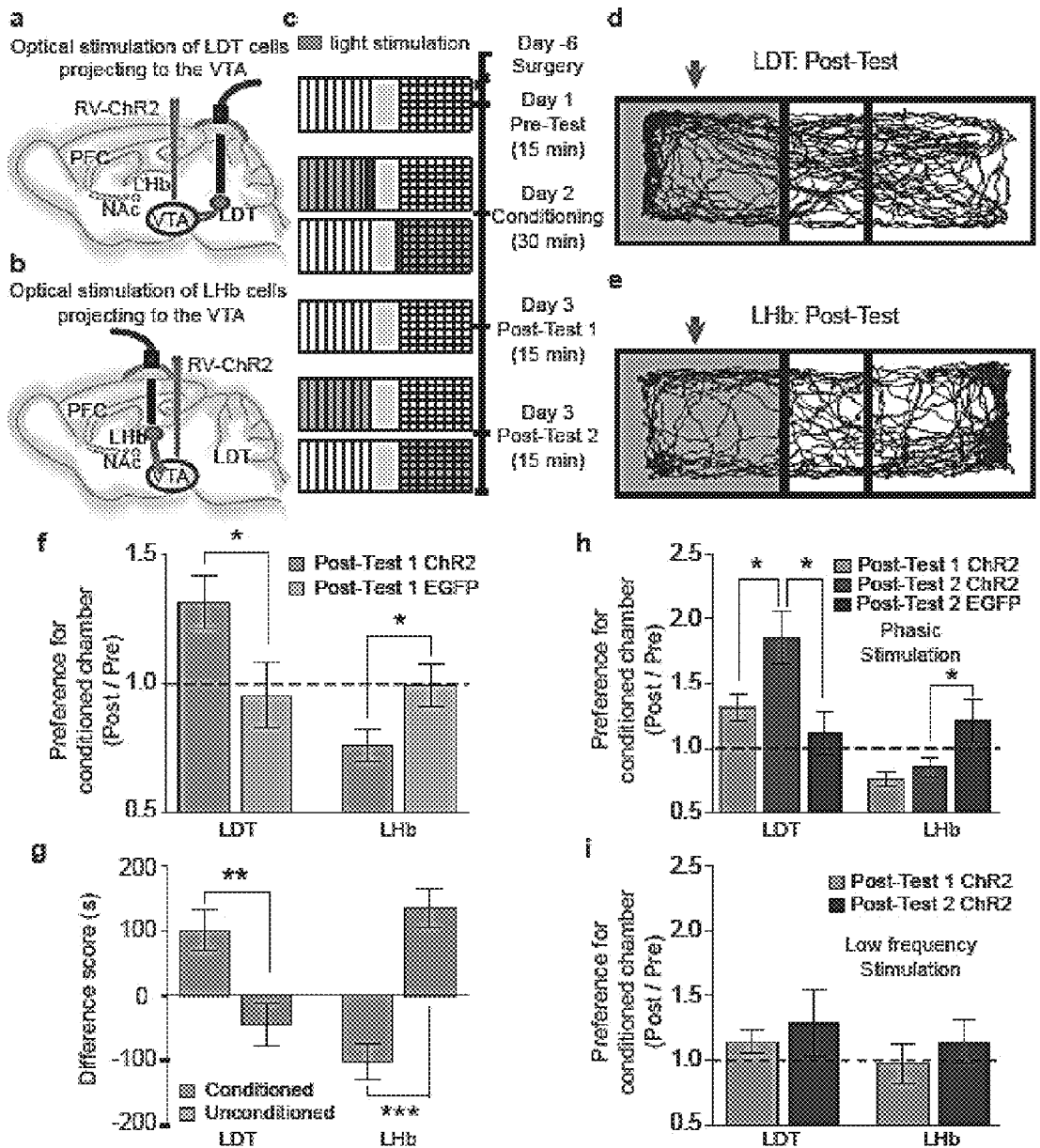
FIG. 2 depicts conditioned place preference/aversion following stimulation of LDT and LHb inputs to VTA.

These anatomical results suggest that LDT and LHb inputs preferentially terminate in different VTA subregions adjacent to DA neuron subpopulations that project to different target structures (NAc lateral shell versus mPFC) and may subserve different behavioral functions[5, 6]. To address functional differences in these inputs, we generated a RV expressing the light-activated ion channel ChR2 fused to enhanced yellow fluorescent protein (EYFP, RV-ChR2) (FIG. 10) and tested the consequences of activation of LDT-VTA and LHb-VTA pathways in a conditioned place preference (CPP) assay by injecting RV-ChR2 or RV-EGFP into VTA and implanting an optical fiber over LDT or LHb (FIG. 2). Using a three day protocol (FIG. 2), phasic stimulation of LDT neurons projecting to VTA on day 2 caused a strong CPP on day 3 (FIG. 2), while phasic stimulation of LHb neurons projecting to VTA caused a strong conditioned place aversion (CPA) (FIG. 2). Moreover, after the day 3 testing procedure (Post-Test 1), stimulating LDT neurons whenever animals were in the chamber in which they were conditioned on day 2 (Day 3, Post-Test 2) caused a further increase in CPP (FIG. 2) whereas stimulating LHb neurons did not further enhance CPA (FIG. 2). (See FIG. 11 for, non-normalized behavioral results.)

Figure 12A:
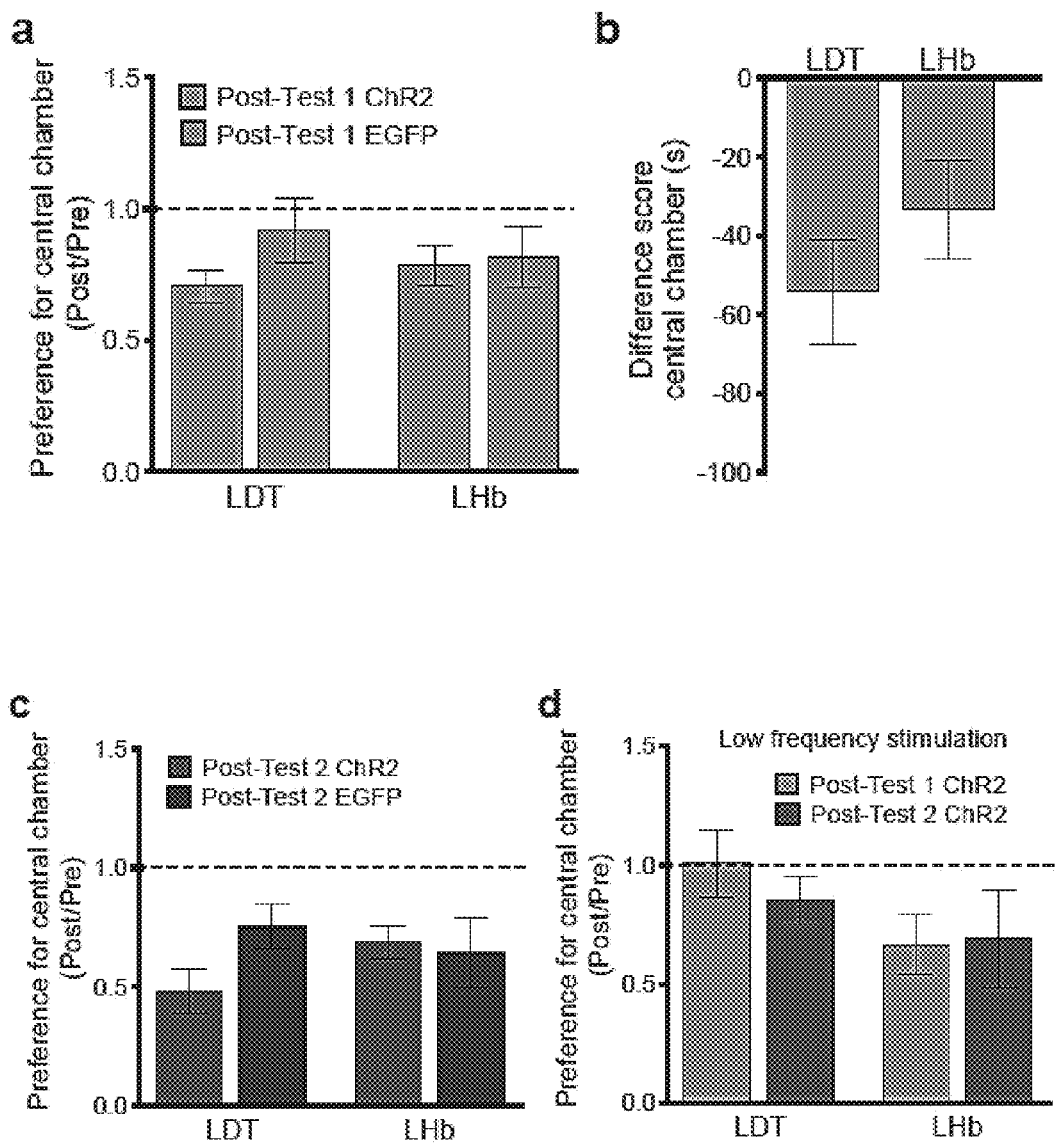
FIGS. 12A-B depict assays of locomotor activity and anxiety related to stimulation of LDT and LHb.
Figure 12B:
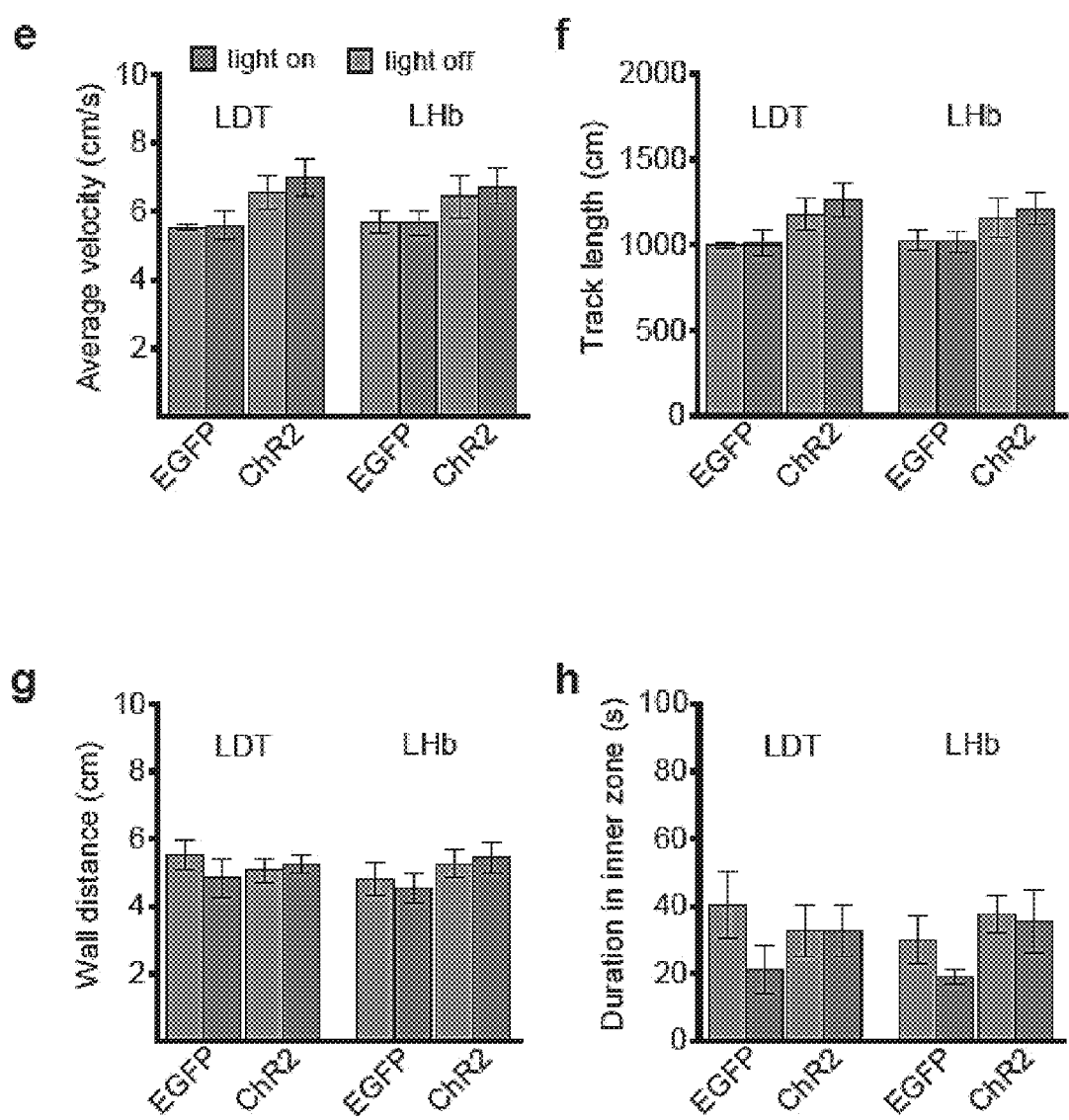
Figure 13A:
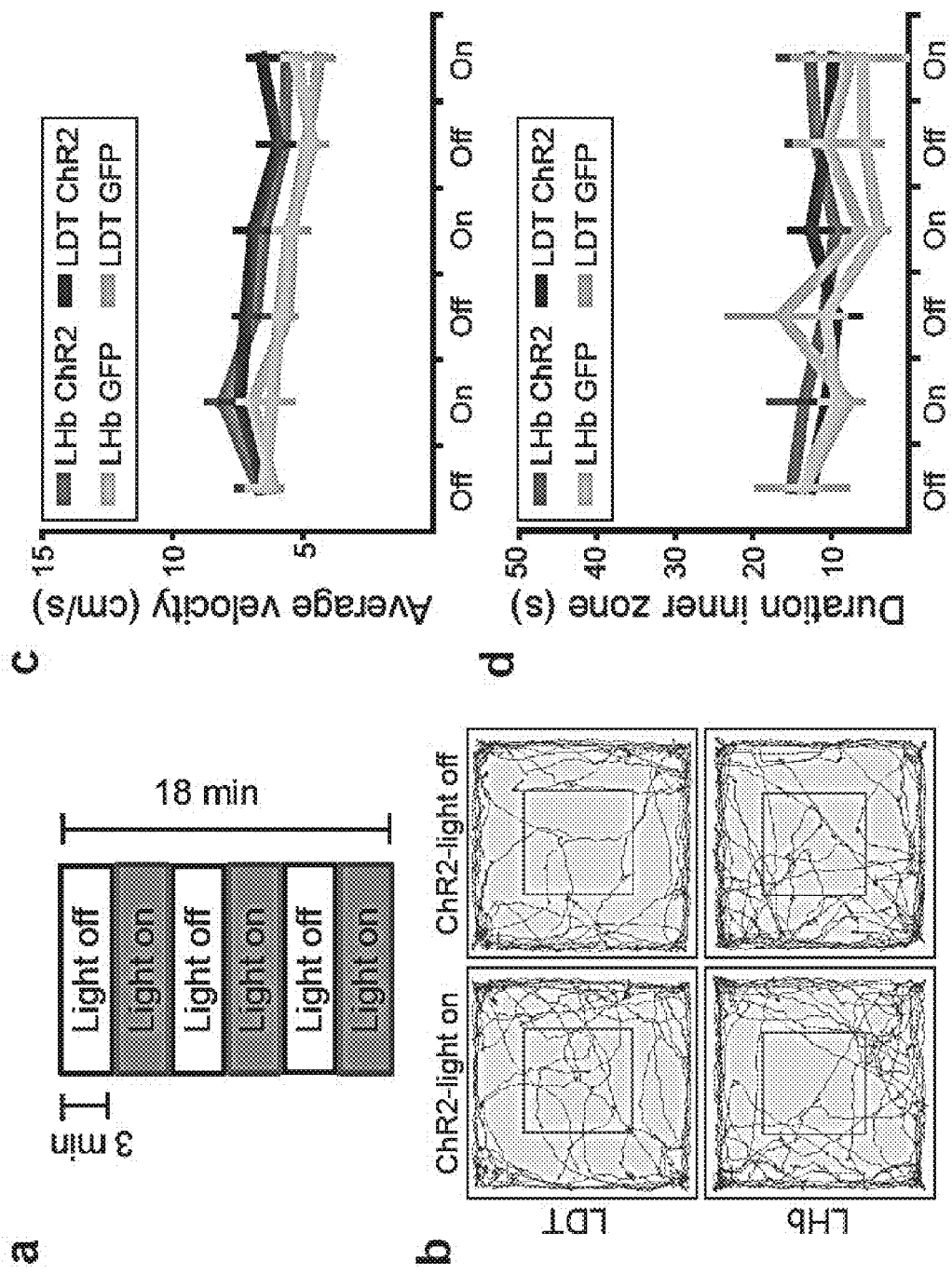

Additional results indicate that the effects of stimulating LDT and LHb neurons projecting to VTA were specific and due to driving activity in distinct populations of VTA neurons. First, animals that received intra-VTA injections of RV-EGFP exhibited no behavioral effects of phasic optical stimulation in LDT and LHb (FIG. 2; FIG. 11). Furthermore, low frequency stimulation of ChR2 in LDT and LHb had no effects in CPP/CPA assays (FIG. 2; FIG. 11). Second, non-stimulated animals showed no preference for either chamber (FIG. 10) and there was no effect of the optogenetic manipulations on time spent in the central chamber (FIG. 12). Third, stimulation of LDT and LHb neurons projecting to VTA had no effects on open field assays of anxiety or locomotor activity (FIG. 12, FIG. 13). Fourth, the placement of optical fiber in LDT and LHb was confirmed in all animals (FIG. 13). Fifth, VTA DA neuron activation following LDT and LHb stimulation was quantified by assaying the proportion of TH-immunopositive and TH-immunonegative neurons that expressed the activity-dependent immediate early gene c-fos (FIG. 14). Following LDT stimulation, ~40% of DA neurons in lateral VTA expressed c-fos whereas in medial VTA three-fold less DA neurons expressed c-fos. Activation of LHb inputs to the VTA caused an opposite pattern of c-fos expression: ~12% of DA neurons in medial VTA were c-fos-positive whereas <2% of DA neurons in lateral VTA expressed c-fos. Importantly, ~80% of non-DA neurons in the RMTg were c-fos-positive following LHb stimulation (FIG. 14).

Based on these results we hypothesized that LHb inputs drive DA neurons in the medial posterior VTA that project to mPFC[4-6]. To test this prediction, we activated LHb inputs to VTA in animals in which medial VTA neuron subpopulations that project to different targets were identified by the presence of fluorescent retrobeads (FIG. 14). In medial VTA, ~80% of neurons projecting to mPFC were c-fos-positive following LHb stimulation. In contrast, <10% of neurons projecting to NAc medial shell that are located in medial VTA[4-6] expressed c-fos following LHb stimulation.

Figure 15:
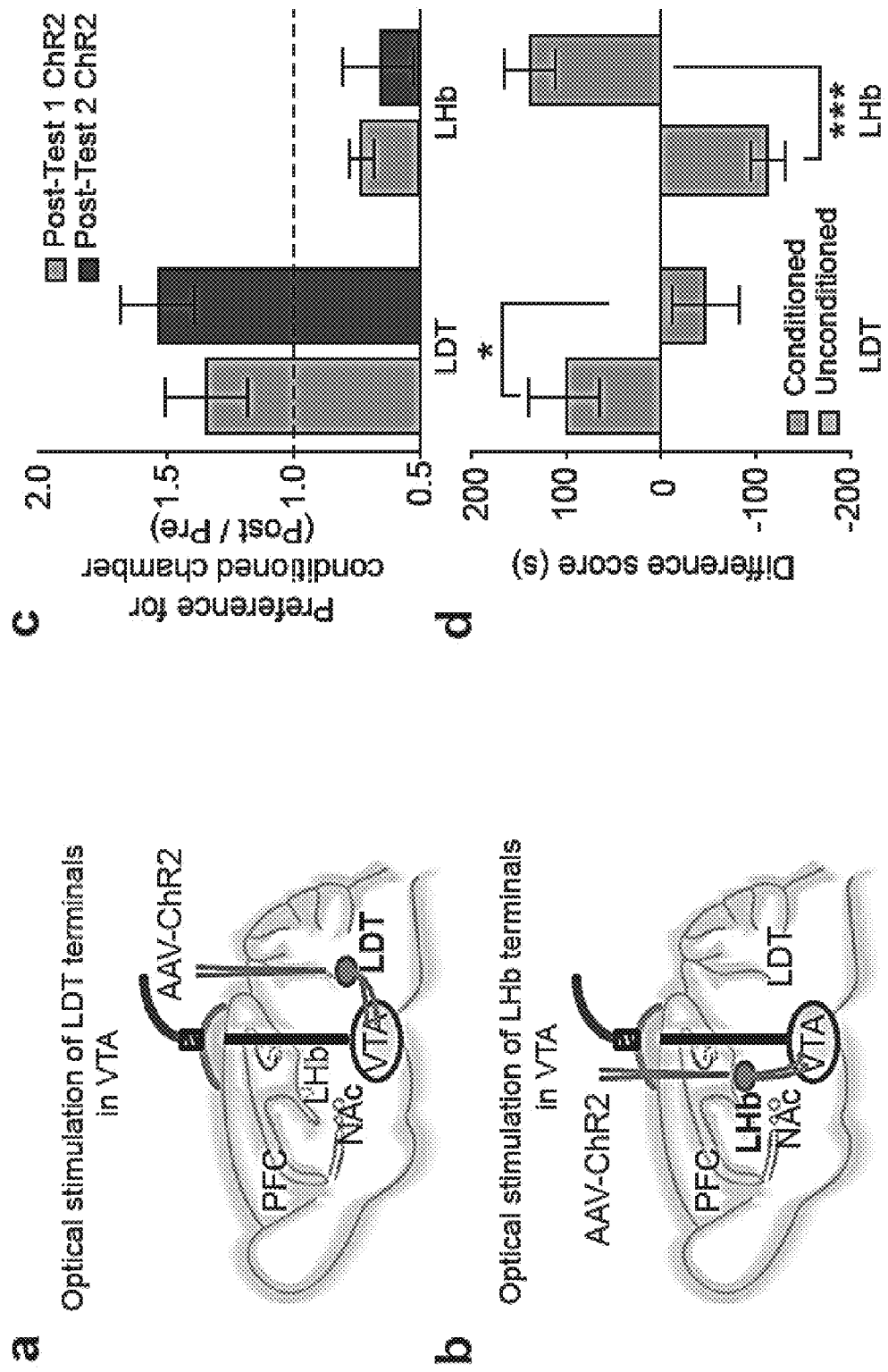
FIG. 15 depicts optical stimulation of axon terminals from LDT and LHb in VTA.
Figure 16:
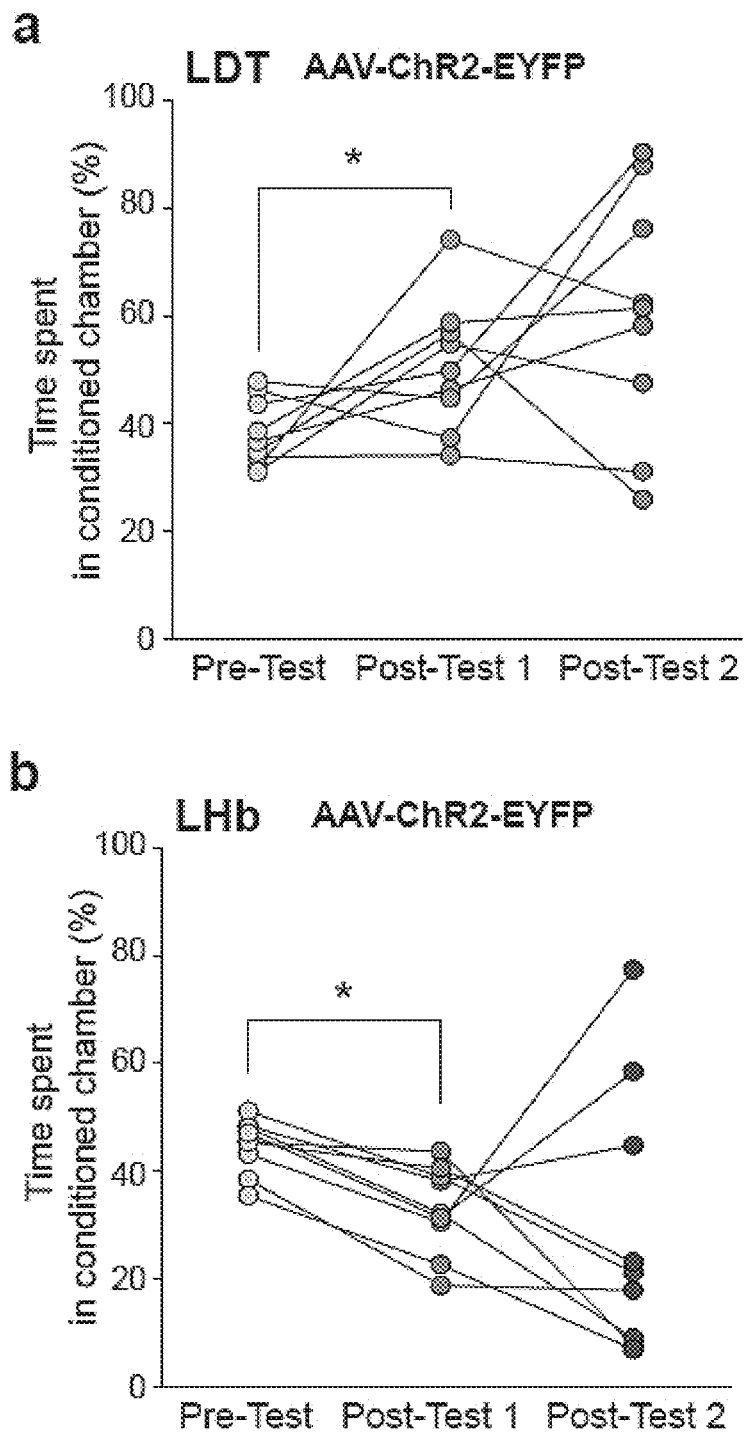
FIG. 16 depicts behavioral assays of mice in which AAV-ChR2 was injected into the LDT or Lhb and LDT or LHb axon terminals in the VTA were stimulated.
Figure 17B:
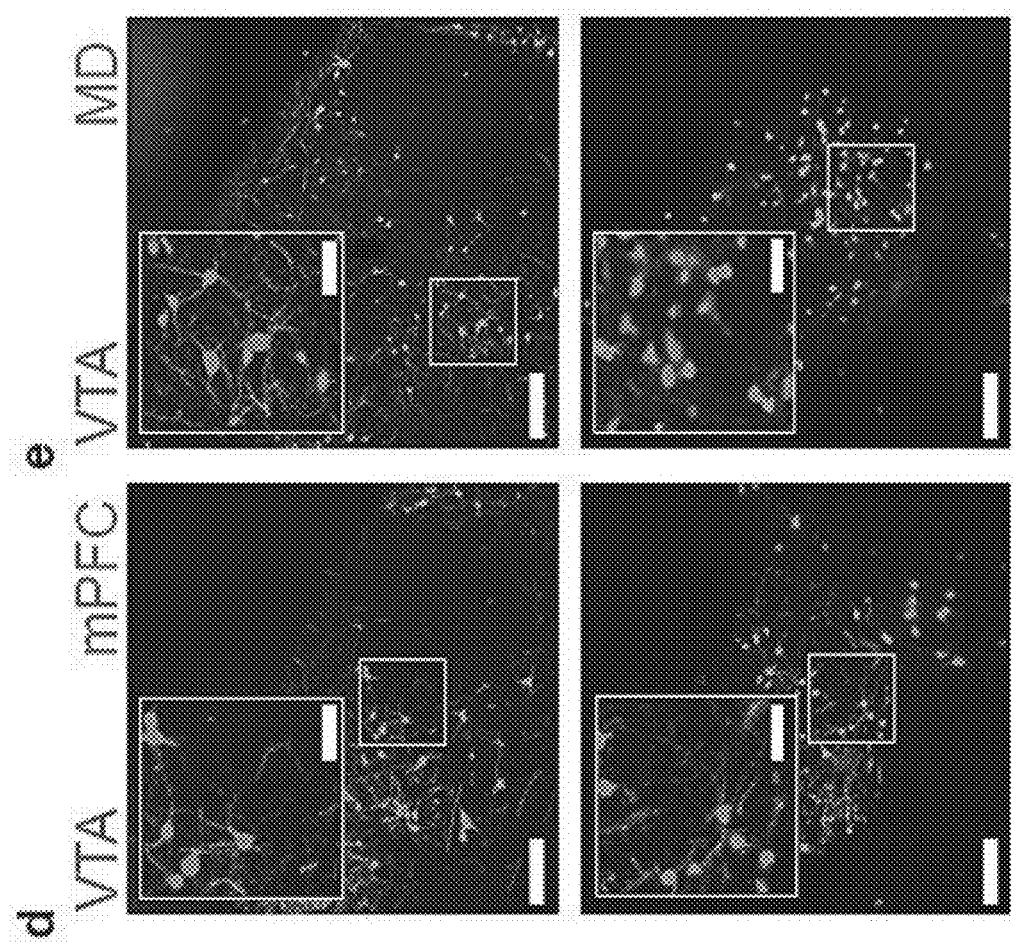
Figure 17E:
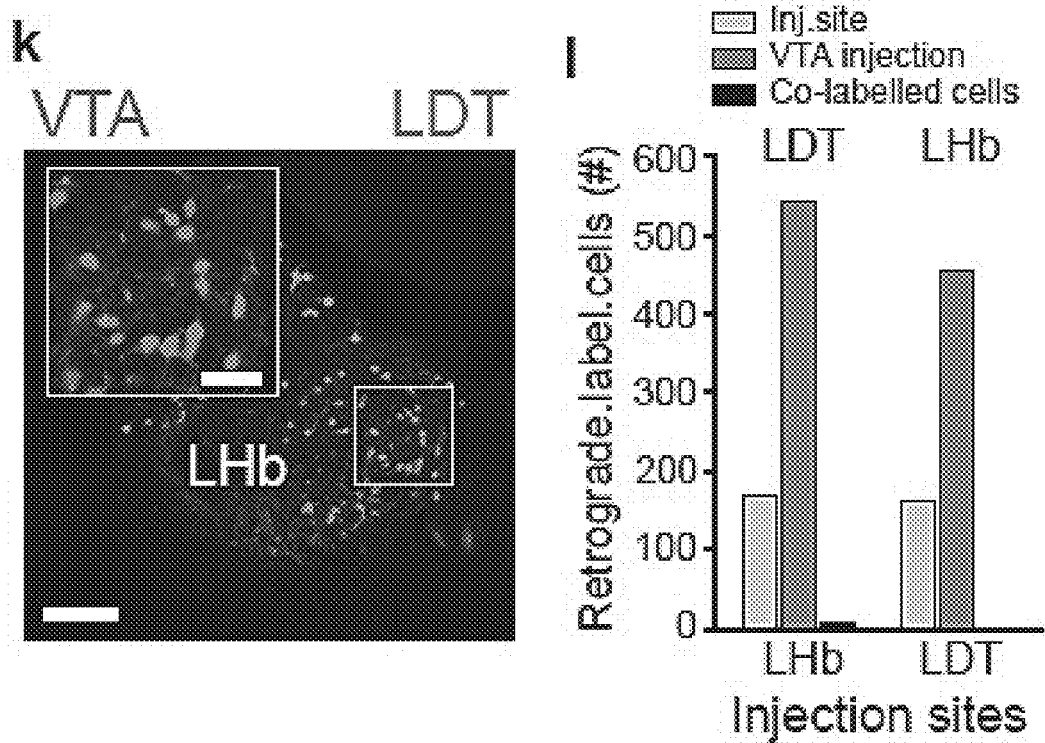

Although the c-fos results confirm that stimulation of LDT and LHb neurons activated neurons in the VTA, axon collaterals of LDT and LHb neurons may project to other brain regions, activation of which mediated the observed CPP and CPA. To address this possibility, we injected adeno-associated viruses expressing ChR2-EYFP (AAV-ChR2) into LDT or LHb and stimulated axons of infected neurons using light application directly in the caudal VTA and RMTg (FIG. 15). This produced robust CPP following intra-VTA LDT axonal stimulation and robust CPA following intra-VTA LHb axonal stimulation (FIG. 15, FIG. 16). A limitation of these experiments is that intra-VTA activation of LDT and LHb axons may cause antidromic activation of axon collaterals projecting to other brain regions. To address this possibility, we injected RV-EGFP or RV-tdTomato into VTA and the other virus into brain regions that receive inputs from LDT or LHb[27, 28]. If single LDT or LHb neurons projecting to VTA send collaterals to these other brain regions, the neurons will express both fluorophores. An extremely small number of LDT and LHb neurons projecting to other structures (i.e. ventral pallidum, lateral septum, lateral hypothalamus, mPFC, mediodorsal thalamic nucleus, and supraoculomotor central grey) expressed both fluorophores (FIG. 17), suggesting that almost all of these neurons project solely to VTA/RMTg. As a positive control we injected one RV into VTA and the other into ventral pallidum and found dorsal raphe neurons (~20%), which are known to project to these two structures[29], expressed both EGFP and tdTomato (FIG. 17). We also injected RVs into VTA and either LDT or LHb and examined labeling of cells in the other structure. Our results confirm that LDT and LHb have reciprocal anatomical connections[28] but the cells providing these projections do not project to VTA (FIG. 17).

Synaptic Connectivity of LDT and LHb Inputs

Figure 3:
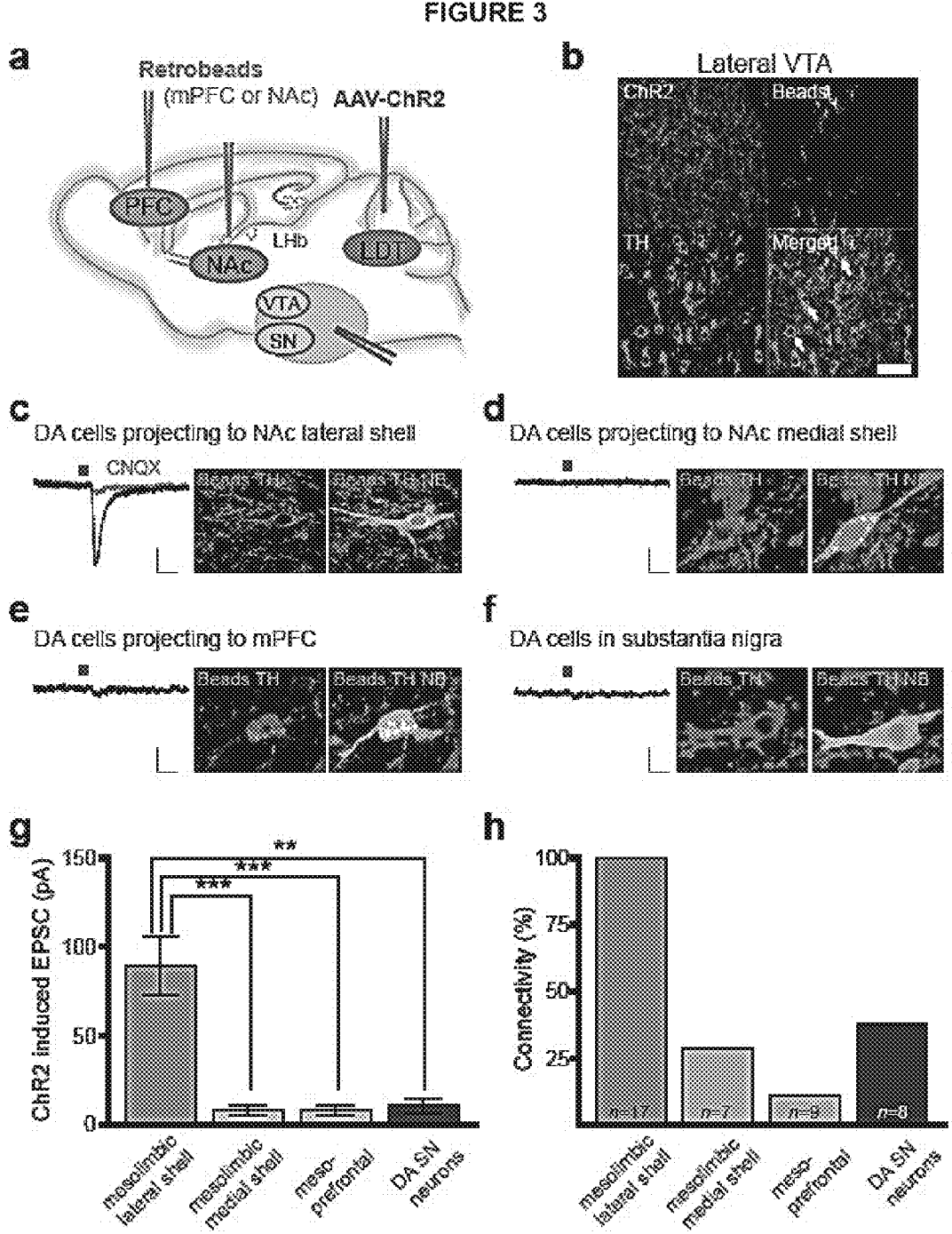
FIG. 3 depicts various measures of connectivity and related quantification of AAV-ChR2 injected LDT and fluorescent retrobead injected target structures of VTA DA neurons.
Figure 18B:
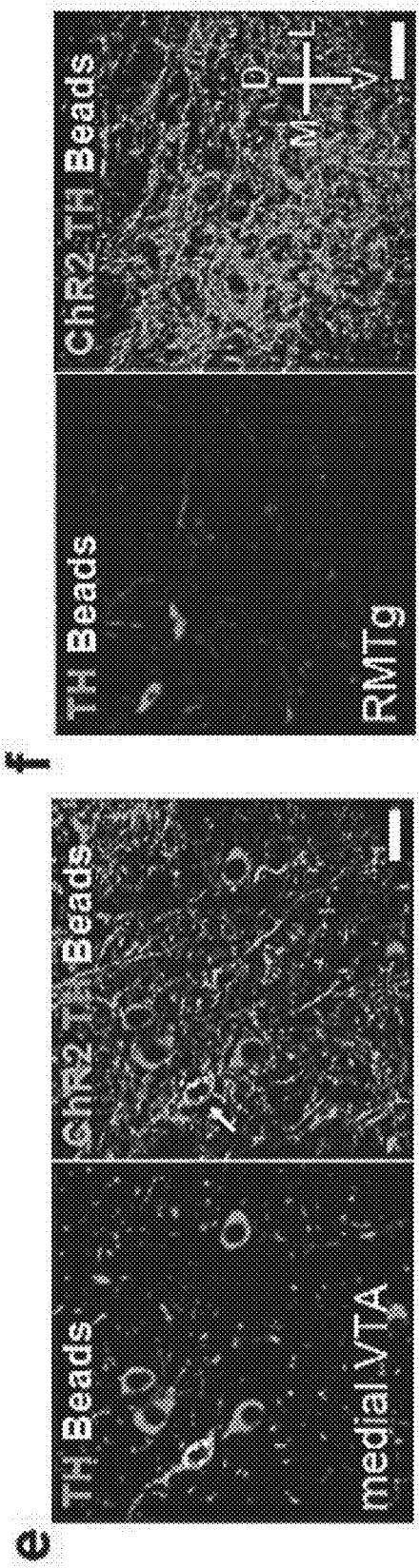
Figure 19A:
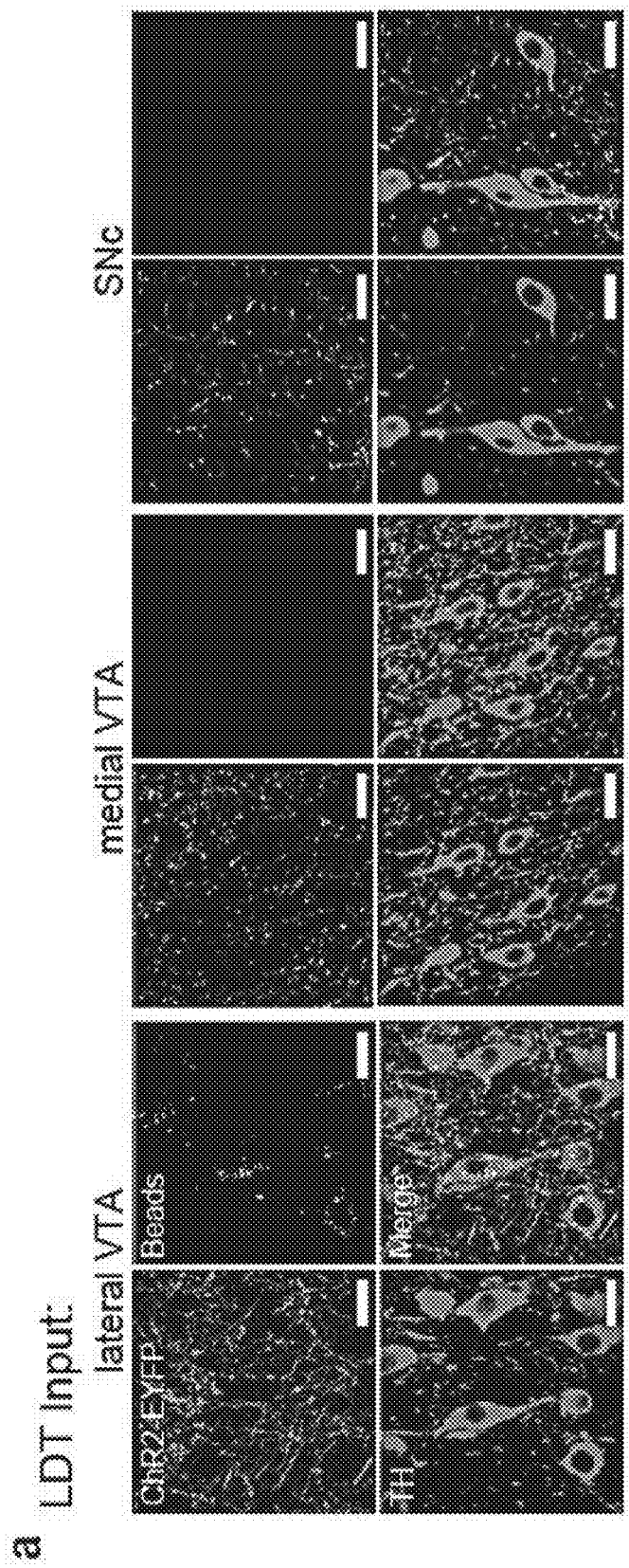
Figure 19B:
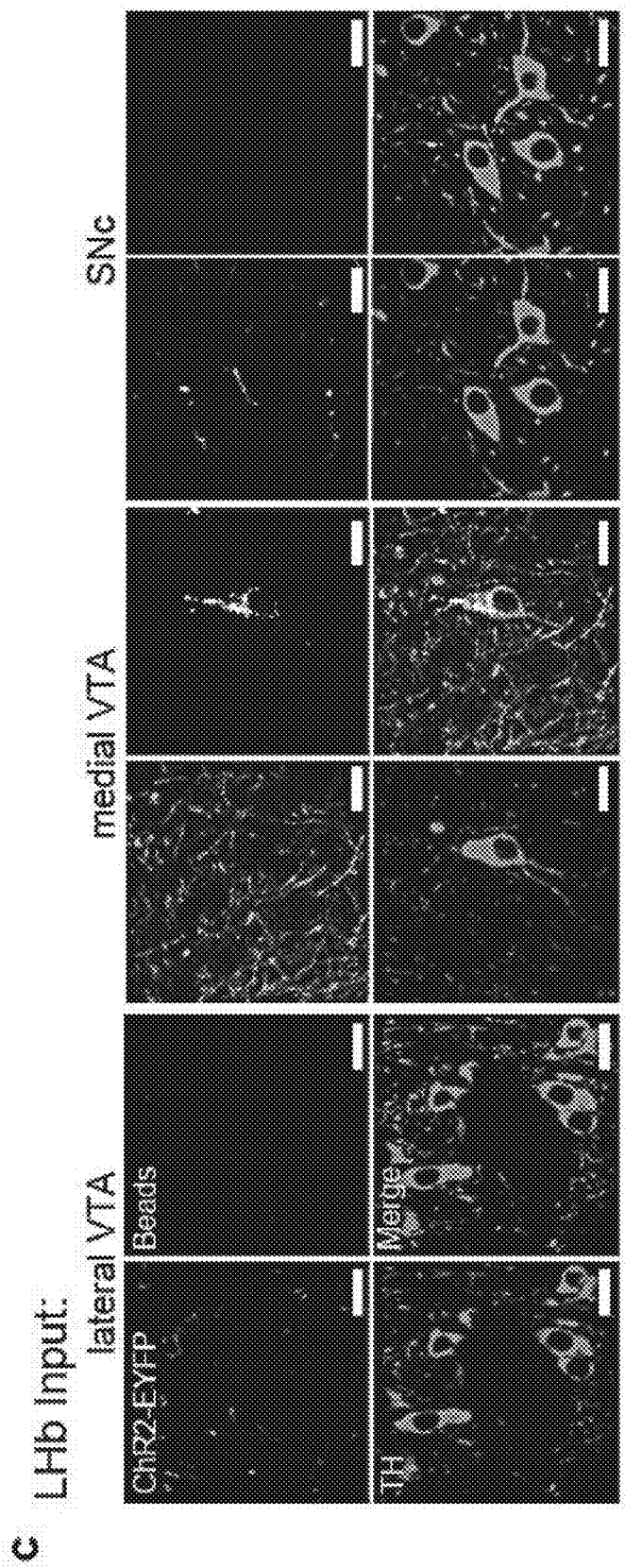

The results thus far suggest that LDT and LHb inputs activate distinct populations of VTA and RMTg neurons and that this leads to reward and aversion, respectively. To address the specific synaptic connectivity of these inputs, we injected AAV-ChR2 into LDT and fluorescent retrobeads into target structures of VTA DA neurons (FIG. 3; FIG. 18). 8-12 weeks following these injections, ChR2-EYFP was expressed adjacent to VTA DA neurons projecting to NAc lateral shell (FIG. 3) and its levels were significantly higher in the lateral VTA (FIG. 19). To determine the DA neuron populations upon which LDT inputs directly synapse, we made whole-cell recordings from retrogradely labeled DA neurons projecting to the NAc lateral and NAc medial shell as well as non-labeled DA SN neurons (FIG. 3). On average, optical stimulation of LDT fibers generated larger excitatory postsynaptic currents (EPSCs) in DA neurons projecting to NAc lateral shell than in DA neurons projecting to medial shell or DA neurons in SN (FIG. 3), all recorded in the same sets of slices. The EPSCs in DA neurons projecting to NAc lateral shell were blocked by an AMPA receptor antagonist (CNQX, 10 µM; FIG. 3) indicating that LDT fibers released glutamate. Importantly, stimulation of EDT inputs generated EPSCs (>10 pA) in 100% of DA neurons projecting to NAc lateral shell but only in ~30-40% of DA neurons projecting to NAc medial shell or in SN (FIG. 3). Furthermore, only ~10% of DA neurons projecting to mPFC yielded EPSCs (FIG. 3).

Figure 4:
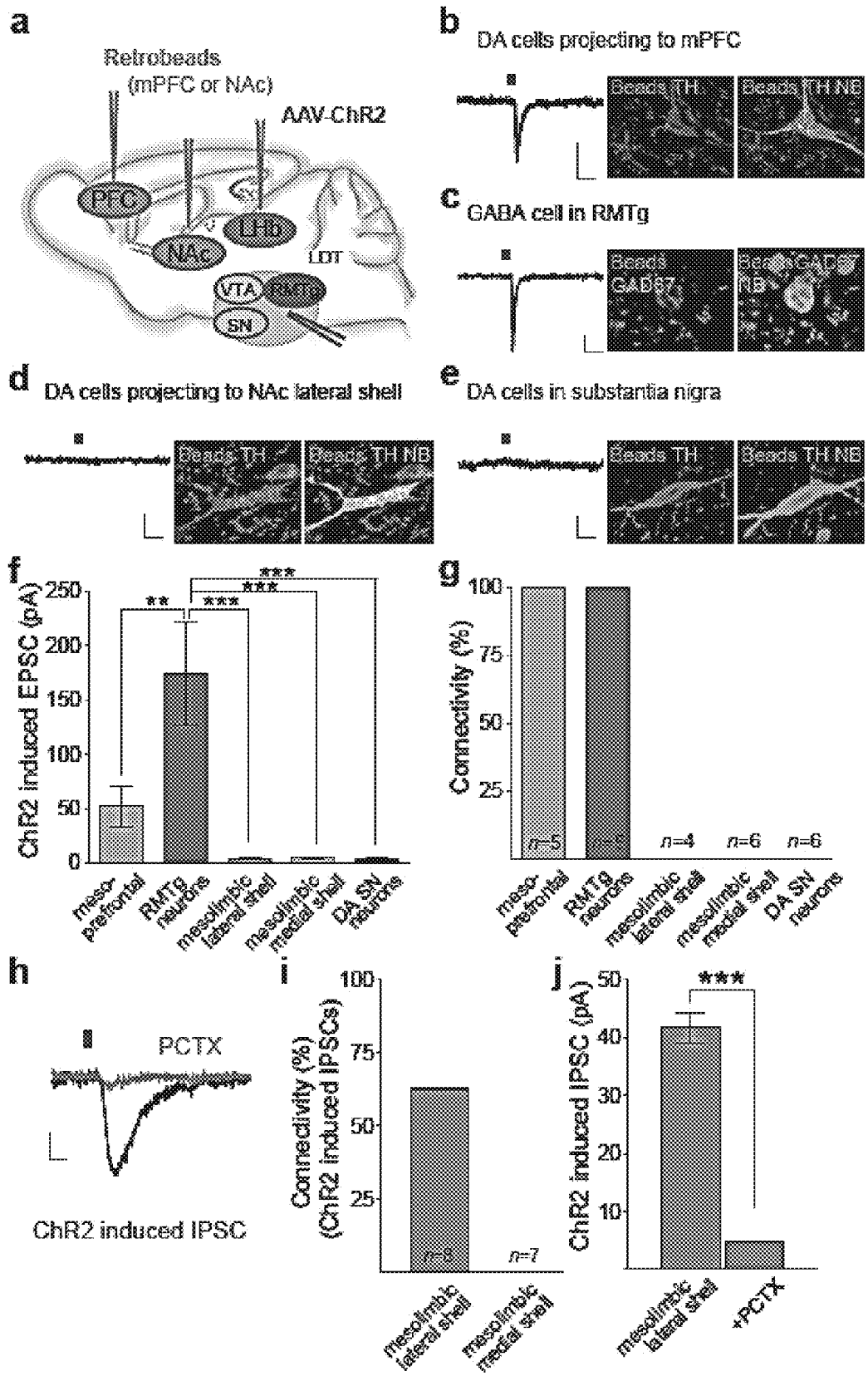
FIG. 4 depicts various measures of connectivity and related quantification of AAV-ChR2 injected LHb and fluorescent retrobead injected NAc lateral and medial shells or mPFC.

The same methodology (FIG. 4; FIG. 18) revealed that LHb inputs synapse on a different subpopulation of VTA DA neurons as well as on GABAergic cells in the RMTg. ChR2-EYFP expressing fibers from the LHb were found in medial posterior VTA in close proximity to DA neurons projecting to mPFC as well as in the RMTg (FIG. 18, FIG. 19). Importantly, light-evoked EPSCs were generated in 100% of DA neurons projecting to mPFC as well as GABAergic RMTg neurons whereas detectable EPSCs were not generated in DA neurons projecting to NAc medial shell or NAc lateral shell nor in SN neurons (FIG. 4). Since LHb inputs preferentially synapse on NAc DA neurons projecting to mPFC and RMTg GABAergic cells, we predicted that LHb inputs may inhibit DA neurons projecting to NAc lateral shell via feed-forward inhibition. Indeed, in ~60% of DA neurons projecting to NAc lateral shell stimulation of LHb inputs evoked IPSCs (FIG. 4). In contrast, stimulation of LHb axons did not generate detectable IPSCs in DA neurons projecting to NAc medial shell (FIG. 4).

Figure 5:
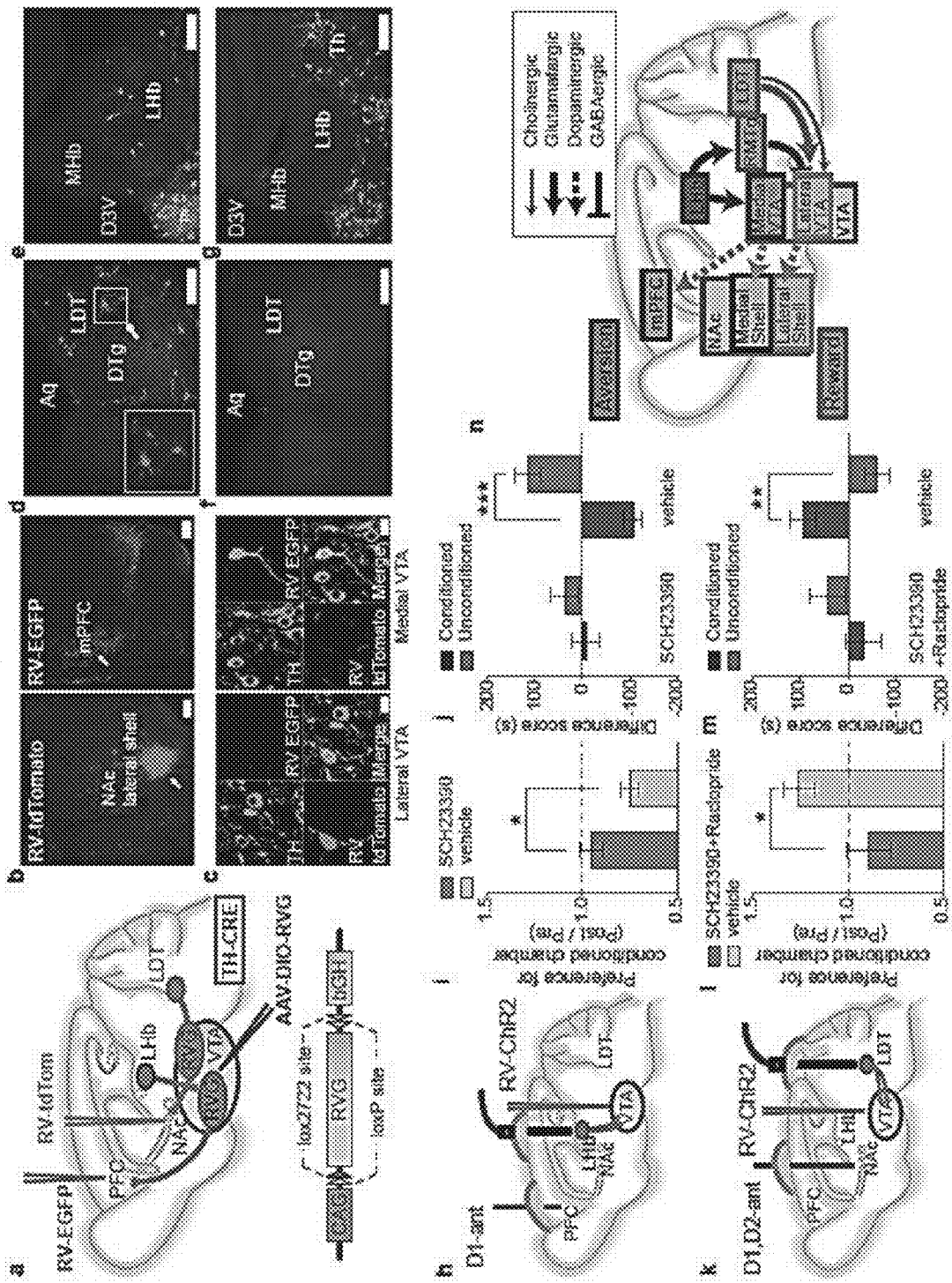
FIG. 5 depicts neuronal connectivity between VTA neurons and mPFC and NAc lateral shell neurons and the effects of DA receptor antagonists on conditioned place preference/avoidance.

These results suggest that LDT and LHb inputs to VTA preferentially activate distinct populations of DA neurons that project to different target structures and that in addition, LHb inputs activate GABAergic cells in RMTg and perhaps within the VTA itself. Such differences in connectivity can explain the different behavioral consequences of LDT and LHb stimulation (FIG. 2). To further test these conclusions, we generated AAVs expressing a double floxed RV glycoprotein (AAV-DIO-RVG) and infected the VTA in TH-Cre mice so that glycoprotein was only expressed in DA neurons (FIG. 5). Two weeks later, RV-EGFP and RV-tdTomato were injected into mPFC and NAc lateral shell, respectively (FIG. 5). Because RV-EGFP and RV-tdTomato lack RV glycoprotein, expression of EGFP and tdTomato is restricted to initially infected cells[16]. However, in VTA DA neurons projecting to these targets (FIG. 5), transcomplementation with RV glycoproteins occurs and allows RV-EGFP and RV-tdTomato to spread retrogradely, thus labeling cells that synaptically contact the DA neurons. After RV injections, cells in LDT were clearly labeled with tdTomato with almost no cells expressing EGFP (tdTomato, n=18.75±7.12 cells per animal, EGFP, n=1.25±0.75, n=4 mice; FIG. 5) while LHb cells were clearly labeled with EGFP with almost no cells expressing tdTomato (EGFP, 8.25±3.44 cells; tdTomato, 0.5±0.22, n=4 mice; FIG. 5). When AAV-DIO-RVG was not injected into VTA prior to RV injections, no tdTomato-positive or EGFP-positive cells in LDT or LHb, respectively, were observed (n=3 mice) (FIG. 5). These results confirm that LDT neurons preferentially synapse on VTA DA neurons projecting to NAc lateral shell and LHb neurons preferentially synapse on VTA DA cells projecting to mPFC.

Effects of DA Receptor Antagonists in mPFC and NAc Lateral Shell

Activation of VTA GABAergic cells alone can elicit CPA[13] and disrupt reward consummatory behavior[15]. These results raise the question of whether activation of DA neurons projecting to mPFC is necessary for the CPA elicited by activation of LHb inputs to VTA and RMTg. To address this question, we infused the D1 dopamine receptor antagonist SCH23390 into mPFC immediately prior to stimulating LHb neurons projecting to VTA and RMTg (FIG. 5). This manipulation, which does not impair cocaine CPP[30], prevented the occurrence of CPA, which was elicited in control animals that received vehicle injections into mPFC (FIG. 5; FIG. 20). Similarly, infusion of D1 and D2 receptor antagonists into NAc lateral shell, but not infusion of vehicle, prevented the CPP elicited by activation of LDT neurons projecting to VTA (FIG. 5, FIG. 20). Control experiments revealed that infusion of DA receptor antagonists alone into either the mPFC or NAc lateral shell did not elicit CPP or CPA compared to animals that received vehicle infusions (n=4 mice in each group; p>0.05 Mann-Whitney U-tests). These results provide further evidence that activation of different subpopulations of VTA DA neurons and the consequent release of DA in different target structures are necessary for mediating the reward and aversion generated by activation of LDT and LHb inputs, respectively.

Ventral tegmental area (VTA) dopamine neurons play important roles in adaptive and pathological brain functions related to reward and motivation. It is unknown, however, if subpopulations of VTA dopamine neurons participate in distinct circuits that encode different motivational signatures and whether inputs to the VTA differentially modulate such circuits. Here we show that because of differences in synaptic connectivity activation of inputs to the VTA from the laterodorsal tegmentum and the lateral habenula elicit reward and aversion in mice, respectively. Laterodorsal tegmentum neurons preferentially synapse on dopamine neurons projecting to nucleus accumbens lateral shell while lateral habenula neurons synapse primarily on dopamine neurons projecting to medial prefrontal cortex as well as on GABAergic neurons in the VTA tail. These results establish that distinct VTA circuits generate reward and aversion and thereby provide a novel framework for understanding the circuit basis of adaptive and pathological motivated behaviors.

FIG. 1. LDT and LHb Preferentially Project to Distinct VTA Subregions.

a, Injection sites for RV-tdTomato in NAc and PHA-L in LDT. Image shows PHA-L staining in LDT (4V: fourth ventricle). b, RV-tdTomato in NAc lateral shell. c, VTA neurons projecting to NAc lateral shell are mainly located in lateral VTA (IPN: interpeduncular nucleus) (a-c scale bars, 200 μm). d,e, PHA-L labeled terminals (green) from LDT are adjacent to cells projecting to NAc lateral shell (red) as well as TH-immunopositive processes (blue). f, g, Few PHA-L labeled terminals were detected in medial VTA (f) and in SN (g) (d-g scale bars, 20 μm). h, Injection sites for RV-tdTomato in mPFC and PHA-L in LHb. Image shows PHA-L staining in LHb (MHb: medial habenula; D3V: dorsal third ventricle). i, RV-tdTomato in mPFC. j, VTA neurons projecting to mPFC are mainly located in medial VTA (h-j scale bars, 200 μm). k, l, PHA-L labeled terminals (green) from LHb are found adjacent to cells projecting to mPFC (red) as well as TH-immunopositive processes (blue). m, n, Few PHA-L labeled terminals were detected in lateral VTA (m) and in SN (n) (k-n scale bars, 20 μm).

FIG. 2. Stimulation of LDT and LHb Inputs to VTA Elicits CPP and CPA.

a,b, RV-ChR2 injection into VTA and optical stimulation of (a) LDT- and (b) LHb projection neurons. c, Procedure to elicit and test CPP and CPA. d,e, Example day 3 mouse tracks, Post-Test 1. Arrow indicates chamber in which (d) LDT or (e) LHb projection neurons were stimulated on Day 2. f, Ratio from Post-Test 1/Pre-Test of time spent in conditioned chamber was higher in LDT-ChR2 mice compared to LDT-EGFP mice (LDT-ChR2: 1.32±0.1, n=8; LDT-EGFP: 0.96±0.13, n=7) but lower in LHb-ChR2 mice (LHb-ChR2: 0.76±0.06, n=9; LHb-EGFP: 0.99±0.08, n=11). g, Differences between Post-Test 1 and Pre-Test in time mice spent in conditioned or unconditioned chambers. (LDT-ChR2 mice: conditioned chamber: 105.4±34.38, n=8; unconditioned chamber: −51.1±26.76, n=8) (LHb-ChR2 mice: cond. chamber: −90.87±22.59, n=9; unconditioned chamber: 124.3±26.27, n=9). h, Stimulation of LDT-ChR2 mice during Post-Test 2 enhanced preference for conditioned chamber (LDT-ChR2Post-Test 1, 1.32±0.1, n=8; Post-Test 2, 1.85±0.2, n=8; Post-Test 2 LDT-EGFP mice 1.13±0.16, n=7). Stimulation of LHb-Chr2 mice during Post-Test 2 did not cause further aversion (LHb-ChR2 Post-Test 1, 0.76±0.06, n=9; Post-Test 2, 0.85±0.08, n=9) which was still present (LHb-EGFP Post-Test 2, 1.22±0.16, n=11). (Post-test 1 results are same as in f). i, Low frequency stimulation of LDT-ChR2 and LHb-ChR2 cells did not elicit CPP or CPA (Post-Test 1, LDT-ChR2, 1.13±0.09, n=6; Post-Test 2, LDT-ChR2, 1.28±0.26, n=6; Post-Test 1, LHb-ChR2, 0.97±0.14, n=7; Post-Test 2, LHb-ChR2, 1.14±0.17, n=6). Error bars denote s.e.m. *p<0.05; p<0.01; *p<0.001, Mann-Whitney U-test.

FIG. 3. LDT Neurons Preferentially Synapse on DA Neurons Projecting to NAc Lateral Shell.

a, AAV-ChR2-EYFP injected into LDT and retrobeads injected into NAc lateral shell and NAc medial shell or in mPFC. b, ChR2-EYFP expression in close proximity to retrogradely labeled (beads) TH-immunopositive neurons in lateral VTA (scale bar, 50 μm). c-f, Traces from whole-cell recordings at −70 mV showing EPSCs generated by stimulation of LTD inputs in retrogradely labeled VTA neurons (beads) projecting to (c) NAc lateral shell, (d) NAc medial shell, (e) mPFC or (f) SN neurons. All cells were filled with neurobiotin (NB, green) and are TH-immunopositive (blue). Scale bars: 20 pA/20 ms. g, Summary of average EPSCs generated by optical stimulation of LDT inputs in the four cell populations (\*\*p<0.01, \*\*\*p<0.001, 1 way ANOVA with Bonferroni post-hoc test; Error bars denote s.e.m.). h, Percentage of cells in which optical stimulation generated EPSCs>10 pA. N's shown within each bar also apply to g.

FIG. 4. LHb Neurons Preferentially Synapse on DA Neurons Projecting to mPFC and RMTg GABAergic Neurons.

a, AAV-ChR2-EYFP injected into LHb and retrobeads injected either into NAc lateral shell and NAc medial shell or in mPFC. b-e, Traces from whole-cell recordings at −70 mV showing EPSCs generated by optical stimulation of LHb inputs in retrogradely labeled VTA neurons (beads, red) projecting to (b) mPFC or (c) NAc lateral shell or (d) an RMTg cell and (e) SN cell. All cells were filled with neurobiotin (NB, green) and are either TH-immunopositive (blue) (b, c, e) or GAD67-immunopositive (blue, d). Scale bars: 20 pA/20 ms. f, Summary of average EPSCs generated by optical stimulation of LHb inputs in five cell populations \*\*p<0.01, \*\*\*p<0.001, 1 way ANOVA with Bonferroni post-hoc test, error bars denote s.e.m.). g, Percentage of cells in which optical stimulation generated EPSCs>10 pA. N's shown in this graph also apply to f. h, Optical stimulation of LHb inputs generates IPSC in DA cell projecting to NAc lateral shell (PCTX, picrotoxin) (scale bars, 20 pA/20 ms). Graph shows percentage of DA cells projecting to NAc lateral shell or medial shell in which IPSCs were generated by LHb input stimulation. i, Average IPSC size from DA cells projecting to NAc lateral shell, IPSCs were blocked by picrotoxin (n=3; \*\*\*p<0.0001, unpaired Student's t-test).

FIG. 5. Rabies Virus Reveals Distinct VTA Circuits and Effects of DA Receptor Antagonists on CPP/CPA.

a, AAV expressing rabies glycoprotein (RVG) in a Cre-dependent manner was injected into VTA of TH-Cre mice. RV-EGFP and RV-tdTomato, injected subsequently into mPFC and NAc, respectively, are retrogradely transported to subpopulations of DA neuron in which transcomplementation occurs, allowing RV to spread retrogradely and label cells that synaptically contact infected DA neurons. b, Injection sites in NAc lateral shell (RV-tdTomato) and mPFC(RV-EGFP) (scale bars, 200 μm). c, TH-immunoreactive neurons in VTA retrogradely labeled by RV-tdTomato or RV-EGFP (scale bars, 20 μm). d,e tdTomato and EGFP labeling in LDT (d) and LHb (e) neurons, respectively, when injection of AAV-DIO-RVG into VTA of TH-Cre mice was performed prior to RV injections (DTg, dorsal tegmental nucleus; Aq, aqueduct; MHb, medial habenula; D3V, dorsal third ventricle; Th, thalamus) (d, e scale bars, 100 μm). f,g, Lack of tdTomato expression in LDT (f) and lack of EGFP expression in LHb (g) following RV injections in TH-Cre mice that were not injected with AAV-DIO-RVG (f, g scale bars, 100 μm). h, Placements of drug infusion cannula into mPFC and optic fiber into LHb as well as injection of RV-ChR2 into VTA. i, Ratio of Post-Test/Pre-Test time spent in conditioned chamber when SCH23390 (SCH) or vehicle was infused into mPFC prior to LHb optical stimulation (SCH: 0.95±0.05, n=9; vehicle: 0.75±0.04, n=7). j, Difference between Post-Test and Pre-Test in time mice spent in conditioned or unconditioned chambers following LHb stimulation (SCH: conditioned chamber, −7.24±28.79, unconditioned chamber: 36.83±30.74, n=9; vehicle: conditioned chamber, −106.88±18.82, unconditioned chamber, 112.61±26.48, n=7). k, Placements of drug infusion cannula into NAc lateral shell and optic fiber into LDT as well as injection of RV-ChR2 into VTA. l, Ratio of Post-Test/Pre-Test time spent in conditioned chamber when SCH23390 and raclopride (rac) or vehicle were infused into NAc lateral shell prior to LDT optical stimulation (SCH/rac: 0.89±0.1, n=7; vehicle: 1.26±0.08, n=6). m, Difference between Post-Test and Pre-Test in time mice spent in conditioned or unconditioned chamber following LDT stimulation (SCH/rac: conditioned chamber: −30.17±37.38, unconditioned chamber: 42.22±34.68, n=7; vehicle: conditioned chamber: 94.58±27.77, unconditioned chamber, −59.38±26.44, n=6) \*p<0.05, \*\*p<0.01, \*\*\*p<0.001, Mann-Whitney U-test. Error bars denote s.e.m. n, Hypothesized circuits driven by LDT and LHb inputs into the VTA. Green shading indicates circuit involved in aversion; red/pink shading indicates circuit involved in reward and salience.

FIG. 7. Identification of Inputs to VTA.

a, Schematic showing rabies virus (RV)-EGFP injected into the VTA. b, Image showing EGFP expression in VTA (IPN: interpeduncular nucleus). c-f, Images of clusters of EGFP-positive VTA projection neurons in (c) prefrontal cortex (PFC), (d) nucleus accumbens (NAc), (e) lateral hypothalamus (LH) and lateral habenula (LHb, inset), (f) laterodorsal tegmentum (LDT) (scale bars, 200 μm). g, Summary schematic of all labeled inputs to the VTA (M1/2, primary and secondary motor cortex; Cg, cingulate cortex; PrL/IL, prelimbic/infralimbic cortex; MO, medial orbital cortex; NAc, nucleus accumbens; CPu, caudate-putamen; VP, ventral pallidum; BNST, bed nucleus of the stria terminalis; LHb, lateral habenula; LH, lateral hypothalamus; PPT, pedunculopontine tegmental nucleus; DR, dorsal raphe; LDT, laterodorsal tegmentum).

FIG. 8.

LDT and LHb neurons that project to the VTA are mainly glutamatergic. a, EGFP-positive neurons (green) in the LDT following injection of RV-EGFP in the VTA (DTg, dorsal tegmental nucleus; 2cb, 2nd cerebellar lobule) (Scale bar, 100 μm). b, Upper row: confocal images showing an EGFP-positive neuron in the LDT that is immunopositive for choline acetyltransferase (ChAT, red, arrow). Note, that many ChAT-positive neurons do not co-localize with EGFP. Lower row: confocal images showing an EGFP-positive neuron in the LDT that is immunopositive for the glutamate transporter (EAAC1, red, left arrow) and another EGFP-positive neuron that is immunonegative for EAAC1 (right arrow) (Scale bars, 20 μm). c, ChAT was coexpressed in 7% of EGFP-positive neurons in the LDT (n=484 cells analyzed from 2 mice). EAAC1 was coexpressed in 95% of EGFP positive neurons in the LDT (n=386 cells analyzed from 2 mice). d, EGFP-positive neurons (green) in the LHb following injection of RV-EGFP in the VTA (DTg, dorsal tegmental nucleus; 2cb, 2nd cerebellar lobule) (Scale bar, 100 μm). Note, that some EGFP-positive neurons are located in the medial habenula (MHb) due to small virus contaminations in the dorsal interpeduncular nucleus (IPN). Control experiments in which retrobeads were injected into the VTA with no contamination in the IPN did not show labeling of MHb neurons indicating that LHb, but not MHb, neurons project to the VTA (data not shown). e, Upper row: confocal images showing that EGFP-positive neurons in the LHb are ChAT (red)immunonegative. Lower row: Confocal images showing EGFP-positive neurons are EAAC1 (red)immunopositive. All analyzed EGFP-positive cells (n=499 cells from 3 mice) were immunopositive for EAAC1 (Scale bars, 20 μm). f, Confocal image showing that ChAT-positive neurons (red) could be found in the medial habenula.

FIG. 9.

LDT and LHb terminals in the VTA are immediately adjacent to DA neurons projecting to different target structures. a, Upper row: schematic (left) and representative image of the injection-site of the anterograde tracer *Phaseolus vulgaris leucoagglutinin* (PHA-L, green) in the LDT (middle) (DTg, dorsal tegmental nucleus; 2cb, 2nd cerebellar lobule). Retrobead injection-site in the NAc lateral shell from the same animal (right image) (Scale bars, 200 µm). Middle row: Confocal images showing that PHA-L immunopositive terminals from the LDT are mainly found in the lateral VTA in close proximity to TH-positive (blue) neurons which are retrogradely labeled (beads, white), indicating that they project to the NAc lateral shell (Scale bars, left/right, 50/20 µm). Lower row: Confocal images showing very sparse PHA-L labeling in the medial VTA and SN (Scale bars, 50 b, Upper row: schematic (left) and representative image of the PHA-L injection site (green) in the LHb (middle) (DG, dentate gyrus; MHb, medial habenula; CL, centrolateral thalamic nucleus; MDL, mediodorsal thalamic nucleus, lateral part). Retrobead injection-site in the mPFC from the same animal (right) (Scale bars, 200 µm). Middle row: confocal images showing that PHA-L immunopositive terminals from the LHb are mainly found in the medial VTA in close proximity to TH-positive (blue) neurons which are retrogradely labeled (beads, white), indicating that they project to the mPFC (Scale bars, left/right, 50/20 µm). Lower row: confocal images showing very sparse PHA-L labeling in the lateral VTA and SN (Scale bars, 50 µm). c, Following injection of PHA-L into the LHb, intense PHA-L labeling could be found in the RMTg. Schematic of the anatomical location of the RMTg (upper left) and representative image showing PHA-L immunopositive terminals in the RMTg (upper right; Scale bar 200 µm) (IP, caudal interpeduncular nucleus). Lower picture: confocal image showing PHA-L-positive LHb terminals in the RMTg are adjacent to GAD67-immunopositive neurons (red; Scale bar, 20 µm).

FIG. 10.

Establishing a behavioral assay for examining the consequences of activating LDT and LHb neurons that project to the VTA. To investigate the in vivo function of LDT and LHb inputs to the VTA we developed a rabies virus (RV) encoding channelrhodopsin 2 (ChR2) and used a well-validated behavioral assay: conditioned place preference/aversion. a, Schematic diagram of the genome of recombinant rabies virus expressing ChR2-EYFP and an image of the expression of ChR2-EYFP by rabies virus in HEK293 cells. The open reading frame of the glycoprotein is replaced with that of ChR2-EYFP. N, P, M and L denote the open reading frames of remaining viral genes that express nucleoprotein, phosphoprotein, matrix protein, and viral polymerase, respectively. b, The conditioned place preference/aversion chamber was designed so that mice did not have a consistent bias for a particular chamber. To test this, we used male, 12 week old C57Bl/6 mice (n=9) and let them freely explore the chamber for 15 min over a period of 5 days. There was no significant change in the Post/Pre ratio over the 5 days (Post/Pre ratio day 2: 1.03±0.08, day 3: 1.05±0.09, day 4: 1.05±0.07, day 5: 1.08±0.09, p>0.05 1 way ANOVA, Bonferroni post-hoc test).

FIG. 11.

Pre- and Post-Test times spent in conditioned chamber for the behavioral assays of individual mice that were injected with RV-ChR2-EYFP or RV-EGFP into the VTA. a-c, For LDT stimulation mice received phasic simulation after expression of ChR2-EYFP (a) or EGFP (b) as well as tonic stimulation after expression of ChR2-EYFP (c). d-e, Similarly, for LHb stimulation mice received phasic simulation after expression of ChR2-EYFP (d) or EGFP (e) as well as tonic stimulation after expression of ChR2-EYFP (f). Note that there are no significant differences in the Pre-Test times between mice injected with RV-ChR2-EYFP and mice injected with RV-EGFP as well as between mice in which the LDT or LHb was optically stimulated (*p<0.05, Mann-Whitney U-Test).

FIG. 12.

Stimulation of LDT and LHb neurons projecting to VTA does not influence locomotor activity nor anxiety. a, Bar graph showing that there was no significant difference in the Post-Test 1/Pre-Test ratio for time spent in the central chamber following stimulation of LDT and LHb inputs to the VTA between RV-ChR2 and RV-EGFP injected mice (LDT-ChR2: 0.71±0.06, n=8; LDT-EGFP: 0.92±0.12, n=7, p>0.05 Mann-Whitney U-Test; LHb-ChR2: 0.79±0.08, n=9; LHb-EGFP: 0.82±0.12, n=11, p>0.05 Mann-Whitney U-Test). b, Bar graph showing that the difference score for the central chamber was not significantly different between LDT-ChR2 and LHb-ChR2 mice (LDT-ChR2: −54.25±13.33, n=8; LHb-ChR2: −33.42±12.33, n=9, p=0.236; p>0.05 Mann-Whitney U-Test). c, Bar graph showing that there was no significant difference in the Post-Test 2/Pre-Test ratio for the central chamber between RV-ChR2 and RV-EGFP injected mice (LDT-ChR2: 0.48±0.1, n=8, LDT-EGFP: 0.76±0.1, n=7, p>0.05 Mann-Whitney U-Test; LHb-ChR2: 0.69±0.07, n=9, LHb-EGFP: 0.64±0.15, n=11, p>0.05 Mann-Whitney U-Test). d, Bar graph showing that a low frequency stimulation protocol did not significantly change the post/pre ratio of the central chamber in RV-ChR2 and RV-EGFP injected mice (Post-Test 1: LDT-ChR2: 1±0.14, n=6, Post-Test 2: LDT-ChR2: 0.85±0.1, n=6, p>0.05 Mann-Whitney U-Test; Post-Test 1: LHb-ChR2: 0.67±0.13, n=7, Post-Test 2: LHb-ChR2: 0.69±0.2, n=7; p>0.05 Mann-Whitney U-Test). e-h, Optical stimulation of LDT and LHb inputs to the VTA did not significantly influence general locomotor activity nor anxiety in an open-field-test. The bar graphs show the mean total time for the light on and light off period (9 min each) for: (e) average velocity (LDT-EGFP, light off, 5.5±0.1, light on, 5.6±0.4; LDT-ChR2, light off, 6.6±0.5, light on, 7±0.5; p>0.05 1 way ANOVA, Bonferroni post-hoc test: LHb-EGFP, light off, 5.7±0.3, light on, 5.7±0.3; LHbChR2, light off, 6.4±0.6, light on, 6.7±0.5; p>0.05 1 way ANOVA, Bonferroni post-hoc test). (f) track length (LDT-EGFP, light off, 997.5±18.4, light on, 1007±76; LDT-ChR2, light off, 1181±89, light on, 1260±97.8; p>0.05 1 way ANOVA, Bonferroni post-hoc test: LHb-EGFP, light off, 1026±58.8, light on, 1020±62.1; LHb-ChR2, light off, 1157±114.9, light on, 1214±97.5; p>0.05 1 way ANOVA, Bonferroni post-hoc test). (g) wall distance (LDT-EGFP, light off, 5.5±0.5, light on, 4.9±0.6; LDT-ChR2, light off, 5.1±0.3, light on, 5.2±0.3; p>0.05 1 way ANOVA, Bonferroni post-hoc test: LHb-EGFP, light off, 4.8±0.5, light on, 4.6±0.4; LHb-ChR2, light off, 5.3±0.4, light on, 5.4±0.5; p>0.05 1 way ANOVA, Bonferroni post-hoc test). (h) duration in inner zone (LDT-EGFP, light off, 40.2±10, light on, 21.3±7; LDT-ChR2, light off, 32.5±7.6, light on, 32.8±7.8; p>0.05 1 way ANOVA, Bonferroni post-hoc test: LHb-EGFP, light off, 30.1±7.2, light on, 19±2.2; LHb-ChR2 light off, 37.6±5.5, light on, 35.6±9.3; p>0.05 1 way ANOVA, Bonferroni post-hoc test). (LDT-EGFP, n=5 mice; LDT-ChR2, n=7 mice; LHb-EGFP, n=5 mice; LHb-ChR2, n=6 mice.)

FIG. 13.

Further evidence that stimulation of LDT and LHb neurons projecting to VTA does not influence locomotor activity or measures of anxiety in the open field. a, b, Diagram of experimental procedure (a) and examples of individual tracks in the open field (b) during optical stimulation of LDT or LHb neurons that project to VTA. c, d, Summary of the effects of LDT and LHb stimulation in the open field on locomotor velocity (c) and duration of time spent in the inner zone, a measure of anxiety (d; marked by red boxes in b). e, f, Confirmation of placement of optical fibers (cannula track) and ChR2 expression in LDT (e) and LHb (f) (e, f, FIG. 14.

In vivo optical activation of LDT and LHb neurons projecting to the VTA induces c-fos expression in distinct VTA subpopulations. a,b, Confocal images showing TH-immunopositive (i.e. DA) neurons (red) in the (a) lateral VTA and (b) medial VTA. c-fos immunoreactivity (blue) and RV-ChR2 expression (green) or EGFP expression (green) are also shown following stimulation of LDT projection neurons for 30 min using the phasic stimulation protocol. Note lack of c-fos immunoreactivity following stimulation of LDT cells expressing EGFP and in images of medial VTA (Scale bars, 20 µm). c, TH-immunostaining showing the areas that have been analyzed in the lateral and medial VTA (Bregma −3.4 mm; Scale bar, 200 µm). d, Bar graph showing a high proportion of c-fos-positive DA neurons in the lateral VTA following phasic optical stimulation of LDT neurons projecting to VTA in mice injected with RV-ChR2 in VTA (1VTA: TH+cfos+, 38.1%; TH-cfos+, 8.5%; TH+cfos−, 53.4%; n=189 cells from 2 mice) with nearly 3-fold less c-fos-positive DA neurons in the medial VTA (mVTA: TH+cfos+, 14.3%; TH-cfos+, 5.8%; TH+c-fos−, 79.9%; n=224 cells from 2 mice). Extremely low c-fos expression was observed in both lateral and medial VTA following phasic optical stimulation of LDT in mice injected with RV-EGFP in VTA (lateral VTA: TH+cfos+, 0.6%; TH-cfos+, 1.2%; TH+cfos−, 98.2%; n=170 cells from 2 mice; medial VTA: TH+cfos+, 1.7%; TH-cfos+, 3.4%; TH+cfos−, 94.9%; n=177 cells from 2 mice). e, f, Same experimental design as in a,b, but for phasic optical stimulation of LHb neurons projecting to the VTA. Confocal images showing medial (e) and lateral (f) VTA (Scale bars, 20 µm). Note lack of c-fos staining in lateral VTA. g, Bar graphs showing that optical activation of LHb neurons projecting to VTA induced the highest proportion of c-fos-positive DA neurons in the medial VTA (TH+cfos+, 11.9%; TH+cfos−, 16.2%; TH+cfos−, 71.9%; n=210 cells from 2 mice) with 9-fold less c-fos-positive DA neurons in the lateral VTA (TH+cfos+, 1.3%; TH-cfos+, 5.2%; TH+cfos−, 93.5%; n=155 cells from 2 mice). There was a high proportion of c-fos-positive non-DA neurons in the RMTg (TH+cfos+, 4.1%; TH-cfos+, 81.6%; TH+cfos, 14.3%; n=49 cells from 2 mice). There was sparse c-fos expression in any VTA subregion following optical stimulation of LHb in mice injected with RV-EGFP in the VTA (lateral VTA: TH+cfos+, 2.1%; TH-cfos+, 2.1%; TH+cfos−, 95.8%; n=94 cells from 2 mice; medial VTA: TH+cfos+, 3%; TH-cfos+, 7%; TH+cfos−, 90%; n=100 cells from 2 mice; RMTg: TH+cfos+, 0%; TH-cfos+, 14.3%; TH+cfos−, 85.7%; n=7 cells from 2 mice). h, Confocal images showing that retrogradely labeled (beads, red) neurons projecting to the mPFC (left) or NAc medial shell (right), both located in the medial VTA, show differences in c-fos induction following in vivo phasic stimulation of LHb neurons projecting to the VTA (Scale bars, 20 µm). 77% of the mesoprefrontal neurons (n=10/13 cells from 2 mice) were c-fos-positive. In contrast, only 8% of the neurons projecting to the NAc medial shell were c-fos-positive (n=2/25 cells from 2 mice). Note that even though we do not demonstrate that the retrogradely labeled neurons in this experiment are TH-immunopositive, we previously found that the majority of retrogradely labeled neurons in the posterior VTA were DAergic (Lammel et al., 2011).

FIG. 15. Optical Stimulation of Axon Terminals from LDT and LHb in VTA.

a,b, AAV-ChR2 injection into LDT (a) and LHb (b) and optical stimulation of axon terminals in VTA. c, Ratios from Post-Test 1,2/Pre-Test of time spent in conditioned chamber in mice in which LDT axons in VTA were stimulated (LDT Post-Test 1, 1.34±0.2, n=9; Post-Test 2, 1.53±0.1, n=9) or LHb axons in VTA were stimulated (LHb Post-Test 1, 0.79±0.05, n=9; Post-Test 2, 0.65±0.2, n=9). d, Differences between Post-Test 1 and Pre-Test in time mice spent in the conditioned or unconditioned chamber (LDT axon stimulation: conditioned chamber: 100.9±49.07, n=9, unconditioned chamber: −50.05±46.22, n=9) (LHb axon stimulation: conditioned chamber: −105.12±16.92, n=9, unconditioned chamber: 130.4±26.96, n=9). Error bars denote s.e.m. *p<0.05; p<0.01; *p<0.001, Mann-Whitney U-test.

FIG. 16.

Pre- and Post-Test times spent in conditioned chamber for the behavioral assays of individual mice in which AAV-ChR2 was injected into the LDT or Lhb and LDT or LHb axon terminals in the VTA were stimulated a, b, Both LDT (a) and LHb (b) axon terminals received light stimulation. Note that there are no significant differences in the Pre-Test times for the two populations of animals. (*p<0.05, Mann-Whitney U-Test).

FIG. 17.

Double injections of RVs expressing two different fluorophores show LDT and LHb neurons projecting to VTA have very few if any axon collaterals. a-e, Representative images of LDT (top) and LHb (bottom) neurons that were retrogradely labeled by the simultaneous injection of RV-EGFP into VTA and RV-tdTomato into various brain areas including ventral pallidum (VP; a), lateral septum (LS; b), lateral hypothalamus (LHT; c), medial prefrontal cortex (mPFC; d) or mediodorsal nucleus of thalamus (MD, e). Scale bars 150 µm, 50 µm (insets). f-g, Summary bar graphs of the numbers of LDT (f) and LHb (g) neurons that were; (i) retrogradely labeled by the RV injection into the named brain areas, (ii) retrogradely labeled by the RV injection into the VTA, and (iii) retrogradely labeled by both RV's. Almost no cells in either the LDT or the LHb were double labeled. (Su3: supraoculomotor central grey; n=2 mice for each brain area). The bars that reach 400 for the number of LDT or LHb cells retrogradely labeled by the RV injected into the VTA indicate that greater than 400 cells were labeled. h, Confocal image of dorsal raphe-containing brain section from mouse in which RV-EGFP and RV-tdTomato were injected into VTA and VP, respectively. Scale bars, 150 µm, 50 µm (inset). i, Summary bar graphs of the number of DR neurons that were; (i) retrogradely labeled with tdTomato 7 days following RV-tdTomato injection into the VP, (ii) retrogradely labeled with EGFP following RV-EGFP injection into the VTA, and (iii) retrogradely labeled by both RV's (n=2 mice). j, k, Confocal images of retrogradely labeled neurons in LDT (j) and LHb (k) following double injection of RV-EGFP into VTA and RV-tdTomato into LHb (j) or LDT (k), respectively. Scale bar 150 µm, 50 µm (inset). l, Summary bar graphs of the numbers of LDT and LHb neurons that were; (i) retrogradely labeled by the RV injected into the opposite brain area, (ii) retrogradely labeled by the RV injected into the VTA, and (iii) retrogradely labeled by both RVs (n=2 mice). Almost no cells expressed both fluorophores.

FIG. 18. Injection of Retrobeads and AAV-ChR2 for Studies of Synaptic Connectivity.

a, Images showing injection-site of AAV-ChR2-EYFP in the LDT (scale bar, 200 µm). Inset shows higher magnification view (DTg, dorsal tegmental nucleus). b, Image showing injection sites of retrobeads in NAc medial shell (mshell) and NAc lateral shell (lshell) (scale bar, 200 µm) (DS, dorsal striatum). c, Image showing injection site of AAV-ChR2-EYFP in the LHb (scale bar, 200 µm). Inset shows higher magnification view. d, Image showing injection site of retrobeads in mPFC. (Cg, cingulate cortex; PrL, prelimbic cortex; IL, infralimbic cortex). e, Images showing strong ChR2-EYFP (green) expression from LHb axons in close proximity to retrogradely labeled (beads, white) TH-immunopositive (red) neurons in the medial VTA (scale bar, 20 µm). f, Images showing strong ChR2-EYFP (green) expression from LHb axons in RMTg with minimal TH-immunoreactivity and no retrogradely labeled neurons (scale bar, 50 µm).

FIG. 19. Fluorescence Intensity of LDT and LHb Terminals Expressing ChR2-EYFP Differs in VTA Subregions.

a, Confocal images of ChR2-EYFP immunopositive (green) terminals from the LDT in subregions of ventral midbrain also stained for TH (red). Neurons in the lateral VTA were retrogradely labeled by injection of retrobeads (white) in the NAc lateral shell. (Scale bars, 20 µm). b, Bar graph showing that the average fluorescence intensity, a marker for the density of LDT terminals, is significant higher in the medial VTA, compared to the lateral VTA and SN (lateral VTA, 19.1±0.9; medial VTA, 13.5±0.7; SNc, 12±0.9; n=12 confocal images per brain region from 2 mice). c, Same experimental design and color code as in (a) but confocal images show ChR2-EYFP expressing terminals from the lateral habenula. (Scale bars, 20 µm). d, The average fluorescence intensity of LHb terminals in the lateral VTA is significantly lower than in the medial VTA and RMTg (confocal image of ChR2-EYFP expression in the RMTg is shown in FIG. 4), but not significantly different from that in the SNc (lateral VTA, 6.4±0.5; medial VTA, 20.7±1.3; SNc, 5±0.2; RMTg, 33.8±2.5; n=12 confocal images per brain region from 2 mice). (***p<0.001 1 way ANOVA with Bonferroni post-hoc test.)

FIG. 20.

Pre- and Post-Test times spent in the conditioned chamber for the behavioral assays of individual mice in which dopamine receptor antagonists were injected into the mPFC or NAc lateral shell immediately prior to optical stimulation of LHb or LDT neurons that project to VTA. a,b, Infusion of SCH23390 into the mPFC (a) but not vehicle (b) prevented the CPA elicited by phasic stimulation of LHb neurons that project to VTA. c, d, Infusion of SCH23390 and raclopride (c) but not vehicle (d) prevented the CPP elicited by phasic stimulation of LDT neurons that project to VTA. Note that there are no significant differences in the Pre-Test times for the two populations of animals. (*p<0.05, Mann-Whitney U-Test).

FIG. 21.

Expression of ChR2-EYFP in the midbrain, the LDT and the LHb following RV-ChR2 injections into the VTA. a-d, Left panels show images of RVChR2-EYFP (green) expression following TH-immunohistochemistry (red) across the caudorostral extent of the midbrain [bregma: −4.48 mm (a), −4.16 mm (b) −3.52 mm (c), and −3.08 mm (d)]. Right panels show schematic drawings of the corresponding brain regions and use different colors to outline the brains regions in which ChR2-EYFP was detected with each color representing the expression profile from a single mouse (n=5). Scale bars, 200 µm. e, f, Example confocal images of LDT and LHb neurons expressing ChR2-EYFP 7 days following RV-ChR2 injection into the VTA injections. NeuN immunoreactivity identifies all cells in the image. Scale bar, 15 µm. g, Summary graph (n=3 mice) showing the proportion of LDT and LHb cells (identified by NeuN) that expressed ChR2-EYFP. More than 20% of NeuN-positive LDT neurons (22.8%, n=218 of 956) and LHb (20.9%, n=209 of 997) neurons expressed ChR2-EYFP.

FIG. 22.

LHb and LDT neurons projecting to VTA send very few axon collaterals to the interpeduncular nucleus (IPN). a, Schematic showing red and green retrobead injections into VTA or IPN, respectively. b, Confocal image of medial habenula (MHb) and LHb neurons that project to VTA (red beads) and IPN (green beads). Scale bar, 50 µm. c, Summary of all labeled cells (n=2 mice) showing the percentage of LHb and MHb cells that projected to VTA (red beads), IPN (green beads) or both areas (double-labeled). Note that neurons projecting to IPN are predominantly located in the MHb while neurons projecting to VTA are almost exclusively in the LHb. d, e, Confocal image (d; Scale bar, 50 µm; Aq, aqueduct) and summary bar graphs (e) of LDT neurons from the same animals showing that 100% of labeled cells contained red beads and therefore LDT neurons send projections to the VTA but not the IPN.

REFERENCES

1. Bjorklund, A. & Dunnett, S. B. Dopamine neuron systems in the brain: an update. Tr. Neurosci. 30, 194-202 (2007).
2. Bromberg-Martin, E. S., Matsumoto, M. & Hikosaka, O. Dopamine in motivational control: rewarding, aversive, and alerting. Neuron 68, 815-834 (2010).
3. Schultz, W. Multiple dopamine functions at different time courses. Annu. Rev. Neurosci. 30, 259-288 (2007).
4. Lammel, S., et al. Unique properties of mesoprefrontal neurons within a dual mesocorticolimbic dopamine system. Neuron 57, 760-773 (2008).
5. Lammel, S., Ion, D. I., Roeper, J. & Malenka, R. C. Projection-specific modulation of dopamine neuron synapses by aversive and rewarding stimuli. Neuron 70, 855-862 (2011).
6. Margolis, E. B., Mitchell, J. M., Ishikawa, J., Hjelmstad, G. O. & Fields, H. L. Midbrain dopamine neurons: projection target determines action potential duration and dopamine D(2) receptor inhibition. J. Neurosci. 28, 8908-8913 (2008).
7. Sesack, S. R. & Grace, A. A. Cortico-Basal Ganglia reward network: microcircuitry. Neuropsychopharmacol. 35, 27-47 (2010).
8. Geisler, S., Derst, C., Veh, R. W. & Zahm, D. S. Glutamatergic afferents of the ventral tegmental area in the rat. J. Neurosci. 27, 5730-5743 (2007).
9. Berridge, K. C., Robinson, T. E. & Aldridge, J. W. Dissecting components of reward: 'liking', 'wanting', and learning. Curr. Opin. Pharmacol. 9, 65-73 (2009).
10. Cohen, J. Y., Haesler, S., Vong, L., Lowell, B. B. & Uchida, N. Neuron-type-specific signals for reward and punishment in the ventral tegmental area. Nature 482, 85-88 (2012).
11. Guarraci, F. A. & Kapp, B. S. An electrophysiological characterization of ventral tegmental area dopaminergic neurons during differential pavlovian fear conditioning in the awake rabbit. *Behav. Brain Res.* 99, 169-179 (1999).
12. Kim, Y., Wood, J. & Moghaddam, B. Coordinated activity of ventral tegmental neurons adapts to appetitive and aversive learning. *PLoS One* 7, e29766 (2012).
13. Tan, K. R., et al. GABA neurons of the VTA drive conditioned place aversion. *Neuron* 73, 1173-1183 (2012).
14. Matsumoto, M. & Hikosaka, O. Two types of dopamine neuron distinctly convey positive and negative motivational signals. *Nature* 459, 837-841 (2009).
15. van Zessen, R., Phillips, J. L., Budygin, E. A. & Stuber, G. D. Activation of VTA GABA neurons disrupts reward consumption. *Neuron* 73, 1184-1194 (2012).
16. Wickersham, I. R., Finke, S., Conzelmann, K. K. & Callaway, E. M. Retrograde neuronal tracing with a deletion-mutant rabies virus. *Nat. Methods.* 4, 47-49 (2007).
17. Watabe-Uchida, M., Zhu, L., Ogawa, S. K., Vamanrao, A. & Uchida, N. Whole-brain mapping of direct inputs to midbrain dopamine neurons. *Neuron* 74, 858-873 (2012).
18. Hikosaka, O. The habenula: from stress evasion to value-based decision-making. *Nat. Rev. Neurosci.* 11, 503-513 (2010).
19. Forster, G. L. & Blaha, C. D. Laterodorsal tegmental stimulation elicits dopamine efflux in the rat nucleus accumbens by activation of acetylcholine and glutamate receptors in the ventral tegmental area. *Eur. J. Neurosci.* 12, 3596-3604 (2000).
20. Lodge, D. J. & Grace, A. A. The laterodorsal tegmentum is essential for burst firing of ventral tegmental area dopamine neurons. *Proc. Natl. Acad. Sci. USA* 103, 5167-5172 (2006).
21. Jhou, T. C., Geisler, S., Marinelli, M., Degarmo, B. A. & Zahm, D. S. The mesopontine rostromedial tegmental nucleus: A structure targeted by the lateral habenula that projects to the ventral tegmental area of Tsai and substantia nigra compacta. *J. Comp. Neurol.* 513, 566-596 (2009).
22. Kaufling, J., Veinante, P., Pawlowski, S. A., Freund-Mercier, M. J. & Barrot, M. Afferents to the GABAergic tail of the ventral tegmental area in the rat. *J. Comp. Neurol.* 513, 597-621 (2009).
23. Christoph, G. R., Leonzio, R. J. & Wilcox, K. S. Stimulation of the lateral habenula inhibits dopamine-containing neurons in the substantia nigra and ventral tegmental area of the rat. *J. Neurosci.* 6, 613-619 (1986).
24. Jhou, T. C., Fields, H. L., Baxter, M. G., Saper, C. B. & Holland, P. C. The rostromedial tegmental nucleus (RMTg), a GABAergic afferent to midbrain dopamine neurons, encodes aversive stimuli and inhibits motor responses. *Neuron* 61, 786-800 (2009).
25. Ji, H. & Shepard, P. D. Lateral habenula stimulation inhibits rat midbrain dopamine neurons through a GABA (A) receptor-mediated mechanism. *J. Neurosci.* 27, 6923-6930 (2007).
26. Omelchenko, N., Bell, R. & Sesack, S. R. Lateral habenula projections to dopamine and GABA neurons in the rat ventral tegmental area. *Eur. J. Neurosci.* 30, 1239-1250 (2009).
27. Araki, M., McGeer, P. L. & Kimura, H. The efferent projections of the rat lateral habenular nucleus revealed by the PHA-L anterograde tracing method. *Brain Res.* 441, 319-330 (1988).
28. Cornwall, J., Cooper, J. D. & Phillipson, O. T. Afferent and efferent connections of the laterodorsal tegmental nucleus in the rat. *Brain Res. Bull.* 25, 271-284 (1990).
29. Vertes, R. P., Fortin, W. J. & Crane, A. M. Projections of the median raphe nucleus in the rat. *J. Comp. Neurol.* 407, 555-582 (1999).
30. Sanchez, C. J., Bailie, T. M., Wu, W. R., Li, N. & Sorg, B. A. Manipulation of dopamine dl-like receptor activation in the rat medial prefrontal cortex alters stress- and cocaine-induced reinstatement of conditioned place preference behavior. *Neuroscience* 119, 497-505 (2003).
31. Tsai, H. C., et al. Phasic firing in dopaminergic neurons is sufficient for behavioral conditioning. *Science* 324, 1080-1084 (2009).
32. Witten, I. B., et al. Recombinase-driver rat lines: tools, techniques, and optogenetic application to dopamine-mediated reinforcement. *Neuron* 72, 721-733 (2011).
33. Robbins, T. W. & Arnsten, A. F. The neuropsychopharmacology of fronto-executive function: monoaminergic modulation. *Annu. Rev. Neurosci.* 32, 267-287 (2009).
34. Lecourtier, L., Defrancesco, A. & Moghaddam, B. Differential tonic influence of lateral habenula on prefrontal cortex and nucleus accumbens dopamine release. *Eur. J. Neurosci.* 27, 1755-1762 (2008).
35. Li, B., et al. Synaptic potentiation onto habenula neurons in the learned helplessness model of depression. *Nature* 470, 535-539 (2011).
36. Lecourtier, L. & Kelly, P. H. Bilateral lesions of the habenula induce attentional disturbances in rats. *Neuropsychopharmacol.* 30, 484-496 (2005).
37. Shepard, P. D., Holcomb, H. H. & Gold, J. M. Schizophrenia in translation: the presence of absence: habenular regulation of dopamine neurons and the encoding of negative outcomes. *Schizophr Bull* 32, 417-421 (2006).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of modulating a reward- or aversive-related behavior in a mammal, the method comprising:
   a) expressing in one or both of a laterodorsal tegmentum (LDT) neuron and a lateral habenula (LHb) neuron projecting to the ventral tegmental area (VTA):
   i) a depolarizing light-responsive opsin polypeptide that comprises an amino acid sequence having at least about 90% amino acid sequence identity to an amino acid sequence selected from SEQ ID NOs:5-11; or
   ii) a hyperpolarizing light-responsive opsin that comprises an amino acid sequence having at least about 90% amino acid sequence identity to an amino acid sequence selected from SEQ ID NOs:1, 4, 12, 14, and 15; and
   b) exposing the LDT neuron and/or the LHb neuron to light,
   wherein said exposing activates the light-responsive opsin polypeptide, thereby hyperpolarizing or depolarizing the neuron, and wherein said hyperpolarizing or depolarizing modulates a reward- or aversive-related behavior in the mammal.

2. The method of claim 1, wherein said hyperpolarizing light-responsive opsin polypeptide comprises an amino acid sequence having at least about 95% amino acid sequence identity to an amino acid sequence selected from SEQ ID NOs: 1, 4, 12, 14, and 15, and wherein said depolarizing comprises an amino acid sequence having at least about 90% amino acid sequence identity to an amino acid sequence selected from SEQ ID NOs:5-11.

3. The method of claim 1, wherein said light-responsive opsin polypeptide comprises an amino acid sequence having at least about 90% amino acid sequence identity to an amino acid sequence selected from SEQ ID NOs:5-11, wherein the method comprises exposing the LDT to light of a wavelength that activates the light-responsive polypeptide, thereby increasing the reward-related behavior.

4. The method of claim 3, wherein said light-responsive opsin polypeptide comprises an amino acid sequence having at least about 95% amino acid sequence identity to an amino acid sequence selected from SEQ ID NOs:5-11.

5. The method of claim 3, wherein said expressing comprises directly delivering into the LDT neuron a nucleic acid comprising a nucleotide sequence encoding the light-responsive opsin polypeptide.

6. The method of claim 5, wherein the nucleic acid is a recombinant viral expression vector.

7. The method of claim 6, wherein the recombinant viral expression vector is a lentiviral vector or an adeno-associated viral vector.

8. The method of claim 5, wherein the nucleotide sequence is operably linked to a promoter.

9. The method of claim 8, wherein the promoter is an EF1α promoter, a cytomegalovirus promoter, a CAG promoter, a synapsin-I promoter, a synuclein 1 promoter, a CAMKIIα promoter.

10. The method of claim 1, wherein the light is provided by an implantable light source.

11. The method of claim 10, wherein the light source comprises a light-emitting diode.

12. The method of claim 3, wherein the light-responsive opsin polypeptide comprises a membrane trafficking signal comprising the amino acid sequence KSRITSEGEYIPLDQIDINV (SEQ ID NO:16).

13. The method of claim 3, wherein the light-responsive opsin polypeptide comprises an endoplasmic reticulum export signal comprising the amino acid sequence FCYENEV (SEQ ID NO: 17).

14. The method of claim 1, wherein the reward-related behavior is addiction.

* * * * *

UNITED STATES PATENT AND TRADEMARK OFFICE
CERTIFICATE OF CORRECTION

PATENT NO. : 9,636,380 B2
APPLICATION NO. : 14/209004
DATED : May 2, 2017
INVENTOR(S) : Lammel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 27

<210> SEQ ID NO 1
<211> LENGTH: 273
<212> TYPE: PRT
<213> ORGANISM: Natronomonas pharaonis

<400> SEQUENCE: 1

Val Thr Gln Arg Glu Leu Phe Glu Phe Val Leu Asn Asp Pro Leu Leu
```

```
1               5                   10                  15
Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
            35                  40                  45

Ile Ala Val Ser Thr Ile Leu Val Pro Val Val Ser Ile Ala Ser Tyr
50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
            115                 120                 125

Thr Lys Leu Phe Thr Ala Ile Thr Phe Asp Ile Ala Met Cys Val Thr
        130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
        195                 200                 205

Ile Val Trp Ala Leu Gly Val Glu Gly Ile Ala Val Leu Pro Val Gly
    210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
            260                 265                 270

Asp

<210> SEQ ID NO 2
<211> LENGTH: 559
<212> TYPE: PRT
<213> ORGANISM: Artificial Sequence
<220> FEATURE:
<223> OTHER INFORMATION: synthetic amino acid sequence

<400> SEQUENCE: 2

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95
```

```
Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
            115                 120                 125

Leu Ser Thr Pro Met Ile Leu Leu Ala Leu Gly Leu Leu Ala Gly Ser
        130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
            195                 200                 205

Asp Met Phe Asn Thr Leu Lys Leu Leu Thr Val Val Met Trp Leu Gly
        210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
            275                 280                 285

Ala Asp Asp Ala Ala Ala Lys Ser Arg Ile Thr Ser Glu Gly Glu Tyr
        290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
        355                 360                 365

Val Pro Trp Pro Thr Leu Val Thr Thr Phe Gly Tyr Gly Leu Gln Cys
370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
                405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
        435                 440                 445

Asn Ile Leu Gly His Lys Leu Glu Tyr Asn Tyr Asn Ser His Asn Val
450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
                485                 490                 495

Gln Gln Asn Thr Pro Ile Gly Asp Gly Pro Val Leu Leu Pro Asp Asn
            500                 505                 510
```

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
530                 535                 540

Leu Gly Met Asp Glu Leu Tyr Lys Phe Cys Tyr Glu Asn Glu Val
545                 550                 555

<210> SEQ ID NO 3
<211> LENGTH: 542
<212> TYPE: PRT
<213> ORGANISM: Artificial sequence
<220> FEATURE:
<223> OTHER INFORMATION: synthetic amino acid sequence

<400> SEQUENCE: 3

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
        35                  40                  45

Leu Ile Ala Val Ser Thr Ile Leu Val Pro Val Val Ser Ile Ala Ser
50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
                85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
        115                 120                 125

Ala Thr Lys Leu Phe Thr Ala Ile Thr Phe Asp Ile Ala Met Cys Val
130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
        195                 200                 205

Pro Ile Val Trp Ala Leu Gly Val Glu Gly Ile Ala Val Leu Pro Val
210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
        275                 280                 285

Pro Leu Asp Gln Ile Asp Ile Asn Val Val Ser Lys Gly Glu Glu Leu
290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Asp Ala Thr Tyr
            325                 330                 335

Gly Lys Leu Thr Leu Lys Phe Ile Cys Thr Thr Gly Lys Leu Pro Val
            340                 345                 350

Pro Trp Pro Thr Leu Val Thr Thr Phe Gly Tyr Gly Leu Gln Cys Phe
            355                 360                 365

Ala Arg Tyr Pro Asp His Met Lys Gln His Asp Phe Phe Lys Ser Ala
370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
            405                 410                 415

Val Asn Arg Ile Glu Leu Lys Gly Ile Asp Phe Lys Glu Asp Gly Asn
            420                 425                 430

Ile Leu Gly His Lys Leu Glu Tyr Asn Tyr Asn Ser His Asn Val Tyr
            435                 440                 445

Ile Met Ala Asp Lys Gln Lys Asn Gly Ile Lys Val Asn Phe Lys Ile
            450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
            485                 490                 495

Tyr Leu Ser Tyr Gln Ser Ala Leu Ser Lys Asp Pro Asn Glu Lys Arg
            500                 505                 510

Asp His Met Val Leu Leu Glu Phe Val Thr Ala Ala Gly Ile Thr Leu
            515                 520                 525

Gly Met Asp Glu Leu Tyr Lys Phe Cys Tyr Glu Asn Glu Val
            530                 535                 540

<210> SEQ ID NO 4
<211> LENGTH: 223
<212> TYPE: PRT
<213> ORGANISM: Guillardia theta

<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
            35                  40                  45

Ile Ala Tyr Phe Ser Met Ala Ser Gly Gly Gly Trp Val Ile Ala Pro
50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
            85                  90                  95

Trp Asp Ile Met Ala Leu Cys Leu Ser Asp Val Leu Met Ile Ala Thr
            100                 105                 110

Gly Ala Phe Gly Ser Leu Thr Val Gly Asn Val Lys Trp Val Trp Trp
            115                 120                 125

Phe Phe Gly Met Cys Trp Phe Leu His Ile Ile Phe Ala Leu Gly Lys
            130                 135                 140

Ser Trp Ala Glu Ala Ala Lys Ala Lys Gly Gly Asp Ser Ala Ser Val
145                 150                 155                 160

```
Tyr Ser Lys Ile Ala Gly Ile Thr Val Ile Thr Trp Phe Cys Tyr Pro
            165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
            195                 200                 205

Gly Leu Ile Leu Met Ser Gly Ala Ala Thr Gly Tyr Glu Ser Ile
            210                 215                 220

<210> SEQ ID NO 5
<211> LENGTH: 310
<212> TYPE: PRT
<213> ORGANISM: Chlamydomonas reinhardtii

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
            165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
            305
```

-continued 305                310

<210> SEQ ID NO 6
<211> LENGTH: 310
<212> TYPE: PRT
<213> ORGANISM: Artificial sequence
<220> FEATURE:
<223> OTHER INFORMATION: synthetic amino acid sequence

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 7
<211> LENGTH: 310
<212> TYPE: PRT
<213> ORGANISM: Artificial sequence
<220> FEATURE:
<223> OTHER INFORMATION: synthetic amino acid sequence

<400> SEQUENCE: 7

| | | | | | | | | | | | | | | |
|---|---|---|---|---|---|---|---|---|---|---|---|---|---|---|

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 8
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
             35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Ser Glu Gln Ile Asp
            340                 345

<210> SEQ ID NO 9
<211> LENGTH: 344
<212> TYPE: PRT
<213> ORGANISM: Artificial sequence
<220> FEATURE:
<223> OTHER INFORMATION: synthetic amino acid sequence

<400> SEQUENCE: 9

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
                 20                  25                  30

Val Ala Thr Gln Asp Gly Pro Asp Tyr Val Phe His Arg Ala His Glu
             35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 10
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

```
Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Asn Ile Leu Gln Trp
                 85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Pro Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ser Glu Gln Ile Asp
                340                 345

<210> SEQ ID NO 11
<211> LENGTH: 349
<212> TYPE: PRT
<213> ORGANISM: Artificial sequence
<220> FEATURE:
<223> OTHER INFORMATION: synthetic amino acid sequence

<400> SEQUENCE: 11

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
                 20                 25                  30

Val Ala Thr Gln Asp Gly Pro Asp Tyr Val Phe His Arg Ala His Glu
             35                 40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
 65                 70                  75                  80
```

Ser Asn Gly Thr Asn Ala Glu Lys Leu Ala Asn Ile Leu Gln Trp
            85                  90                  95

Ile Thr Phe Ala Leu Ser Ala Leu Cys Leu Met Phe Tyr Gly Tyr Gln
        100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Glu Met Glu Val Glu
                325                 330                 335

Thr Leu Val Ala Glu Glu Glu Asp Ser Glu Gln Ile Asp
            340                 345

<210> SEQ ID NO 12
<211> LENGTH: 258
<212> TYPE: PRT
<213> ORGANISM: Halorubrum sodomense

<400> SEQUENCE: 12

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

```
Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 13
<211> LENGTH: 534
<212> TYPE: PRT
<213> ORGANISM: Artificial sequence
<220> FEATURE:
<223> OTHER INFORMATION: synthetic amino acid sequence

<400> SEQUENCE: 13

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
                100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205
```

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Val Ser Lys Ala Ala Lys Ser Arg
        260                 265                 270

Ile Thr Ser Glu Gly Glu Tyr Ile Pro Leu Asp Gln Ile Asp Ile Asn
            275                 280                 285

Val Val Ser Lys Gly Glu Leu Phe Thr Gly Val Val Pro Ile Leu
290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Phe Ile
                325                 330                 335

Cys Thr Thr Gly Lys Leu Pro Val Pro Trp Pro Thr Leu Val Thr Thr
                340                 345                 350

Phe Gly Tyr Gly Leu Gln Cys Phe Ala Arg Tyr Pro Asp His Met Lys
            355                 360                 365

Gln His Asp Phe Phe Lys Ser Ala Met Pro Glu Gly Tyr Val Gln Glu
        370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
                405                 410                 415

Ile Asp Phe Lys Glu Asp Gly Asn Ile Leu Gly His Lys Leu Glu Tyr
                420                 425                 430

Asn Tyr Asn Ser His Asn Val Tyr Ile Met Ala Asp Lys Gln Lys Asn
            435                 440                 445

Gly Ile Lys Val Asn Phe Lys Ile Arg His Asn Ile Glu Asp Gly Ser
        450                 455                 460

Val Gln Leu Ala Asp His Tyr Gln Gln Asn Thr Pro Ile Gly Asp Gly
465                 470                 475                 480

Pro Val Leu Leu Pro Asp Asn His Tyr Leu Ser Tyr Gln Ser Ala Leu
                485                 490                 495

Ser Lys Asp Pro Asn Glu Lys Arg Asp His Met Val Leu Leu Glu Phe
            500                 505                 510

Val Thr Ala Ala Gly Ile Thr Leu Gly Met Asp Glu Leu Tyr Lys Phe
        515                 520                 525

Cys Tyr Glu Asn Glu Val
    530

<210> SEQ ID NO 14
<211> LENGTH: 248
<212> TYPE: PRT
<213> ORGANISM: Artificial sequence
<220> FEATURE:
<223> OTHER INFORMATION: synthetic amino acid sequence

<400> SEQUENCE: 14

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

-continued

Gly Thr Phe Tyr Phe Ile Val Lys Gly Trp Gly Val Thr Asp Lys Glu
            35                  40                  45

Ala Arg Glu Tyr Tyr Ser Ile Thr Ile Leu Val Pro Gly Ile Ala Ser
 50                      55                  60

Ala Ala Tyr Leu Ser Met Phe Phe Gly Ile Gly Leu Thr Glu Val Thr
 65                  70                  75                  80

Val Ala Gly Glu Val Leu Asp Ile Tyr Tyr Ala Arg Tyr Ala Asp Trp
                 85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
 130                     135                 140

Tyr Ser Trp Trp Leu Phe Ser Thr Ile Cys Met Ile Val Val Leu Tyr
 145                     150                 155                 160

Phe Leu Ala Thr Ser Leu Arg Ala Ala Ala Lys Glu Arg Gly Pro Glu
                 165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
 210                     215                 220

Ala Lys Val Gly Phe Gly Phe Ile Leu Leu Arg Ser Arg Ala Ile Leu
 225                     230                 235                 240

Gly Asp Thr Glu Ala Pro Glu Pro
                 245

<210> SEQ ID NO 15
<211> LENGTH: 321
<212> TYPE: PRT
<213> ORGANISM: Artificial sequence
<220> FEATURE:
<223> OTHER INFORMATION: synthetic amino acid sequence

<400> SEQUENCE: 15

Met Ile Val Asp Gln Phe Glu Glu Val Leu Met Lys Thr Ser Gln Leu
 1               5                  10                  15

Phe Pro Leu Pro Thr Ala Thr Gln Ser Ala Gln Pro Thr His Val Ala
                 20                  25                  30

Pro Val Pro Thr Val Leu Pro Asp Thr Pro Ile Tyr Glu Thr Val Gly
            35                  40                  45

Asp Ser Gly Ser Lys Thr Leu Trp Val Val Phe Val Leu Met Leu Ile
 50                      55                  60

Ala Ser Ala Ala Phe Thr Ala Leu Ser Trp Lys Ile Pro Val Asn Arg
 65                  70                  75                  80

Arg Leu Tyr His Val Ile Thr Thr Ile Ile Thr Leu Thr Ala Ala Leu
                 85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
 130                     135                 140

```
Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala Arg Pro Val Val Ala Val Ser
305                 310                 315                 320

Lys
```

<210> SEQ ID NO 16
<211> LENGTH: 20
<212> TYPE: PRT
<213> ORGANISM: Artificial sequence
<220> FEATURE:
<223> OTHER INFORMATION: synthetic amino acid sequence

<400> SEQUENCE: 16

```
Lys Ser Arg Ile Thr Ser Glu Gly Glu Tyr Ile Pro Leu Asp Gln Ile
1               5                   10                  15

Asp Ile Asn Val
            20
```

<210> SEQ ID NO 17
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 17

```
Phe Cys Tyr Glu Asn Glu Val
1               5
```

<210> SEQ ID NO 18
<211> LENGTH: 26
<212> TYPE: PRT
<213> ORGANISM: Artificial sequence
<220> FEATURE:
<223> OTHER INFORMATION: synthetic amino acid sequence

<400> SEQUENCE: 18

```
Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25
```

```
<210> SEQ ID NO 19
<211> LENGTH: 27
<212> TYPE: PRT
<213> ORGANISM: Artificial sequence
<220> FEATURE:
<223> OTHER INFORMATION: synthetic amino acid sequence

<400> SEQUENCE: 19

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 20
<211> LENGTH: 23
<212> TYPE: PRT
<213> ORGANISM: Artificial sequence
<220> FEATURE:
<223> OTHER INFORMATION: synthetic amino acid sequence

<400> SEQUENCE: 20

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 21
<211> LENGTH: 18
<212> TYPE: PRT
<213> ORGANISM: Artificial sequence
<220> FEATURE:
<223> OTHER INFORMATION: synthetic amino acid sequence

<400> SEQUENCE: 21

Met Arg Gly Thr Pro Leu Leu Leu Val Val Ser Leu Phe Ser Leu Leu
1               5                   10                  15

Gln Asp

<210> SEQ ID NO 22
<211> LENGTH: 5
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(3)
<223> OTHER INFORMATION: the amino acid in this position may be any
      amino acid

<400> SEQUENCE: 22

Val Xaa Xaa Ser Leu
1               5

<210> SEQ ID NO 23
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 23

Val Lys Glu Ser Leu
1               5
```

```
<210> SEQ ID NO 24
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 24

Val Leu Gly Ser Leu
1               5

<210> SEQ ID NO 25
<211> LENGTH: 16
<212> TYPE: PRT
<213> ORGANISM: Artificial sequence
<220> FEATURE:
<223> OTHER INFORMATION: synthetic amino acid sequence

<400> SEQUENCE: 25

Asn Ala Asn Ser Phe Cys Tyr Glu Asn Glu Val Ala Leu Thr Ser Lys
1               5                   10                  15

<210> SEQ ID NO 26
<211> LENGTH: 6
<212> TYPE: PRT
<213> ORGANISM: Artificial sequence
<220> FEATURE:
<223> OTHER INFORMATION: synthetic amino acid sequence
<220> FEATURE:
<221> NAME/KEY: MISC_FEATURE
<222> LOCATION: (2)..(2)
<223> OTHER INFORMATION: the amino acid in this position may be any
      amino acid

<400> SEQUENCE: 26

Phe Xaa Tyr Glu Asn Glu
1               5

<210> SEQ ID NO 27
<211> LENGTH: 18
<212> TYPE: PRT
<213> ORGANISM: Artificial sequence
<220> FEATURE:
<223> OTHER INFORMATION: synthetic amino acid sequence

<400> SEQUENCE: 27

Met Thr Glu Thr Leu Pro Pro Val Thr Glu Ser Ala Val Ala Leu Gln
1               5                   10                  15

Ala Glu
```